US012788425B2

(12) United States Patent
Black et al.

(10) Patent No.: US 12,788,425 B2
(45) Date of Patent: Nov. 10, 2026

(54) ULTRASONIC SURGICAL INSTRUMENT WITH A DISTALLY GROUNDED ACOUSTIC WAVEGUIDE

(71) Applicant: Cilag GmbH International, Zug (CH)

(72) Inventors: Brian D. Black, Loveland, OH (US); Matthew T. Stone, Mason, OH (US); Andrew T. Beckman, Cincinnati, OH (US); Charles J. Scheib, Loveland, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 186 days.

(21) Appl. No.: 18/647,584

(22) Filed: Apr. 26, 2024

(65) Prior Publication Data

US 2024/0293144 A1 Sep. 5, 2024

Related U.S. Application Data

(63) Continuation of application No. 17/076,959, filed on Oct. 22, 2020, now Pat. No. 11,998,227.

(51) Int. Cl.
*A61B 17/32* (2006.01)
*A61B 17/29* (2006.01)
(Continued)

(52) U.S. Cl.
CPC ................. *A61B 17/320092* (2013.01); *A61B 2017/2927* (2013.01); *A61B 2017/320093* (2017.08);
(Continued)

(58) Field of Classification Search
CPC ............ A61B 17/2812; A61B 17/2816; A61B 17/295; A61B 17/32; A61B 17/320068;
(Continued)

(56) References Cited

U.S. PATENT DOCUMENTS 7,354,440 B2 4/2008 Truckai et al.
7,381,209 B2 6/2008 Truckai et al.
(Continued)

FOREIGN PATENT DOCUMENTS

WO WO 2021/038372 A1 3/2021

OTHER PUBLICATIONS

European Examination Report dated Feb. 1, 2023, for Application No. 21806358.4, 4 pages.
(Continued)

*Primary Examiner* — Robert A Lynch
(74) *Attorney, Agent, or Firm* — FBT Gibbons LLP

(57) ABSTRACT

An ultrasonic surgical instrument includes an end effector, a shaft assembly, and a waveguide grounding feature. The end effector includes an ultrasonic blade and a clamp arm movable between an open position and a closed position. The shaft assembly includes a proximal shaft portion extending along a longitudinal axis, an acoustic waveguide extending proximally from the ultrasonic blade, a distal shaft portion extending along a distal axis, and an articulation section interposed between the proximal shaft portion and the distal shaft portion. The articulation section can deflect the distal shaft portion and the end effector relative to the longitudinal axis between a straight configuration and an articulated configuration. The waveguide grounding feature inhibits the ultrasonic blade from shifting relative to the clamp arm along the distal axis as the end effector is driven between the straight configuration and the articulated configuration.

16 Claims, 59 Drawing Sheets

(51) Int. Cl.
*A61B 34/20* (2016.01)
*A61B 34/37* (2016.01)

(52) U.S. Cl.
CPC ............. *A61B 2017/320094* (2017.08); *A61B 2034/2051* (2016.02); *A61B 34/37* (2016.02)

(58) Field of Classification Search
CPC .. A61B 17/320092; A61B 2017/00309; A61B 2017/00314; A61B 2017/00323; A61B 2017/2927; A61B 2017/320016; A61B 2017/320069; A61B 2017/320071; A61B 2017/320074; A61B 2017/320075; A61B 2017/320082; A61B 2017/320093; A61B 2017/320094; A61B 34/37; A61B 2034/2051
See application file for complete search history.

(56) References Cited

U.S. PATENT DOCUMENTS

| | | | |
|---|---|---|---|
| 8,663,220 | B2 | 3/2014 | Wiener et al. |
| 8,986,302 | B2 | 3/2015 | Aldridge et al. |
| 9,095,367 | B2 * | 8/2015 | Olson ............ A61B 17/320092 |
| 9,949,785 | B2 | 4/2018 | Price et al. |
| 10,172,636 | B2 | 1/2019 | Stulen et al. |
| 11,457,945 | B2 | 10/2022 | Hunter et al. |
| 11,471,181 | B2 | 10/2022 | Hunter et al. |
| 11,484,333 | B2 | 11/2022 | Worrell et al. |
| 11,612,409 | B2 | 3/2023 | Black et al. |
| 11,690,642 | B2 | 7/2023 | Black et al. |
| 11,712,261 | B2 | 8/2023 | Hunter et al. |
| 11,890,030 | B2 | 2/2024 | Black et al. |
| 2006/0079874 | A1 | 4/2006 | Faller et al. |
| 2007/0191713 | A1 | 8/2007 | Eichmann et al. |
| 2008/0200940 | A1 | 8/2008 | Eichmann et al. |
| 2009/0036913 | A1 | 2/2009 | Wiener et al. |
| 2014/0005702 | A1 | 1/2014 | Timm et al. |
| 2015/0080924 | A1 | 3/2015 | Stulen et al. |
| 2016/0302819 | A1 * | 10/2016 | Stulen ............ A61B 17/320092 |
| 2016/0374708 | A1 | 12/2016 | Wiener et al. |
| 2019/0021756 | A1 | 1/2019 | Boudreaux |
| 2019/0216493 | A1 | 7/2019 | Worrell et al. |
| 2020/0093554 | A1 * | 3/2020 | Schuh .................... A61B 34/71 |
| 2021/0015572 | A1 | 1/2021 | Gomez et al. |
| 2021/0022815 | A1 | 1/2021 | Abbott |
| 2021/0059709 | A1 | 3/2021 | Black et al. |
| 2021/0353325 | A1 * | 11/2021 | Fagan ...................... A61B 8/12 |
| 2022/0125460 | A1 | 4/2022 | Black et al. |
| 2022/0125461 | A1 | 4/2022 | Black et al. |
| 2022/0125464 | A1 | 4/2022 | Black et al. |
| 2022/0125465 | A1 | 4/2022 | Beckman et al. |
| 2022/0125466 | A1 | 4/2022 | Beckman et al. |
| 2022/0125467 | A1 | 4/2022 | Black et al. |
| 2022/0125468 | A1 | 4/2022 | Scheib et al. |
| 2022/0125469 | A1 | 4/2022 | Black et al. |
| 2022/0125470 | A1 | 4/2022 | Black et al. |
| 2022/0125471 | A1 | 4/2022 | Black et al. |
| 2022/0125472 | A1 | 4/2022 | Beckman et al. |
| 2022/0125473 | A1 | 4/2022 | Black et al. |

OTHER PUBLICATIONS

Extended European Search Report dated Feb. 13, 2024, for Application No. 23211001.5, 8 pages.
International Search Report and Written Opinion dated Mar. 22, 2022, for International Application No. PCT/IB2021/059592, 21 pages.
U.S. Appl. No. 62/930,638, entitled "Articulation Joint with Helical Luman," filed Nov. 5, 2019.
Chinese First Office Action and Search Report dated Jan. 9, 2026. For Application No. 202180086538.7, 12 pages.

* cited by examiner

ULTRASONIC SURGICAL INSTRUMENT WITH A DISTALLY GROUNDED ACOUSTIC WAVEGUIDE

CROSS-REFERENCE TO RELATED APPLICATION

This application claims priority to U.S. Non-provisional patent application Ser. No. 17/076,959, entitled "Ultrasonic Surgical Instrument with a Distally Grounded Acoustic Waveguide," filed Oct. 22, 2020, published as U.S. Pat. Pub. No. 2022/0125464 on Apr. 28, 2022, the disclosure of which is hereby incorporated by reference herein.

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

In one example, the end effector of the surgical instrument includes a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned, the disclosure of which is incorporated by reference herein.

Examples of robotic systems, at least some of which have ultrasonic features and/or associated articulatable portions, include U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 on Oct. 4, 2022; U.S. patent application Ser. No. 16/556,727, entitled "Rotatable Linear Actuation Mechanism," filed on Aug. 30, 2019, issued as U.S. Pat. No. 11,712,261 on Aug. 1, 2023; and/or U.S. Pat. App. No. 62/930,638, entitled "Articulation Joint with Helical Lumen," filed on Nov. 5, 2019. The disclosure of each of these applications is incorporated by reference herein.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
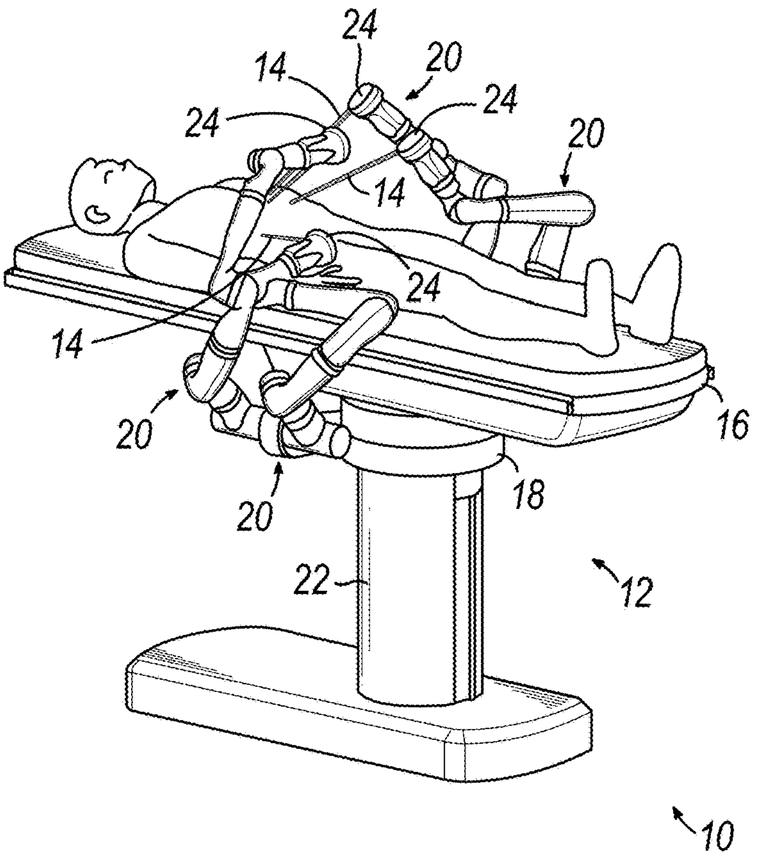
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," "transverse," "upper," "lower," "righthand," and "lefthand" also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Exemplary Robotically-Enabled Medical System

FIG. 1 shows an exemplary robotically-enabled medical system, including a first example of a table-based robotic system (10). Table-based robotic system (10) of the present example includes a table system (12) operatively connected to an instrument for a diagnostic and/or therapeutic procedure in the course of treating a patient. Such procedures may include, but are not limited, to bronchoscopy, ureteroscopy, a vascular procedure, and a laparoscopic procedure. To this end, the instrument illustrated in the present example is an ultrasonic surgical instrument (14) configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein. As described therein and as will be described in greater detail below, ultrasonic surgical instrument (14) is operable to cut tissue and seal or weld tissue (e.g., a blood vessel, etc.) substantially simultaneously. While one or more examples incorporates various ultrasonic features, such as ultrasonic surgical instrument (14), the invention is not intended to be unnecessarily limited to the ultrasonic features described herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate ultrasonic surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as ultrasonic surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
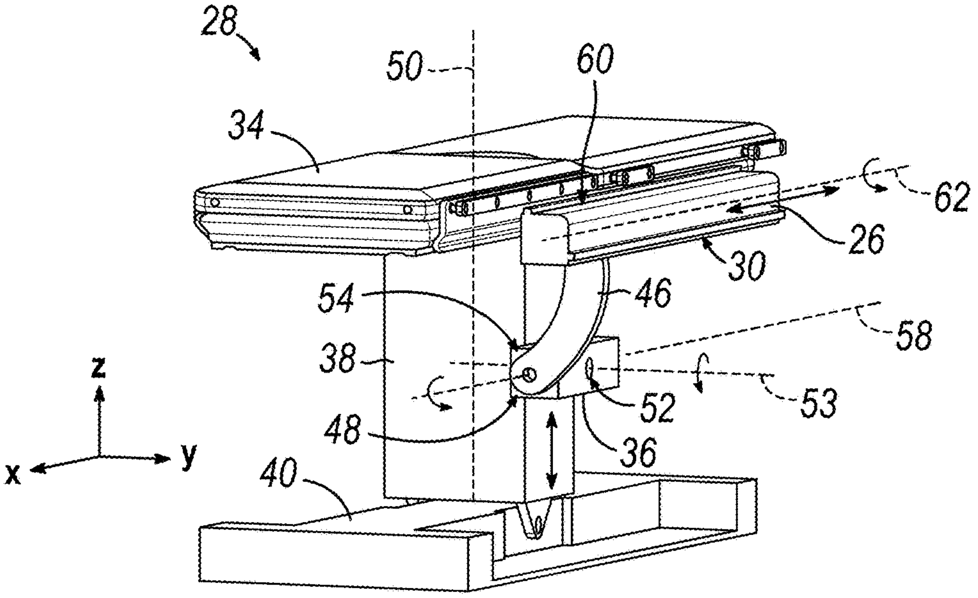
FIG. 2 depicts a perspective view of a second example of a table-based robotic system.
Figure 3:
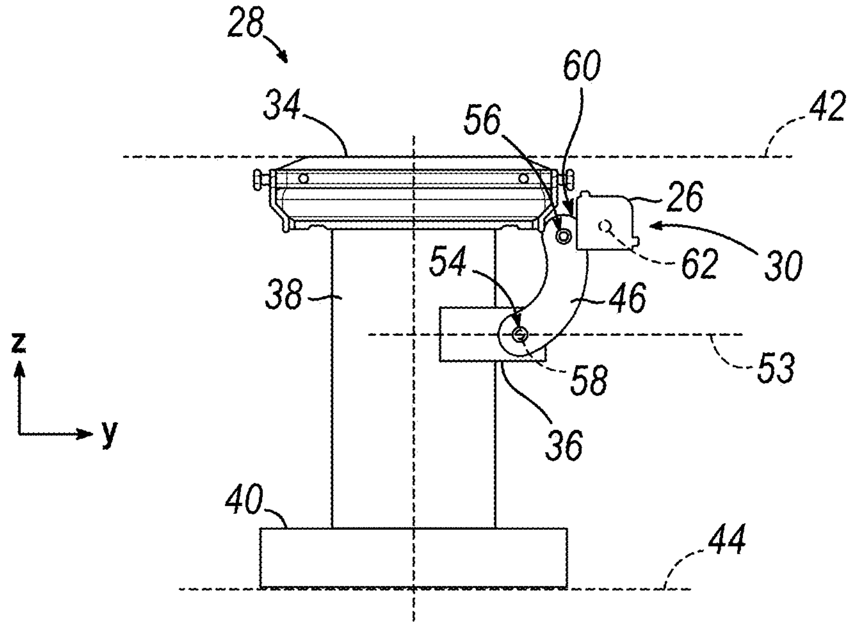
FIG. 3 depicts an end elevational view of the table-based robotic system of FIG. 2.
Figure 4:
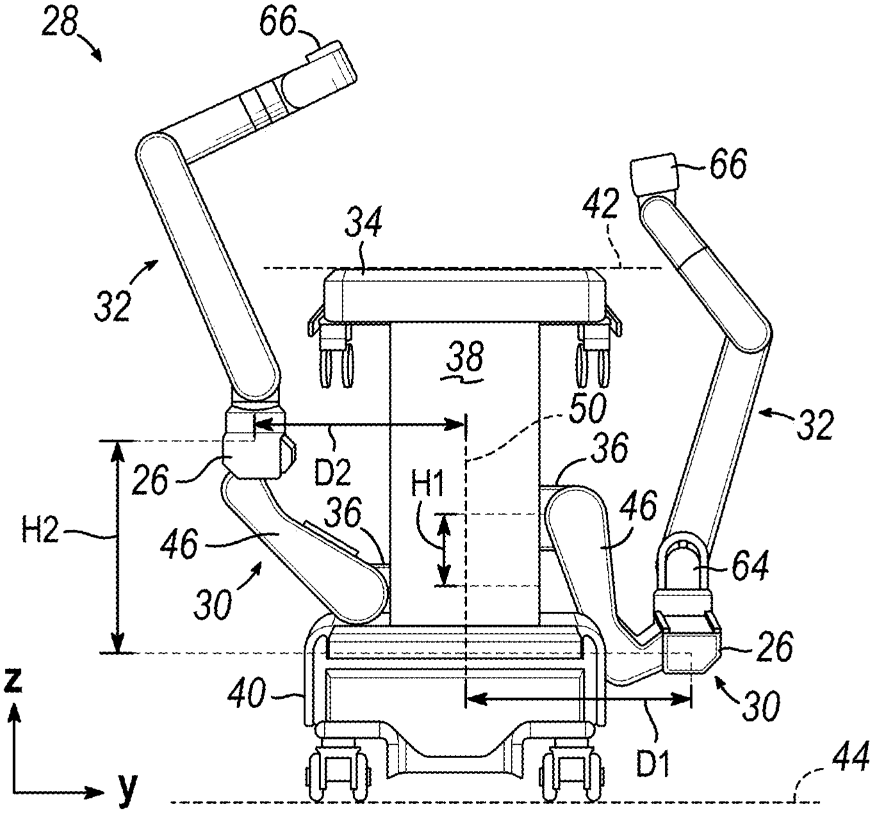
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as ultrasonic surgical instrument (14) (see FIG. 6A), the instrument includes an instrument-based insertion architecture.

Figure 5:
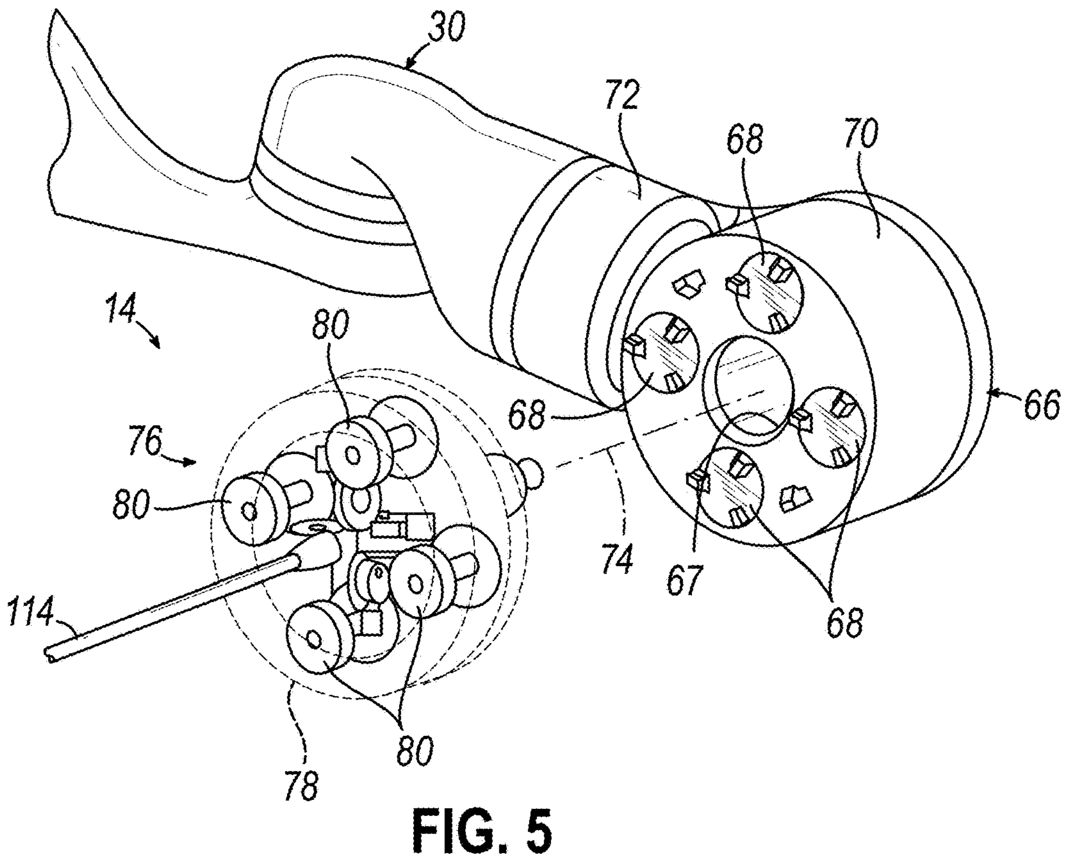
FIG. 5 depicts a partially exploded perspective view of the robotic arm of FIG. 4 having an instrument driver and a first exemplary surgical instrument.

FIG. 5 shows one example of instrument driver (66) in greater detail with ultrasonic surgical instrument (14) removed therefrom. Given the present instrument-based insertion architecture shown with reference to ultrasonic surgical instrument (14), instrument driver (66) further includes a clearance bore (67) extending entirely therethrough so as to movably receive a portion of ultrasonic surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of ultrasonic surgical instrument (14). Instrument driver (66) and ultrasonic surgical instrument (14) of the present example are aligned such that the axes of each drive output (68) are parallel to the axis ultrasonic surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with ultrasonic surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. First Exemplary Ultrasonic Surgical Instrument

Figure 6A:
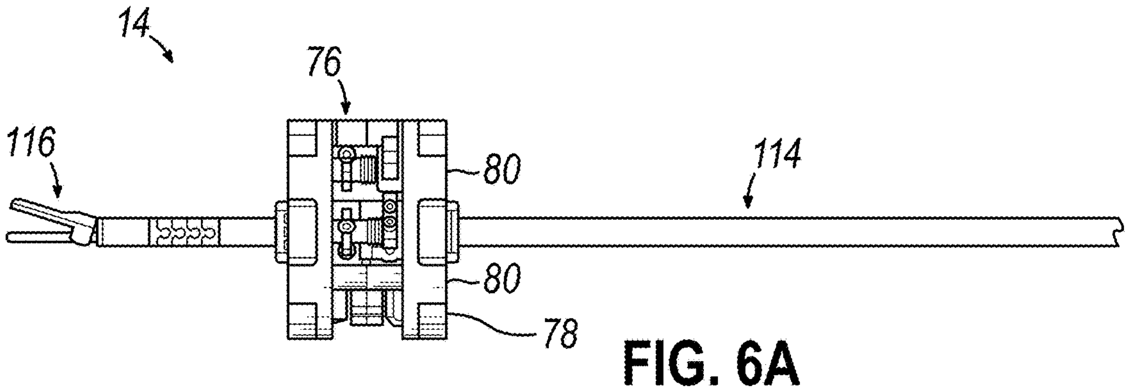
FIG. 6A depicts a side elevational view of the surgical instrument of FIG. 5 in a retracted position.
Figure 6B:
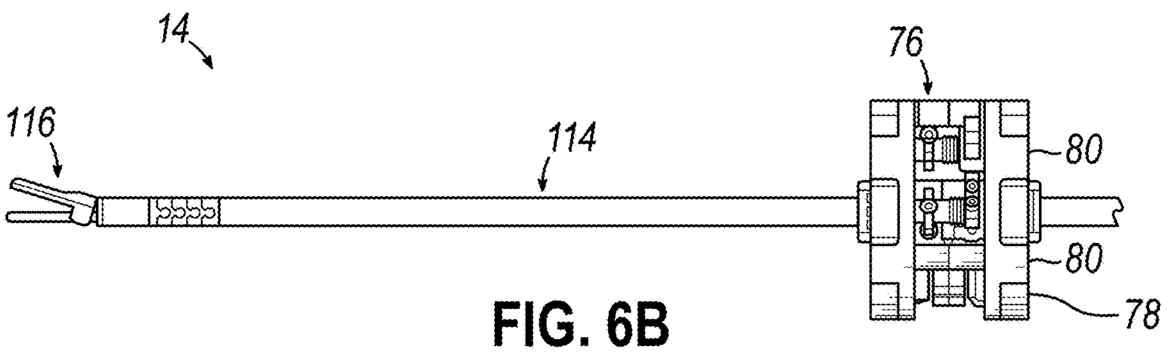
FIG. 6B depicts the side elevational view the surgical instrument similar to FIG. 6A, but in an extended position.

With respect to FIGS. 5-6B and in cooperation with instrument driver (66) discussed above, ultrasonic surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of base (76) with an axis substantially parallel to the axes of the drive inputs (80) as discussed briefly above. With shaft assembly (114) positioned at the center of base (76), shaft assembly (114) is coaxial with instrument driver axis (74) when attached and movably received in clearance bore (67). Thus, rotation of rotational assembly (70) causes shaft assembly (114) of ultrasonic surgical instrument (14) to rotate about its own longitudinal axis while clearance bore (67) provides space for translation of shaft assembly (114) during use.

To this end, FIGS. 5-6B show ultrasonic surgical instrument (14) having the instrument-based insertion architecture as discussed briefly above. Ultrasonic surgical instrument (14) includes elongated shaft assembly (114), an end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, ultrasonic surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

i. First Exemplary End Effector and Acoustic Drivetrain

Figure 7A:
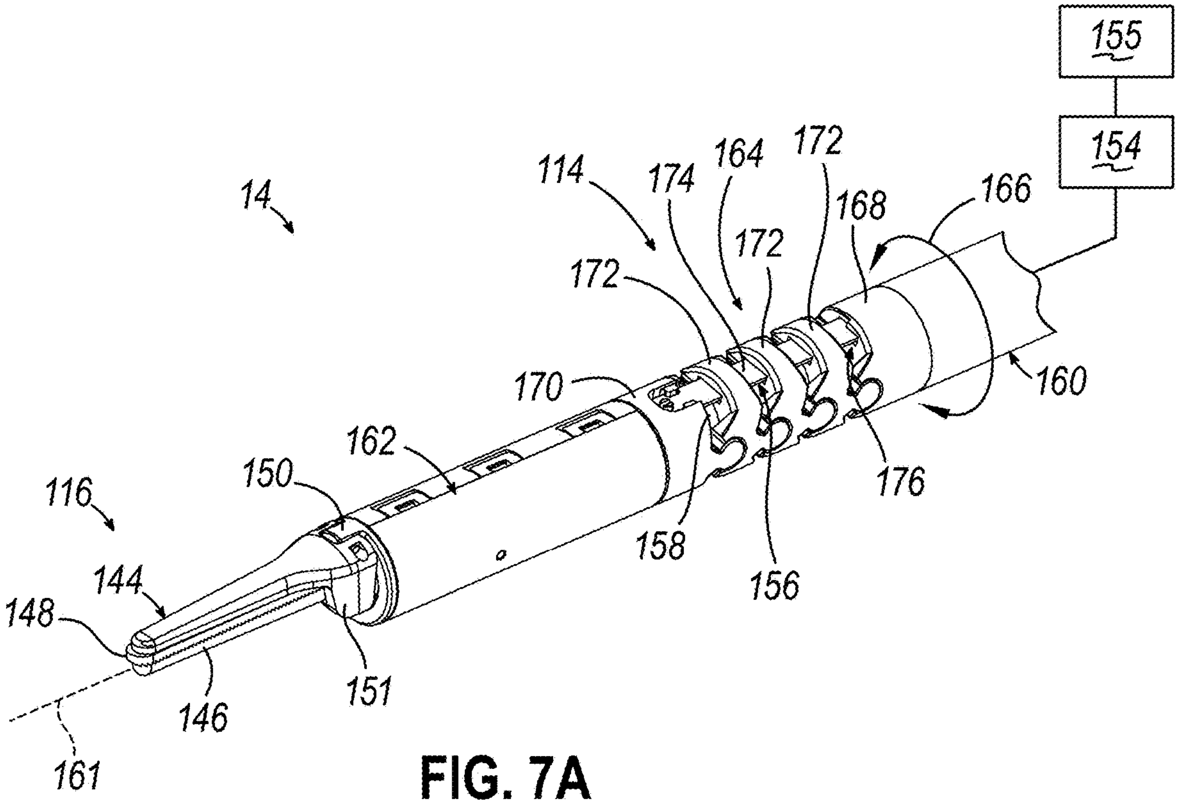
FIG. 7A depicts an enlarged perspective view of the surgical instrument of FIG. 6A with an end effector in a closed position and a shaft assembly in a straight configuration.
Figure 7B:
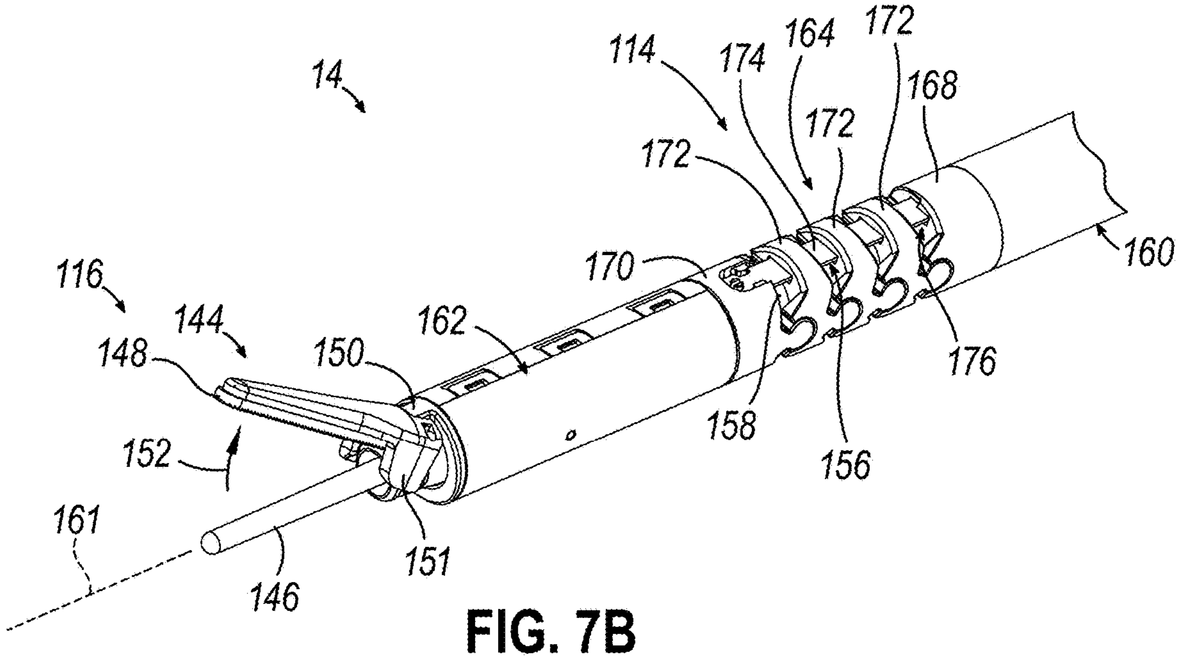
FIG. 7B depicts the enlarged perspective view of the surgical instrument similar to FIG. 7A, but showing the end effector in an open position.

As best seen in FIGS. 7A-7B, end effector (116) of the present example includes a clamp arm (144) and an ultrasonic blade (146). Clamp arm (144) has a clamp pad (148) secured to an underside of clamp arm (144), facing blade (146). Clamp arm (144) is pivotally secured to a distally projecting tongue (150) of shaft assembly (114). Clamp arm (144) is operable to selectively pivot toward and away from blade (146) to selectively clamp tissue between clamp arm (144) and blade (146). A pair of arms (151) extend transversely from clamp arm (144) and are pivotally secured to another portion of shaft assembly (114) configured to longitudinally slide to pivot clamp arm (144) as indicated by an arrow (152) between a closed position shown in FIG. 7A and an open position shown in FIG. 7B.

Blade (146) of the present example is operable to vibrate at ultrasonic frequencies in order to effectively cut through and seal tissue, particularly when the tissue is being compressed between clamp pad (148) and blade (146). Blade (146) is positioned at a distal end of an acoustic drivetrain. This acoustic drivetrain includes a transducer assembly (154) and an acoustic waveguide (156), which includes a flexible portion (158) discussed below in greater detail.

Transducer assembly (154) is further connected to a generator (155) of the acoustic drivetrain. More particularly, transducer assembly (154) is coupled with generator (155) such that transducer assembly (154) receives electrical power from generator (155). Piezoelectric elements (not shown) in transducer assembly (154) convert that electrical power into ultrasonic vibrations. By way of example only, generator (155) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

When transducer assembly (154) of the present example is activated, mechanical oscillations are transmitted through waveguide (156) to reach blade (146), thereby providing oscillation of blade (146) at a resonant ultrasonic frequency (e.g., 55.5 kHz). Thus, when tissue is secured between blade (146) and clamp pad (148), the ultrasonic oscillation of blade (146) may simultaneously sever the tissue and denature the proteins in adjacent tissue cells, thereby providing a coagulative effect with relatively little thermal spread.

ii. First Exemplary Shaft Assembly and Articulation Section

As shown in FIGS. 7A-7B, shaft assembly (114) includes a proximal shaft portion (160) extending along a longitudinal axis (161), a distal shaft portion (162) distally projecting relative to proximal shaft portion (160), and an articulation section (164) extending between proximal and distal shaft portions (160, 162). Shaft assembly (114) is configured to rotate about longitudinal axis (161) as indicated by an arrow (166). In one example, shaft assembly (114) rotates in the clockwise or counterclockwise directions completely around longitudinal axis (161) and may be selectively fixed in any rotational position about longitudinal axis (161) for positioning articulation section (164) and/or end effector (116) about longitudinal axis (161).

Articulation section (164) is configured to selectively position end effector (116) at various lateral deflection angles relative to longitudinal axis (161) defined by proximal shaft portion (160). Articulation section (164) may take a variety of forms. In the present example, articulation section (164) includes a proximal link (168), a distal link (170), and a plurality of intermediate links (172) connected in series between proximal and distal links (168, 170). Articulation section (164) further includes a pair of articulation bands (174) extending along a pair of respective channels (176) collectively defined through links (168, 170, 172). Links (168, 170, 172) are generally configured to pivot relative to each other upon actuation of articulation bands (174) to thereby bend articulation section (164) with flexible portion (158) of waveguide (156) therein to achieve an articulated state.

Figure 8A:
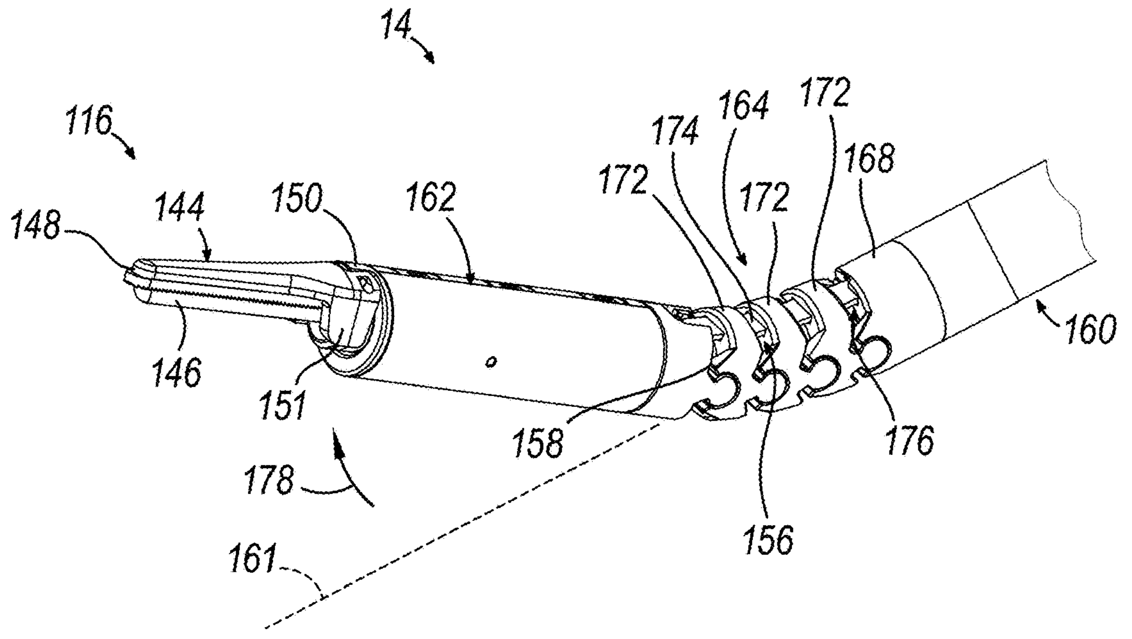
FIG. 8A depicts an enlarged perspective view of the surgical instrument of FIG. 6A with the end effector in a closed position and the shaft assembly in a first articulated configuration.
Figure 8B:
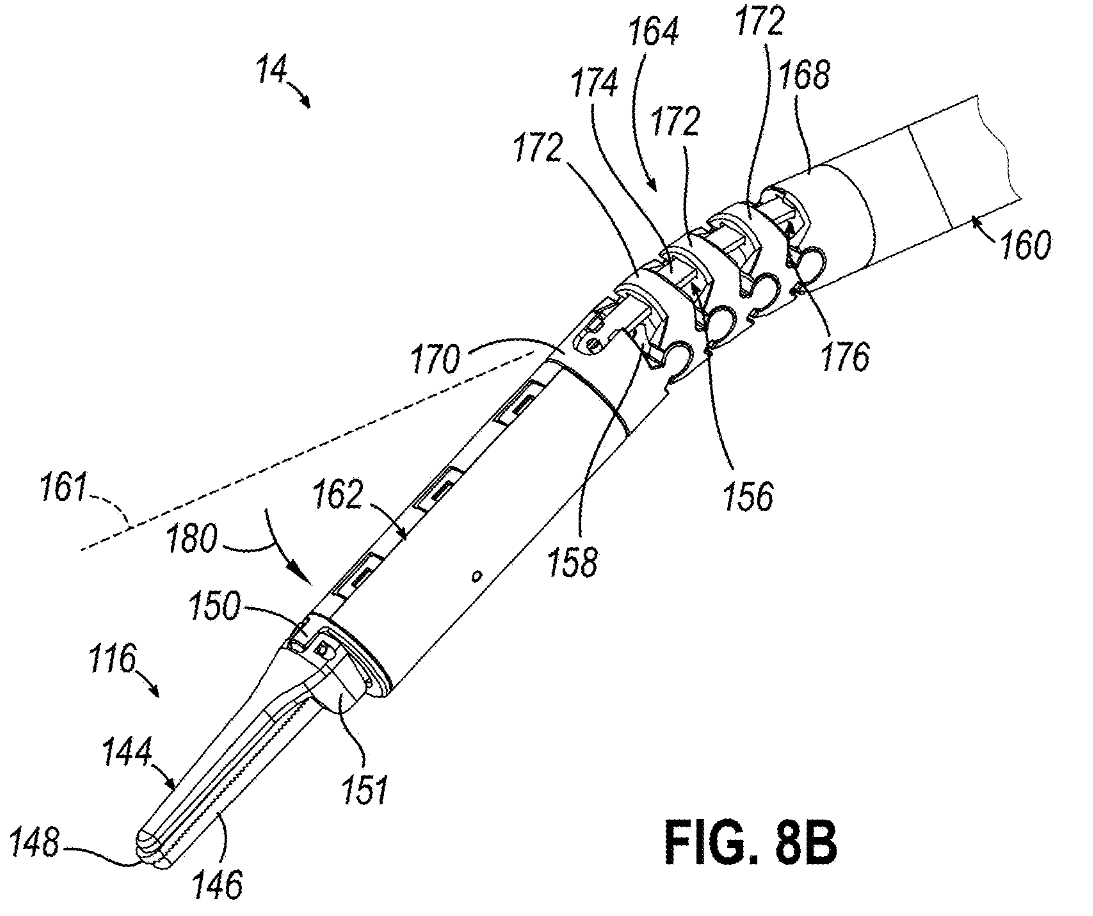
FIG. 8B depicts the enlarged perspective view of the surgical instrument similar to FIG. 8A, but with the shaft assembly in a second articulated configuration.

Links (168, 170, 172) shown in FIGS. 7B-8B pivotally interlock to secure distal shaft portion (162) relative to proximal shaft portion (160) while allowing for deflection of distal shaft portion (162) relative to longitudinal axis (161). Thus, as a pair of articulation bands (174) translate longitudinally in an opposing fashion, this will cause articulation section (164) to bend via links (168, 170, 172) thereby laterally deflecting end effector (116) away from the longitudinal axis (161) of proximal shaft portion (160) from a straight configuration as shown in FIG. 7B to a first articulated configuration as shown in FIG. 8A and indicated by an arrow (178) or a second articulated configuration as shown in FIG. 8B and indicated by an arrow (180). Furthermore, flexible acoustic waveguide (156) is configured to effectively communicate ultrasonic vibrations from waveguide (156) to blade (146) even when articulation section (164) is in an articulated configuration as shown in FIGS. 8A-8B.

II. Exemplary Ultrasonic Surgical Instrument Having Articulation and Dual End Effector Roll As mentioned above, and as shown in FIG. 7A, shaft assembly (114) is configured to rotate about longitudinal axis (161), as indicated by arrow (166), such that articulation section (164) and end effector (116) may be selectively fixed in any rotational position about longitudinal axis (161). In such instances, ultrasonic blade (146) and clamp arm (144) may be configured to rotate about longitudinal axis (161) (i.e., roll about axis (161)), together. Since flexible portion (158) of waveguide (156) is configured to effectively communicate ultrasonic vibrations from waveguide (156) to blade (146), flexible portion (158) and waveguide (156) may rotate with ultrasonic blade (146) about longitudinal axis (161) (i.e., roll about axis (161)). Therefore, when ultrasonic blade (146) and clamp arm (144) roll about axis (161) together, the plane at which articulation section (164) laterally deflects end effector (116) also rotates about longitudinal axis (161).

In addition to blade (146) and clamp arm (144) rolling about longitudinal axis (161) together, it may be desirable to rotate clamp arm (144) about a longitudinal axis defined by ultrasonic blade (146) relative to both ultrasonic blade (146) and flexible portion (158) of waveguide (156). In other words, it may be desirable for end effector (116) to have dual roll functionality such that clamp arm (144) may roll with ultrasonic blade (146) and flexible portion (158) of waveguide (156) about axis (161), while clamp arm (144) may also roll relative to ultrasonic blade (146) about the longitudinal axis defined by ultrasonic blade (146).

Further, it may be desirable to roll clamp arm (144) relative to blade (146) about the longitudinal axis defined by blade (146) while end effector (116) is laterally deflected. Even further, is may be desirable to maintain the ability to open and close clamp arm (144) relative to blade (146) regardless of (i) the roll position of clamp arm (144) relative to blade (146), and (ii) the lateral deflection of end effector (116). In other words, it may be desirable to control the roll position of clamp arm (144) relative to blade (146), and open and close clamp arm (144) relative to blade (146), while articulation section (164) is in either the straight configuration or any suitable articulated configuration. The term "straight configuration" may also be referred to as a "non-articulated configuration" as used herein.

Having such capabilities may lead to an operator having greater control of surgical instrument (14) compared to an end effector (116) limited to only rolling blade (146) and clamp arm (144) about longitudinal axis (161) together. For instance, the operator may control the rotational position of the flexible portion (158) of waveguide (156), and therefore the plane at which articulation section (164) laterally deflects end effector (116); while also controlling the rotational position of clamp arm (144) relative to both blade (146) and flexible portion (158) of waveguide (156) about the longitudinal axis defined by blade (146). Therefore, clamp arm (144) may be positioned at multiple locations around blade (146) about the longitudinal axis defined by blade (146), even while end effector (116) is deflected. By also maintaining the capability of clamp arm (144) to open and close while end effector (116) is deflected, end effector (116) may grasp and manipulate tissue in accordance with the teachings herein, on a variety of longitudinally extending contact surfaces located on an exterior of blade (146).

Figure 11A:
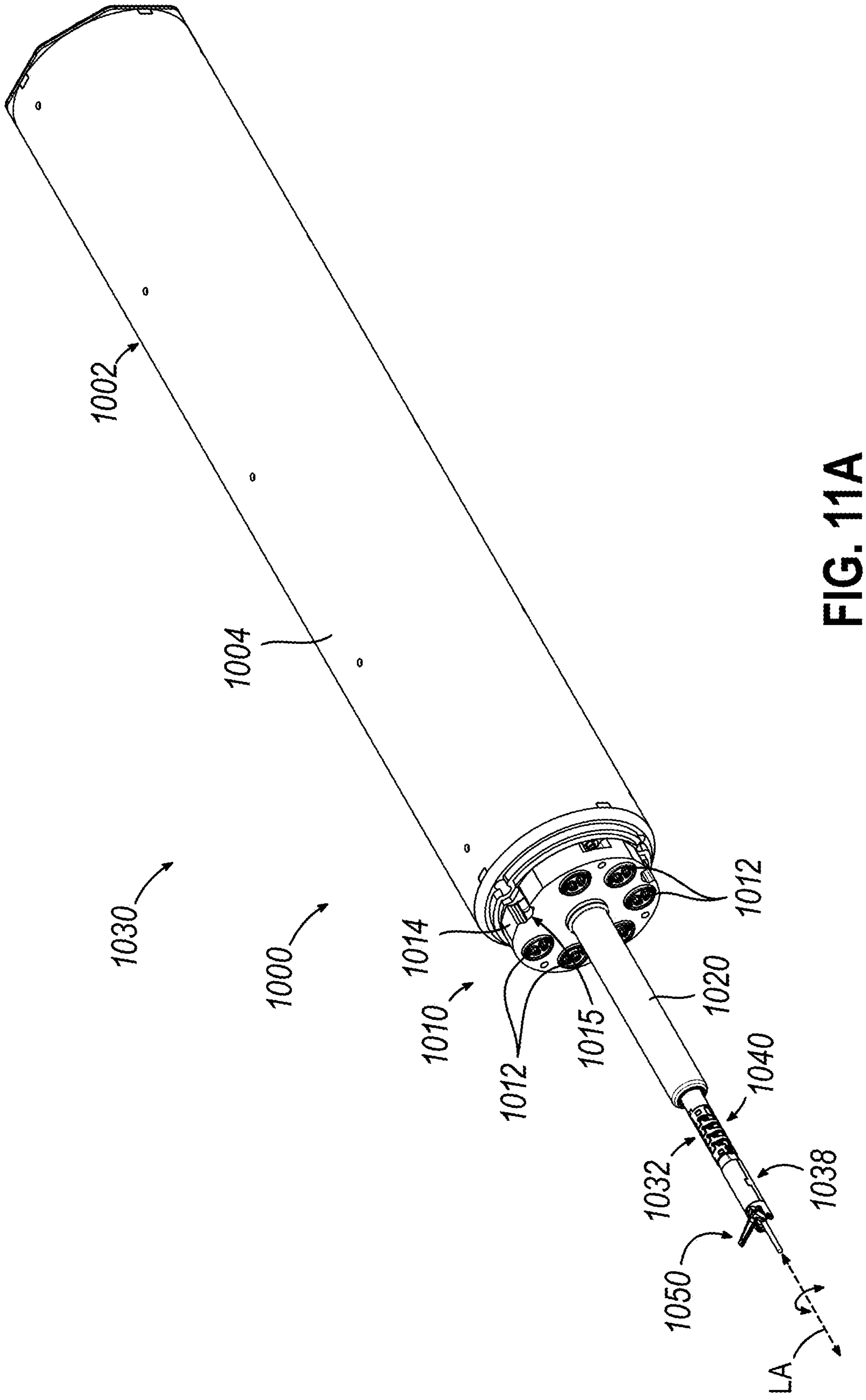
FIG. 11A depicts a perspective view of the instrument base of FIG. 9, an exemplary shaft assembly, and an exemplary end effector coupled together to form an exemplary ultrasonic surgical instrument configured to couple with an exemplary robotic arm, where the shaft assembly and end effector are in a proximal position.
Figure 11B:
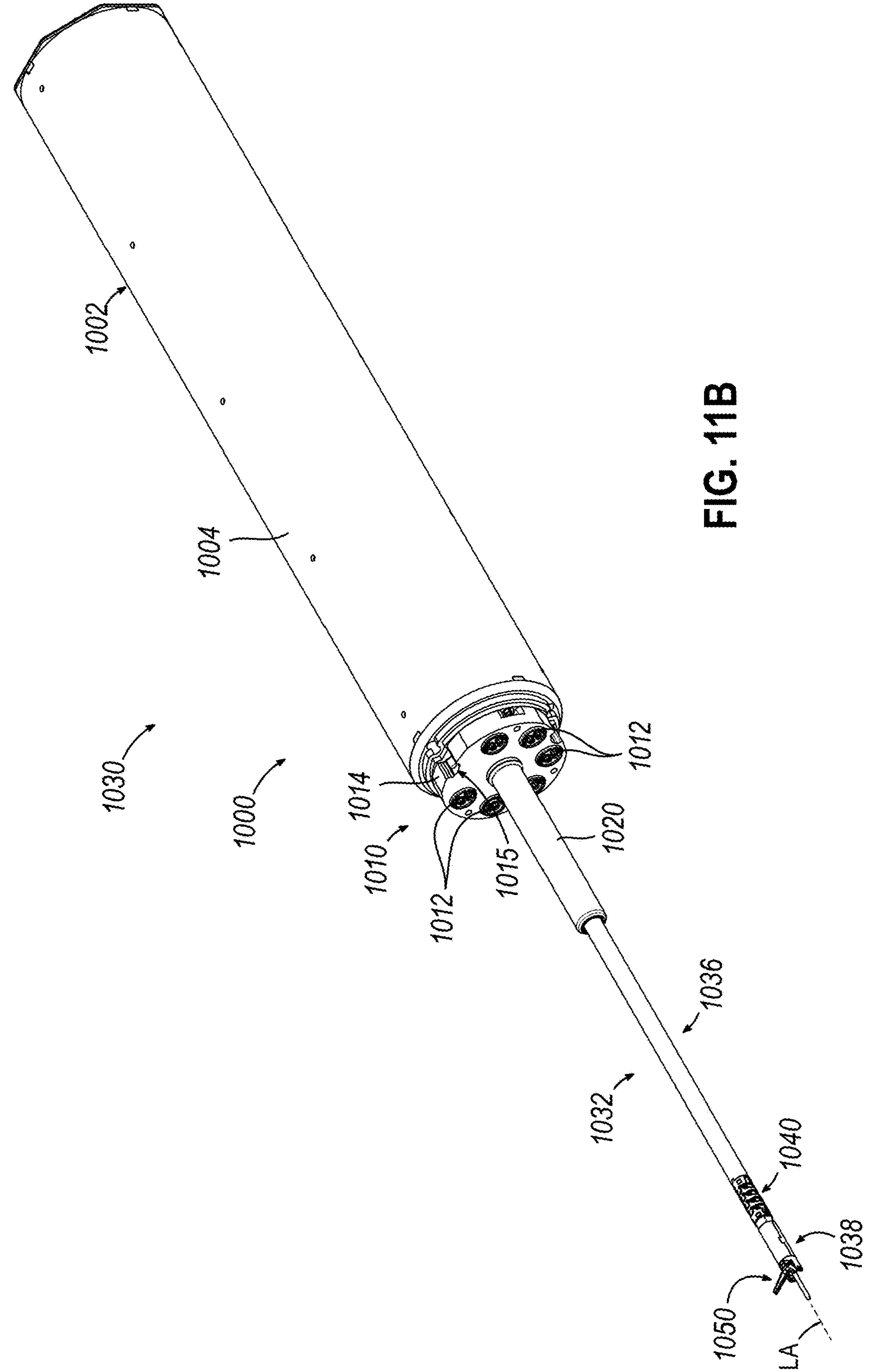
FIG. 11B depicts the ultrasonic surgical instrument of FIG. 11A, where the shaft assembly and the end effector are in a distal position.

FIGS. 11A-11B show an alternative ultrasonic surgical instrument (1030) that may be incorporated into an exemplary robotic arm substantially similar to robotic arm (20, 32) described above, with any differences elaborated below. Therefore, ultrasonic surgical instrument (1030) may be substantially similar to ultrasonic surgical instrument (14) described above, except as otherwise described below.

Ultrasonic surgical instrument (1030) includes an instrument base (1000), a shaft assembly (1032) partially housed within, and extending distally from, instrument base (1000), and an end effector (1050) extending distally from shaft assembly (1032). Instrument base (1000), shaft assembly (1032), and end effector (1050) may be substantially similar to instrument base (76), shaft assembly (114), and end effector (116) described above, with differences elaborated below. As will be described in greater detail below, instrument base (1000) is configured to couple with a suitable robotic arm such that instrument base (1000) may actuate shaft assembly (1032) and end effector (1050) in accordance with the description herein. As will be described in greater detail below, end effector (1050) is configured with dual roll capabilities similar to those briefly described above.

A. Exemplary Instrument Base

Figure 9:
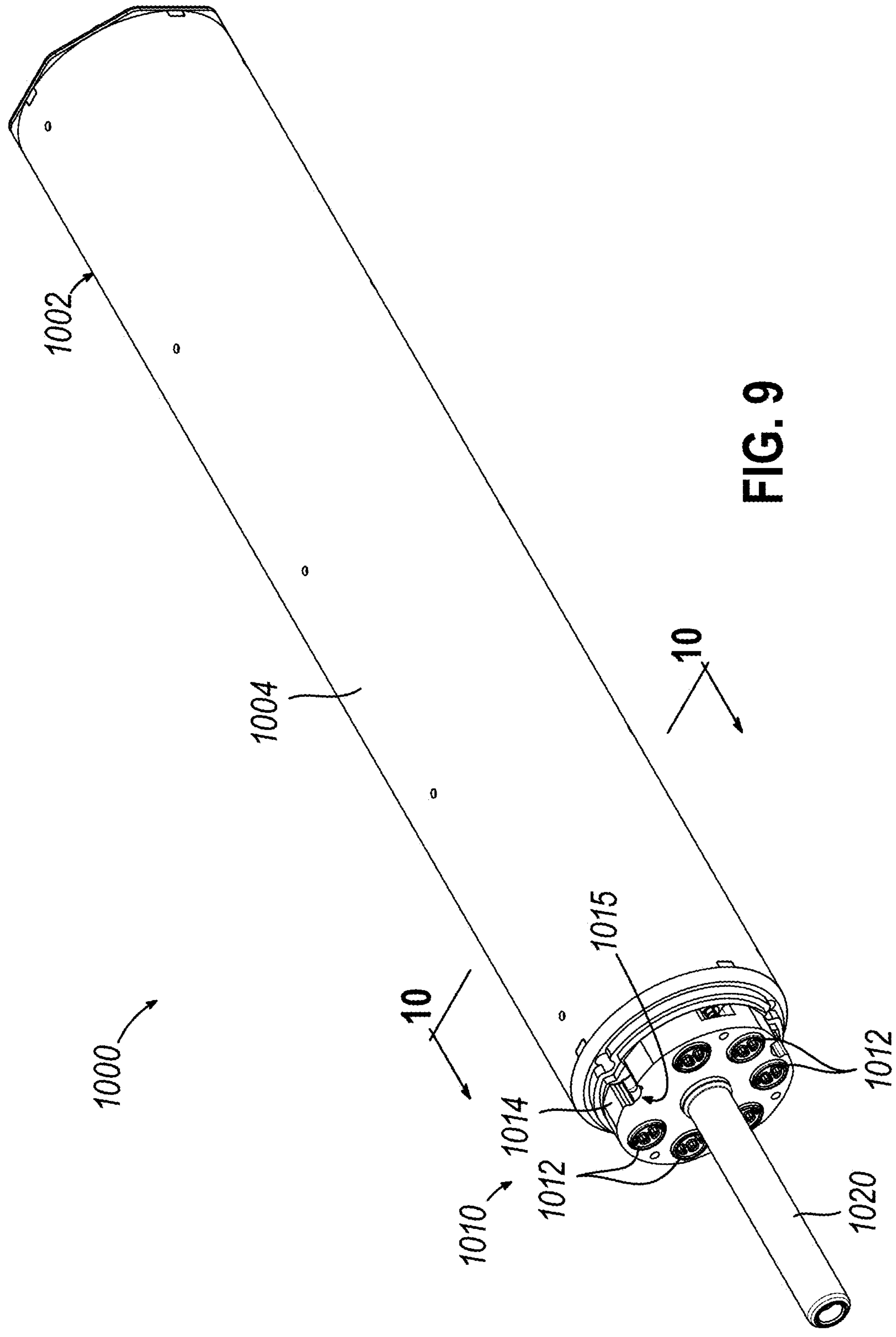
FIG. 9 depicts a perspective view of an exemplary instrument base that may be configured to couple with an exemplary robotic arm.
Figure 10:
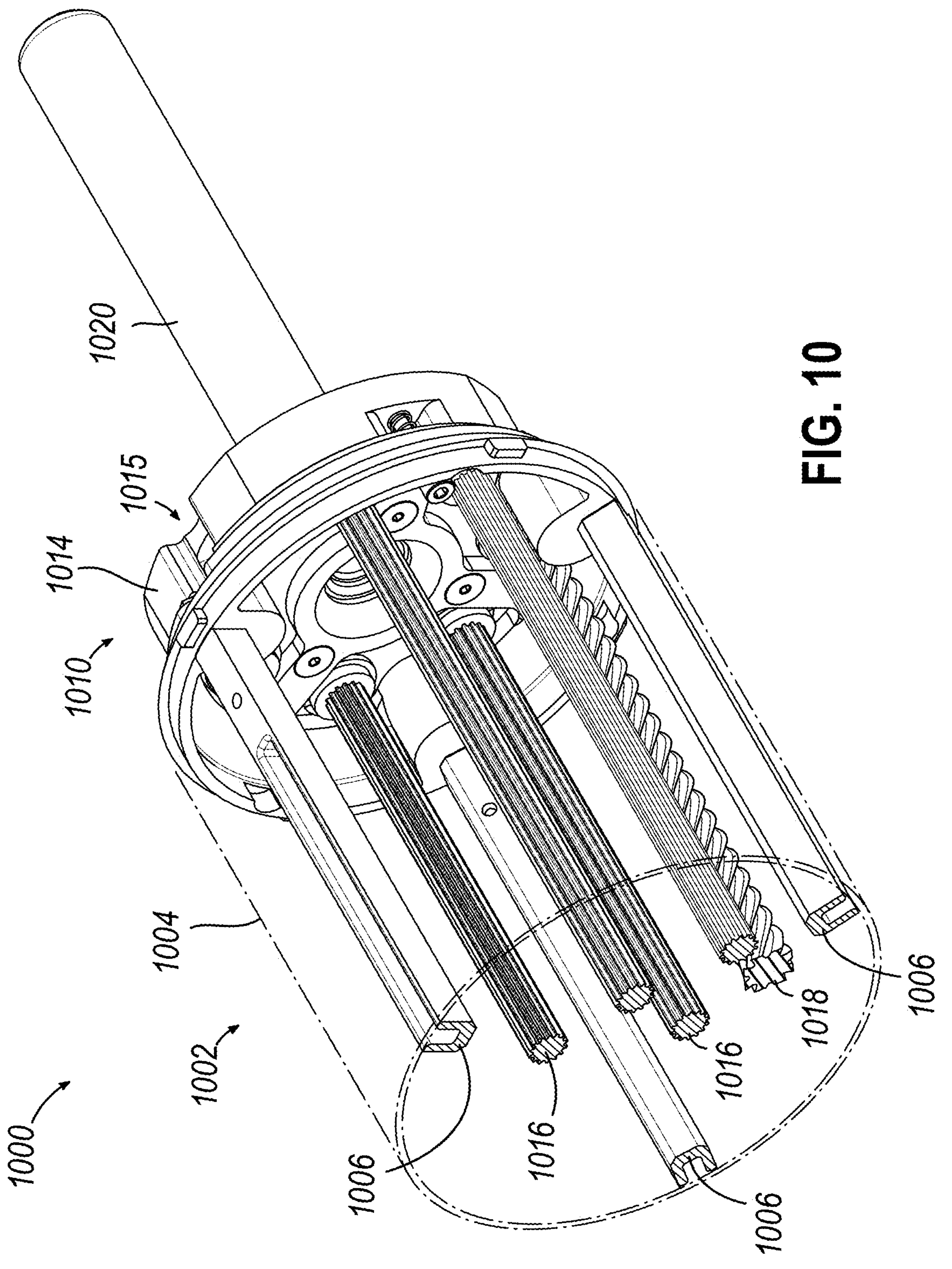
FIG. 10 depicts a sectional perspective view of the instrument base of FIG. 9 taken along section line 10-10 of FIG. 9, with selected portions being transparent for purposes of clarity.

FIGS. 9-10 show instrument base (1000). Instrument base (1000) includes a chassis housing (1002), an attachment interface (1010), and a distally extending sheath (1020). Chassis housing (1002) includes a cylindrical chamber (1004) dimensioned to slidably house a drive chassis (1034) (see FIG. 12) of shaft assembly (1032). While in the current example, chamber (1004) is cylindrically shaped, any other suitably shape may be used as would be apparent to one skilled in the art in view of the teachings herein.

As best shown in FIG. 10, chassis housing (1002) further includes three guide rails (1006) that are fixed to, and extend longitudinally along, an interior surface of cylindrical chamber (1004). Guide rails (1006) are dimensioned with fit within respective alignment channels (1105) (see FIG. 12) of each chassis plate (1104, 1106, 1108) (see FIG. 12) of drive chassis (1034) (see FIG. 12) while cylindrical chamber (1004) slidably houses drive chassis (1034) (see FIG. 12).

As will be described in greater detail below, drive chassis (1034) (see FIG. 12) is configured to actuate longitudinally within cylindrical chamber (1004) such that guide rails (1006) define a longitudinal path for drive chassis (1034) (see FIG. 12) to travel along. Additionally, as will be described in greater detail below, instrument base (1000) is configured to be rotated by a suitable rotational assembly of a suitable robotic arm (similar to rotational assembly (70) of robotic arm (32) described above), such that guide rails (1006) transmit rotational forces to drive chassis (1034) (see FIG. 12), the rest of shaft assembly (1032) (see FIG. 12), and end effector (1050) (see FIG. 12), thereby rotating surgical instrument (1030) (see FIG. 12) as a whole about longitudinal axis (LA) defined by a proximal portion (1036) (see FIG. 12) of shaft assembly (1032) (see FIG. 11A).

With respect to FIGS. 9-10, attachment interface (1010) is configured to couple instrument base (1000) with a suitable instrument driver, similar to instrument driver (66) described above. Attachment interface (1010) includes a plurality of drive inputs (1012), an interface plate (1014) defining a plurality of notches (1015), a plurality of elongated splined shafts (1016) extending proximally from respective drive inputs (1012) into the interior of cylindrical chamber (1004), and an elongated threaded rod (1018) extending proximally from a respective drive input (1012) into the interior of cylindrical chamber (1004).

Interface plate (1014) is fixed to both chassis housing (1002) and distally extending sheath (1020). Therefore, rotation of interface plate (1014) drives rotation of both chassis housing (1002) and distally extending sheath (1020). Notches (1015) are dimensioned to receive selected portions of a rotational assembly of a suitable robotic arm (similar to rotational assembly (70) of robotic arm (32) described above) such that the rotational assembly of the robotic arm may rotate interface plate (1014), chassis housing (1002), and distally extending sheath (1020) about longitudinal axis (LA) defined by a proximal portion (1036) (see FIG. 11A) of shaft assembly (1032) (see FIG. 11A).

Figure 12:
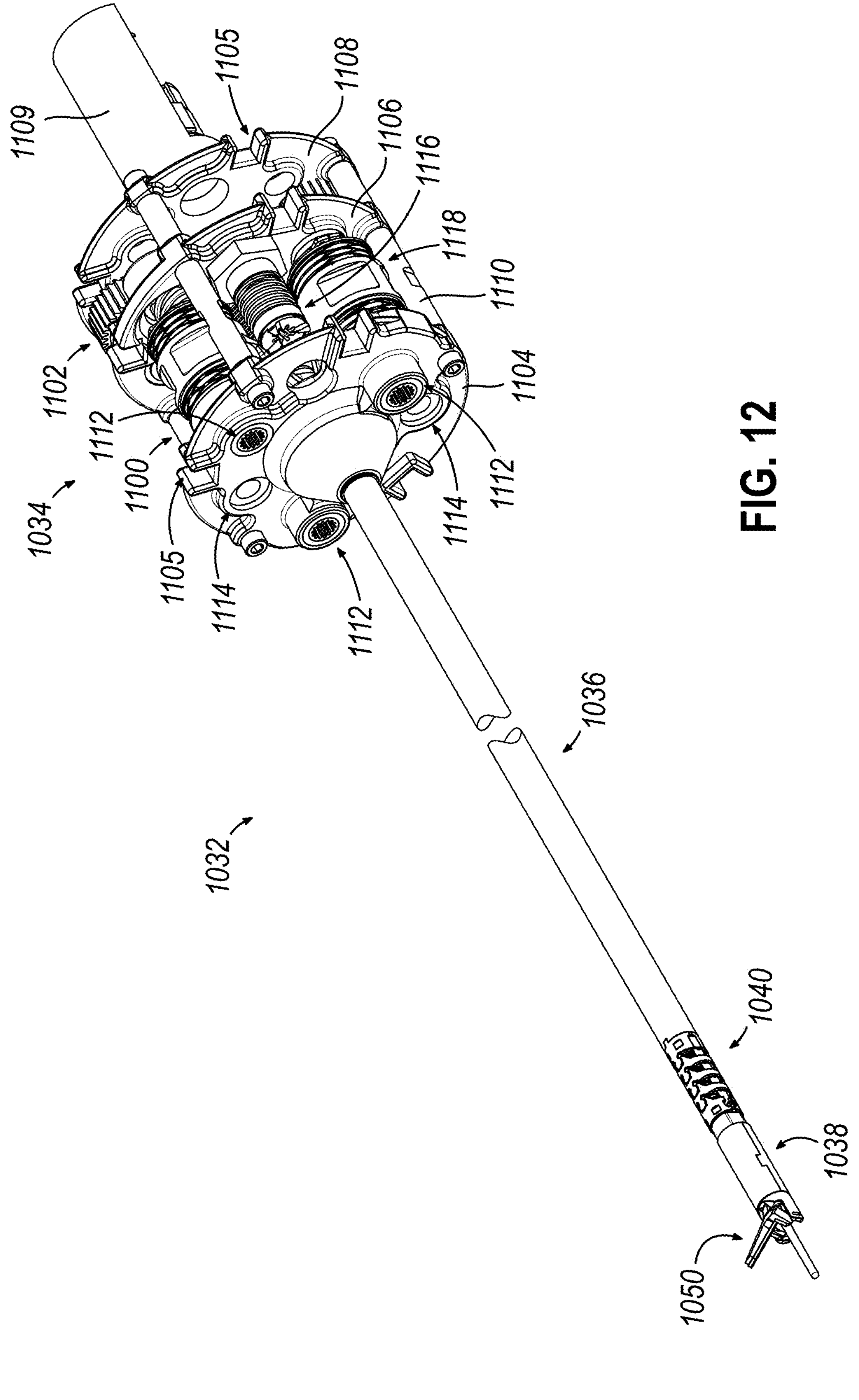
FIG. 12 depicts a perspective view of the shaft assembly and the end effector of FIG. 11A.

As mentioned above, guide rails (1006) are dimensioned with fit within respective alignment channels (1105) (see FIG. 12) of each chassis plate (1104, 1106, 1108) (see FIG. 12) of drive chassis (1034) (see FIG. 12). Therefore, rotation of interface plate (1014) via interaction with the rotational assembly (similar to rotational assembly (70) described above) of a suitable robotic arm is configured to drive rotation of the entire ultrasonic surgical instrument (1030) about longitudinal axis (LA) by transmitting rotational forces from instrument base (1000) to shaft assembly (1032) (see FIG. 11A) and end effector (1050) (see FIG. 11A) via guide rails (1006) and alignment channels (1105) (see FIG. 11A). In other words, rotation of interface plate (1014) caused by the rotational assembly of a suitable robotic arm (similar to rotational assembly (70) of robotic arm (32) described above) may provide the capability of end effector (1050) to roll about longitudinal axis (LA) in its entirety.

While interface plate (1014) mates with the rotational assembly of a suitable robotic arm via notches (1015), any other suitable features may be used to suitably couple interface plate (1014) and/or instrument base (1000) with the rotational assembly as would be apparent to one skilled in the art in view of the teachings herein.

Also, interface plate (1014) defines a central through hole such that the interior of distally extending sheath (1020) and chassis housing (1002) are in communication with each other via the central through hole of interface plate (1014). Therefore, a proximal shaft portion (1036) (see FIG. 12) of shaft assembly (1032) (see FIG. 12) may slidably extend from the interior of chassis housing (1002) through interface plate (1014) and distally extending sheath (1020). Distally extending sheath (1020) is dimensioned to slidably house selective portions of proximal shaft portion (1036).

Drive inputs (1012) are rotatably coupled with interface plate (1014) such that drive inputs (1012) may be independently rotated about their own axis relative to interface plate (1014). Drive inputs (1012) may be rotatably coupled with interface plate (1014) via any suitable features as would be apparent to one skilled in the art in view of the teachings herein, such as rotary bearings. Similar to drive inputs (80) described above, drive inputs (1012) are configured to respectively couple with corresponding drive outputs of a suitable robotic arm (similar to drive outputs (68) of robotic arm (32) described above). Therefore, drive outputs of a suitable robotic arm are configured to independently rotate drive inputs (1012) about their own axis relative to interface plate (1014).

It should be understood that drive inputs (1012) of the current example are distally presented on interface plate (1014) such that drive inputs of a suitable robotic arm (similar to drive outputs (68) of robotic arm (32) described above) would be proximally presented in order to suitably couple with drive inputs (1012). This feature is opposite to that showed in FIG. 5, where drive outputs (68) are distally presented and drive inputs (80) are proximally presented. Therefore, in the current example shown in FIGS. 9-11B, distally presented sheath (1020) would extend through a clearance bore of the instrument driver (similar to clearance bore (67) of instrument driver (66) described above) such that chassis housing (1002) would extend proximally from the instrument driver; while a distal end of distally extending sheath (1020) would extend distally from the instrument driver (similar to instrument driver (66) described above). Of course, this is merely optional, as drive inputs (1012) may be placed and presented at any other suitable location as would be apparent to one skilled in the art in view of the teachings herein.

Drive inputs (1012) are fixed to a respective elongated splined shaft (1016) or elongated threaded rod (1018) such that rotation of drive inputs (1012) leads to rotation of the respective elongated splined shaft (1016) or threaded rod (1018).

Splined shafts (1016) and threaded rod (1018) extend proximally from drive inputs (1012) into a proximal end of chassis housing (1002) along a respective longitudinal axis, where each respective longitudinal axis is parallel with longitudinal axis (LA) shown in further reference to FIG. 11A. Splined shafts (1016) and threaded rod (1018) are each rotatably supported by the proximal end of chassis housing (1002). Splined shafts (1016) and threaded rod (1018) may be rotatably supported by the proximal end of chassis housing (1002) via any suitable features as would be apparent to one skilled in the art in view of the teachings herein. For example, splined shafts (1016) and threaded rod (1018) may be coupled to proximal end of chassis housing (1002) via rotatory bearings.

Therefore, splined shafts (1016) and threaded rods (1018) are independently rotatable about their own longitudinal axis via interaction between respective drive inputs (1012) and corresponding drive outputs (similar to drive outputs (68) described above). As will be described in greater detail below, splined shaft (1016) and threaded rods (1018) may be suitably coupled to respective portions of drive chassis (1034) such that rotation of respective splined shafts (1016) and threaded rod (1018) drives actuation of shaft assembly (1032) and/or end effector (1050) in accordance with the description herein.

While in the current example, there are six drive inputs (1012), any suitable number of drive inputs (1012) may be used as would be apparent to one skilled in the art in view of the teachings herein. Also, in the current example, there are four splined shafts (1016), but any other suitable number of splined shafts (1016) may be used as would be apparent to one skilled in the art in view of the teachings herein.

B. Exemplary Articulating Shaft Assembly

FIGS. 12-17 and FIG. 22 show shaft assembly (1032) and end effector (1050) of ultrasonic surgical instrument (1030) (see FIG. 12). As best shown in FIG. 12, shaft assembly (1032) includes drive chassis (1034), proximal shaft portion (1036), articulation section (1040), and distal shaft portion (1038). Drive chassis (1034) is located on a proximal end of proximal shaft portion (1036). Proximal shaft portion (1036), articulation section (1040), and distal shaft portion (1038) may be substantially similar to proximal shaft portion (160), articulation section (164), and distal shaft portion (162) described above, respectively, with differences elaborated below.

Figure 13:
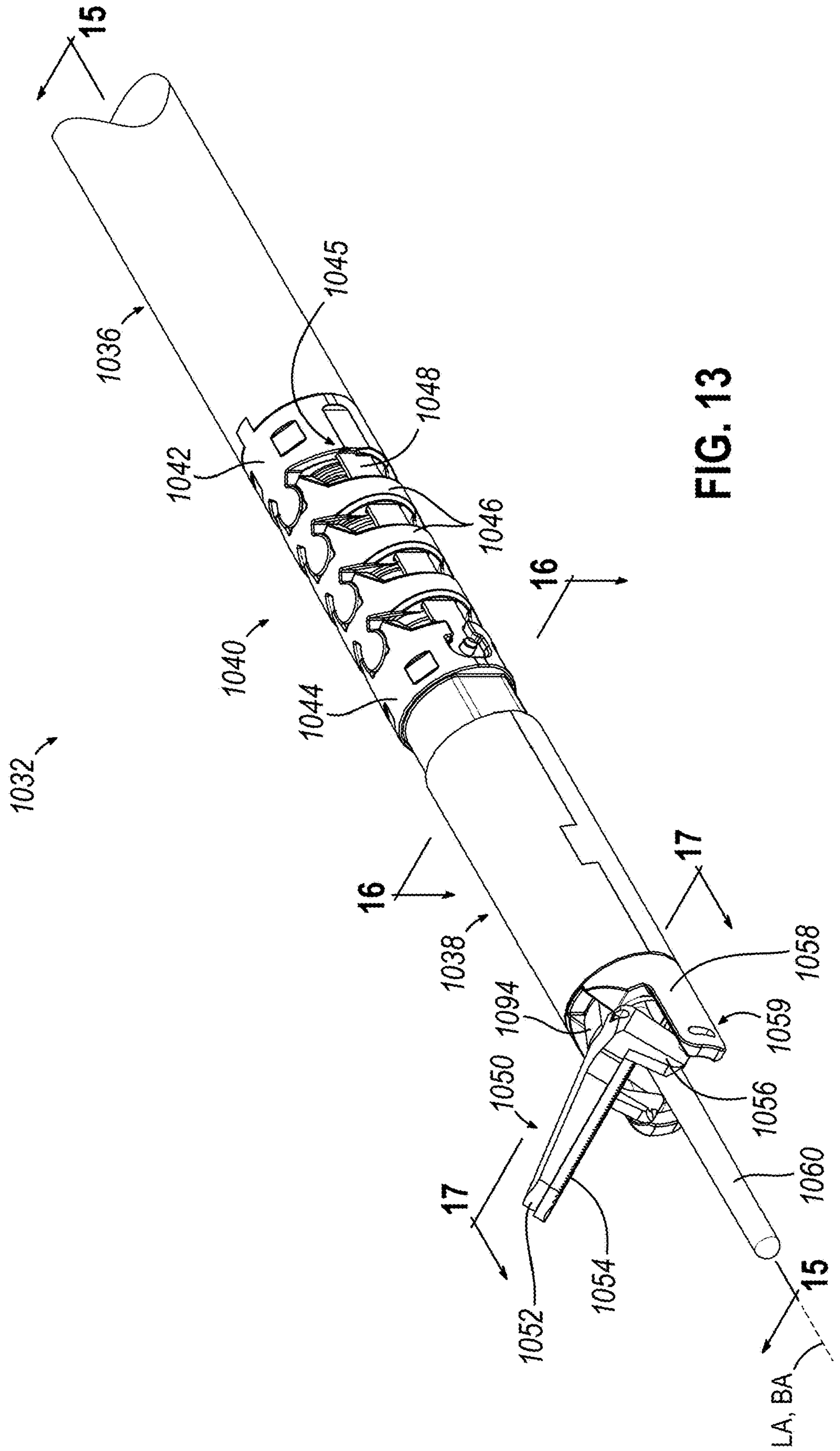
FIG. 13 depicts an enlarged perspective view of the distal end of the shaft assembly and the end effector of FIG. 11A.

Therefore, articulation section (1040) is configured to selectively position end effector (1050) at various lateral deflection angles relative to longitudinal axis (LA) defined by proximal shaft portion (1036). As best shown in FIG. 13, articulation section (1040) includes a proximal link (1042), a distal link (1044), a plurality of intermediate links (1046), and a pair of articulation bands (1048) extending through respective channels (1045); which are substantially similar to proximal link (168), distal link (170), intermediate links (172), articulation bands (174), and channels (176), respectively, described above. Therefore, articulation bands (1048) are configured to translate in an opposing fashion to drive bending of links (1042, 1044, 1046) to thereby laterally defect end effector (1050) away from longitudinal axis (LA) defined by proximal shaft portion (1036).

C. Exemplary Dual Roll End Effector

Figure 14:
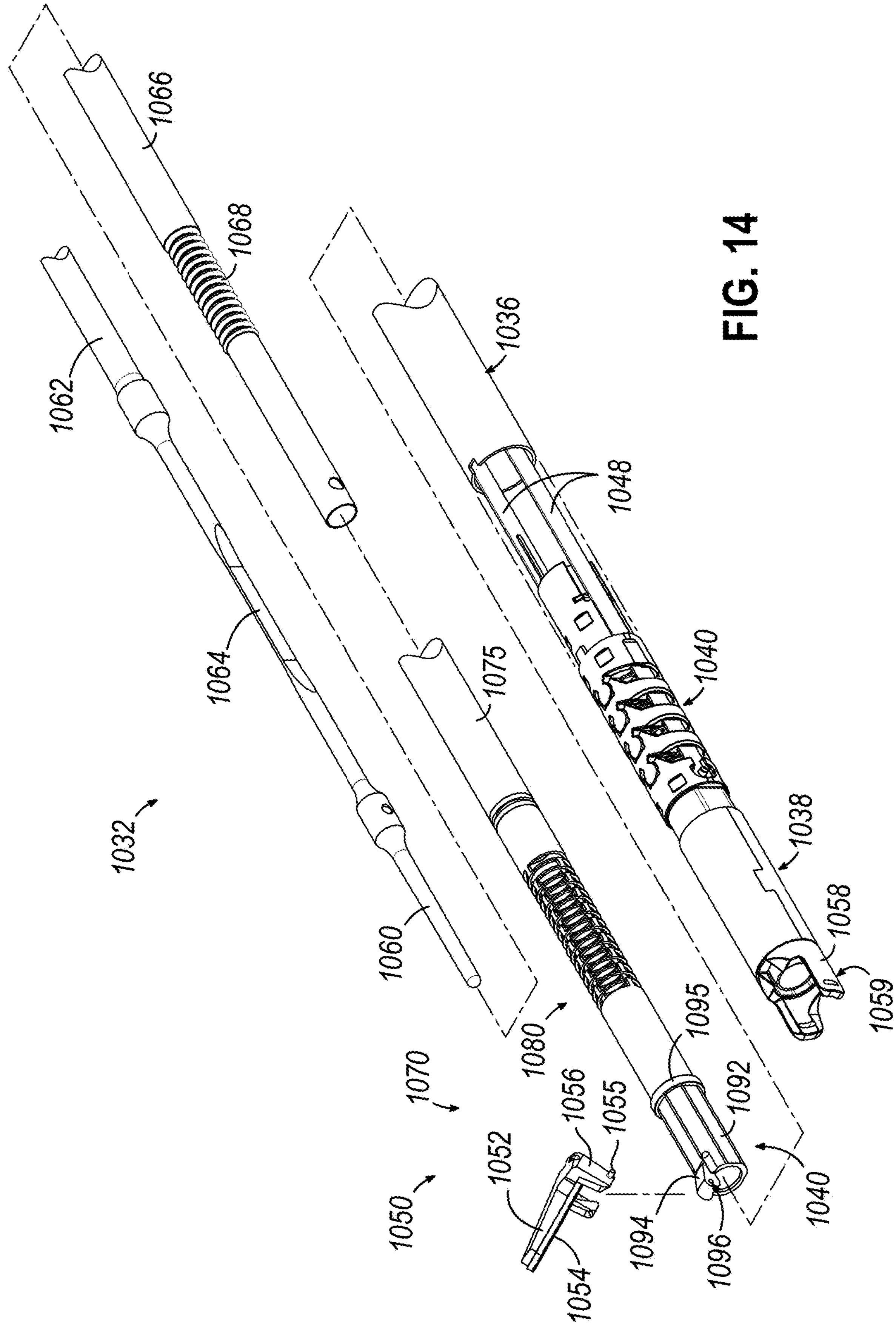
FIG. 14 depicts a partially exploded perspective view of the distal end of the shaft assembly and the end effector of FIG. 11A.
Figure 15:
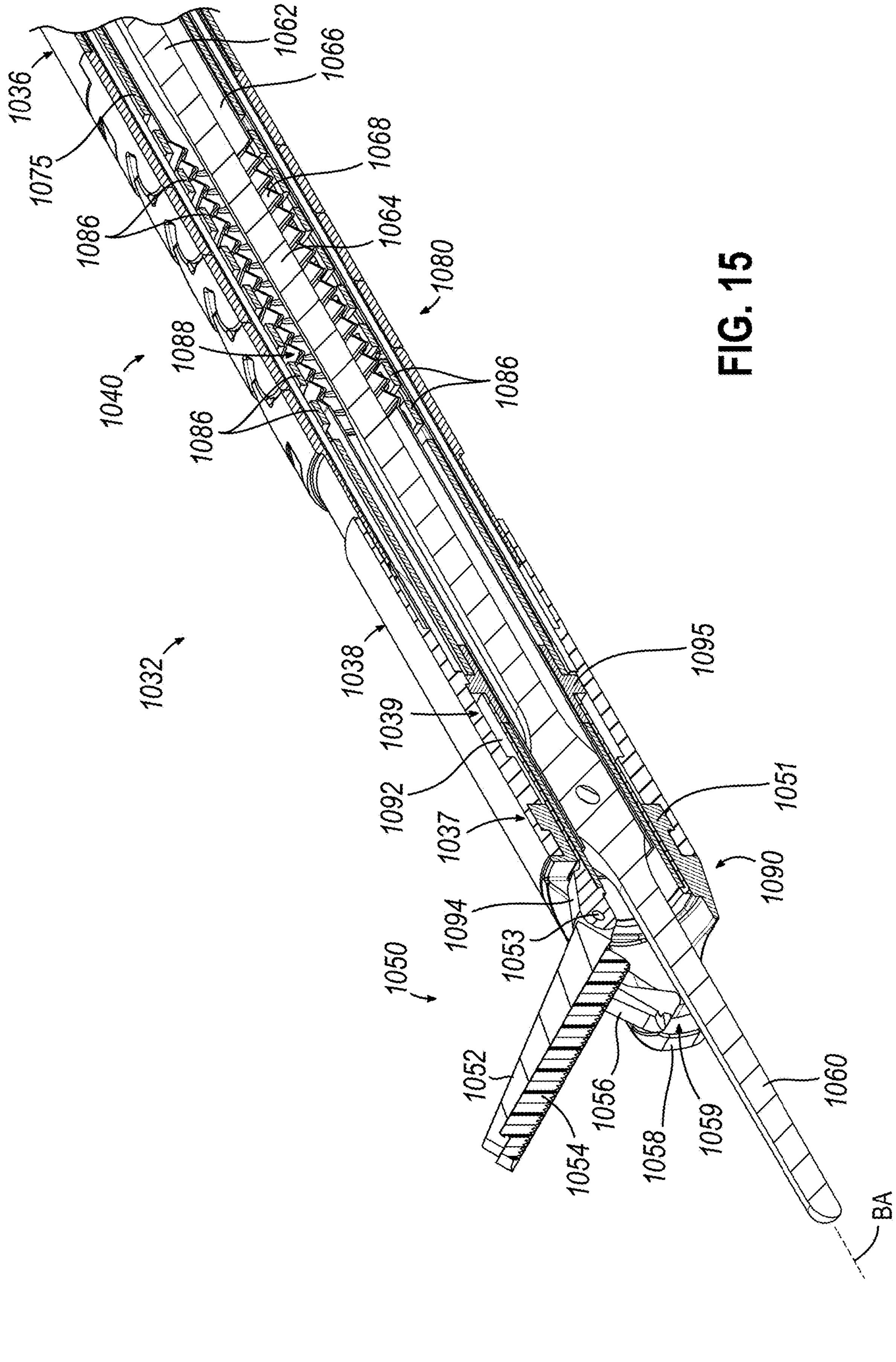
FIG. 15 depicts a sectional perspective view of the distal end of the shaft assembly and the end effector of FIG. 11A, taken along section line 15-15 of FIG. 13.
Figure 16:
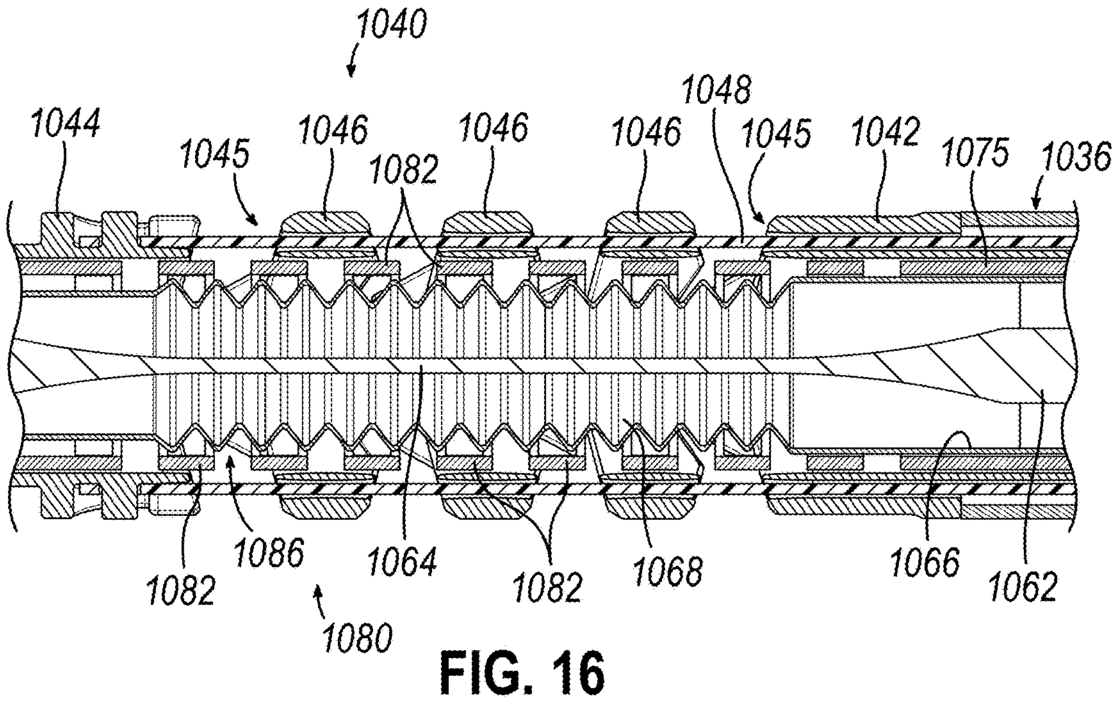
FIG. 16 depicts an enlarged cross-sectional view of an articulation section of the shaft assembly of FIG. 11A, taken along section line 16-16 of FIG. 13.

As shown in FIGS. 13-15, end effector (1050) includes an ultrasonic blade (1060) and a clamp arm (1052) having a clamp pad (1054) and a pair of arms (1056); which may be substantially similar to ultrasonic blade (146), clamp arm (144), clamp pad (148), and arms (151), respectively, with differences elaborated below.

As will be described in greater detail below, clamp arm (1052) may rotate relative to blade (1060) about a longitudinal axis (BA) defined by blade (1060) while end effector (1050) is articulated; while also maintaining the ability for clamp arm (1052) to selectively pivot toward and away from blade (1060) to selectively clamp tissue between clamp arm (1052) and blade (1060).

Blade (1060) of the present example is positioned at a distal end of an acoustic drivetrain. This acoustic drivetrain includes a transducer assembly (1065) (see FIGS. 23A-23D), and an acoustic waveguide (1062) having a flexible portion (1064); which may be substantially similar to transducer assembly (154), acoustic waveguide (156), and flexible portion (158), described above, respectively, with difference elaborated below.

As shown in FIGS. 14 and 15, acoustic waveguide (1062) in housed within a waveguide sheath (1066). Waveguide sheath (1066) includes a flexible portion (1068) configured to house corresponding flexible portion (1064) of waveguide (1062). Waveguide sheath (1066) may protect waveguide (1062) from exposure to and accumulation of various external matter during exemplary use. Additionally, flexible portion (1068) of waveguide sheath (1066) may protect flexible portion (1064) from coming into accidental contact with various other structures of instrument (1030) during exemplary use, such as flexible section (1080) of a clamp arm drive tube (1070).

Waveguide sheath (1066) and waveguide (1062) are housed within clamp arm drive tube (1070). Clamp arm drive tube (1070) is housed within corresponding portions of a distal shaft portion (1038), an articulation section (1040), and a proximal shaft portion (1036) of shaft assembly (1032).

As best seen in FIG. 14, clamp arm (1052) is pivotally coupled to a first tongue (1058) via vertical slots (1059) defined by first tongue (1058) and protrusions (1055) extending from arms (1056) of clamp arm (1052). Additionally, clamp arm (1052) is pivotally coupled to a second tongue (1094) via a pivot pin (1053) (see FIG. 15) extending through clamp arm (1052) and a pin hole (1096) of second tongue (1094). Relative movement between first tongue (1058) and second tongue (1094) drive clamp arm (1052) to pivot between an open position (see FIG. 24C) and a closed position (see FIG. 24D) relative to blade (1060). As will be described in greater detail below, first tongue (1058) and second tongue (1094) are configured to rotate about axis (BA) defined by blade (1060) in order to roll clamp arm (1052) relative to blade (1060) into various rotational positions about axis (BA).

In the current example, and as best shown in FIG. 15, a proximal flange (1051) of first tongue (1058) is housed within a first interior annular recess (1037) defined by distal shaft portion (1038) such that first tongue (1058) is rotationally disposed within distal shaft portion (1038) while remaining longitudinally fixed relative to distal shaft portion (1038). In other words, first tongue (1058) is configured to freely rotate relative to distal shaft portion (1038) and blade (1060) about axis (BA), while remaining substantially longitudinally constrained relative to distal shaft portion (1038).

Referring back to FIG. 14, second tongue (1094) forms a portion of clamp arm coupling (1090) of clamp arm drive tube (1070). Clamp arm coupling (1090) also includes a plurality of flat surfaces (1092) and a flange (1095). Clamp arm coupling (1090) is slidably disposed within the interior of first tongue (1058) such that clamp arm coupling (1090) may translate relative to first tongue (1058) in order to open and close clamp arm (1052) relative to blade (1060) in accordance with the description herein.

As best shown in FIG. 15, flange (1095) is slidably and rotatably disposed within a second interior annular recess (1039) of distal shaft portion (1038) such that clamp arm coupling (1090) may rotate and translate relative to distal shaft portion (1038) in accordance with the description herein without accidentally decoupling from distal shaft portion (1038). Therefore, clamp arm coupling (1090) may rotate relative to blade (1060) and distal shaft portion (1038) about longitudinal axis (BA) defined by blade (1060). Additionally, clamp arm coupling (1090) may translate relative to distal shaft portion (1038) along a path defined by the longitudinal length of second interior annular recess (1039).

Figure 17:
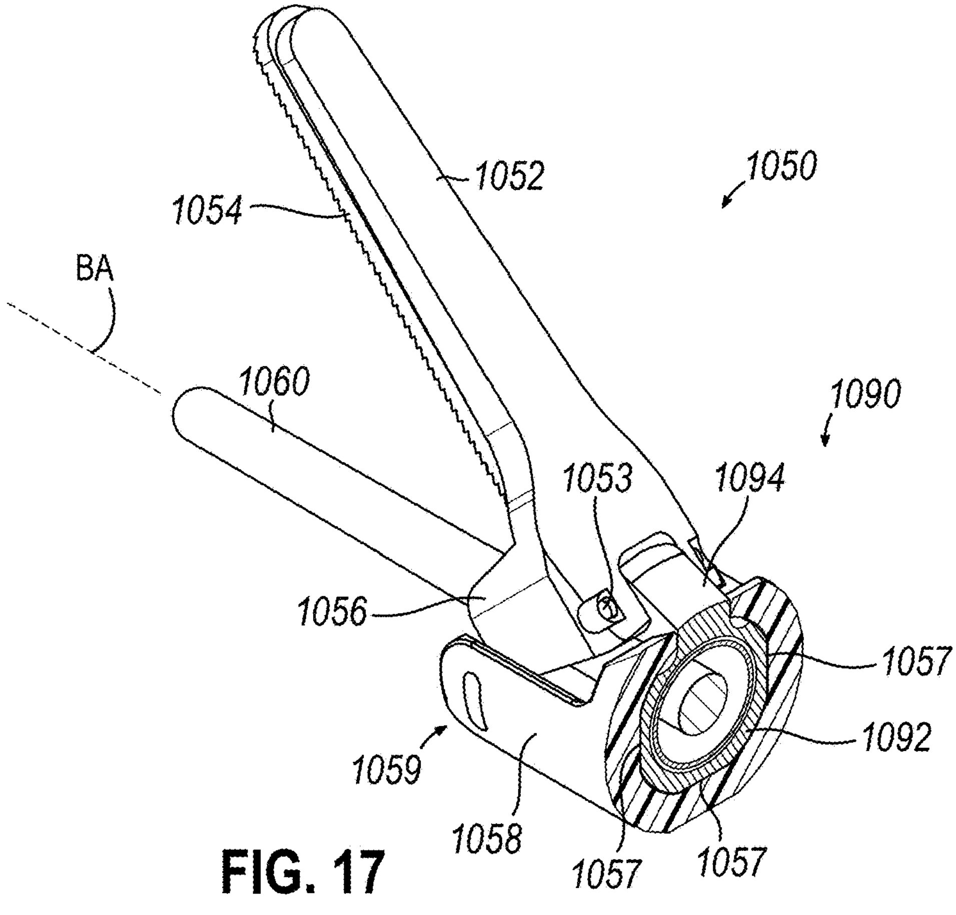
FIG. 17 depicts a sectional view of the end effector of FIG. 11A, taken along section line 17-17 of FIG. 13.

With respect to FIG. 15 and FIG. 17, flat surfaces (1092) of clamp arm coupling (1090) abut against corresponding flat surfaces (1057) of first tongue (1058) defining the channel slidably housing clamp arm coupling (1090). As mentioned above, first tongue (1058) is rotationally disposed within an annular recess (1037) of distal shaft portion (1038). Flat surfaces (1092) of clamp arm coupling (1090) are suitably engaged with corresponding flat surfaces (1057) of clamp arm coupling (1090) such that rotation of clamp arm coupling (1090) relative to blade (1060) and distal shaft portion (1038) about longitudinal axis (BA) also drives rotation first tongue (1058) relative to blade (1060) and distal shaft portion (1038) about axis (BA).

Therefore, flat surfaces (1092, 1057) are configured to allow clamp arm coupling (1090) to translate relative to first tongue (1058) in order to open and close clamp arm (1052) relative to blade (1060), while also allowing clamp arm coupling (1090) to rotate first tongue (1058) about longitudinal axis (BA) relative to blade (1060) and distal shaft portion (1038). Since clamp arm (1052) is coupled to both first tongue (1058) and clamp arm coupling (1090), rotation of first tongue (1058) and clamp arm coupling (1090) about longtail axis (BA) relative to blade (1060) also drives rotation of clamp arm (1052) and clamp pad (1054) about longitudinal axis (BA) relative to blade (1060) (i.e. rolling clamp arm (1052) relative to blade (1060) about axis (BA)).

It should be understood that while in the current example, second tongue (1094) forms a portion of clamp arm coupling (1090), this is merely optional. In some instances, first tongue (1058) forms a portion of clamp arm coupling (1090) such that first tongue (1058) actuates with clamp arm drive tube (1070) in accordance with the description herein; while second tongue (1094) remains longitudinally fixed, yet rotationally coupled to distal shaft portion (1038).

D. Exemplary Clamp Arm Drive Tube

FIGS. 18-21 show clamp arm drive tube (1070). Clamp arm drive tube (1070) is configured to drive rotation and translation of clamp arm coupling (1090) in accordance with the description herein while end effector is in a straight configuration, or any suitable articulated configuration. Therefore, clamp arm drive tube (1070) is configured to drive translation of clamp arm coupling (1090) in order to open and close clamp arm (1052) relative to blade (1060). Additionally, clamp arm drive tube (1070) is configured to rotate clamp arm coupling (1090) in order to drive rotation of clamp arm (1052) and clamp pad (1054) about longitudinal axis (BA) relative to blade (1060) (i.e. rolling clamp arm (1052) relative to blade (1060) about axis (BA)). Further, clamp arm drive tube (1070) is configured to drive translation and rotation of clamp arm coupling (1090) while end effector (1050) is in a straight configuration or any suitable articulated configuration.

Figure 18:
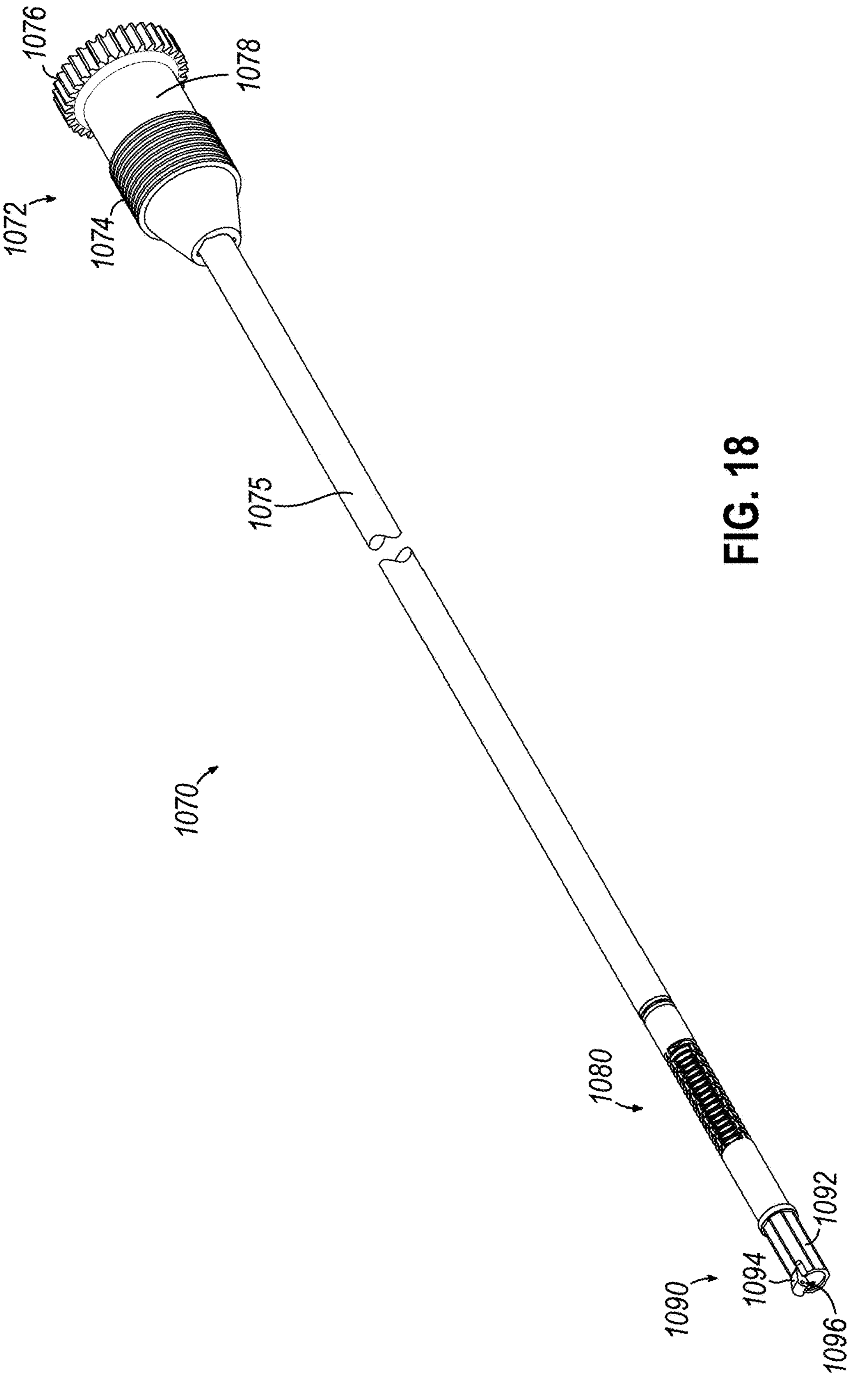
FIG. 18 depicts a perspective view of an exemplary clamp arm drive tube of the shaft assembly and the end effector of FIG. 11A.
Figure 19:
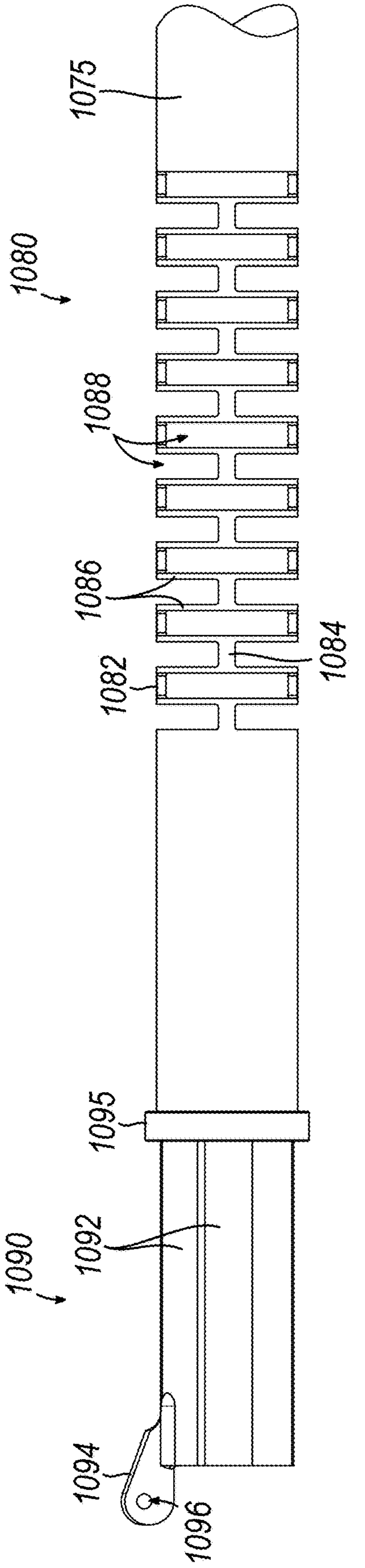
FIG. 19 depicts an elevation side view of a flexible section and a clamp arm coupling of the clamp arm drive tube of FIG. 18.
Figure 20:
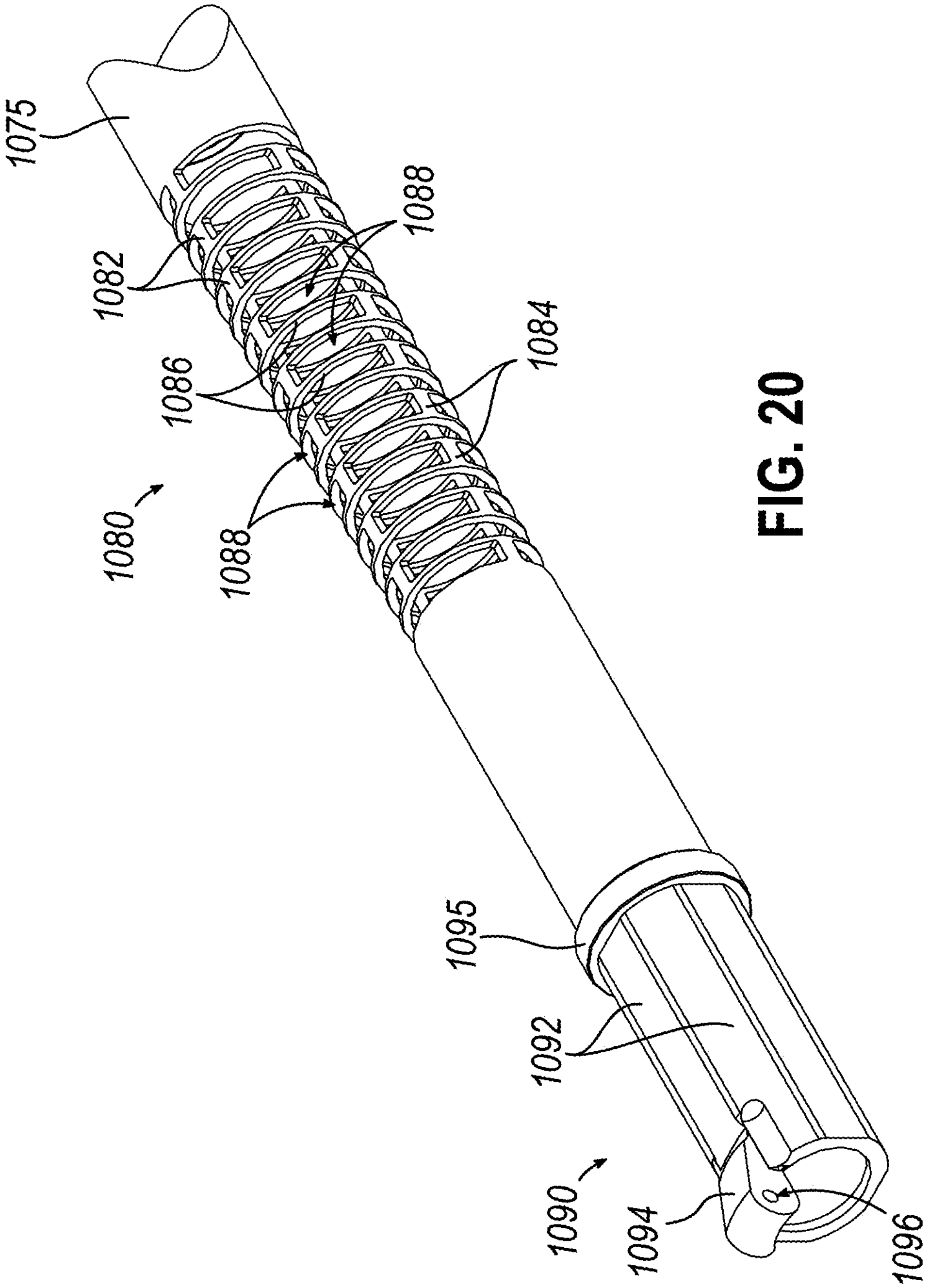
FIG. 20 depicts a perspective view of the flexible section and the clamp arm coupling of FIG. 19.
Figure 21:
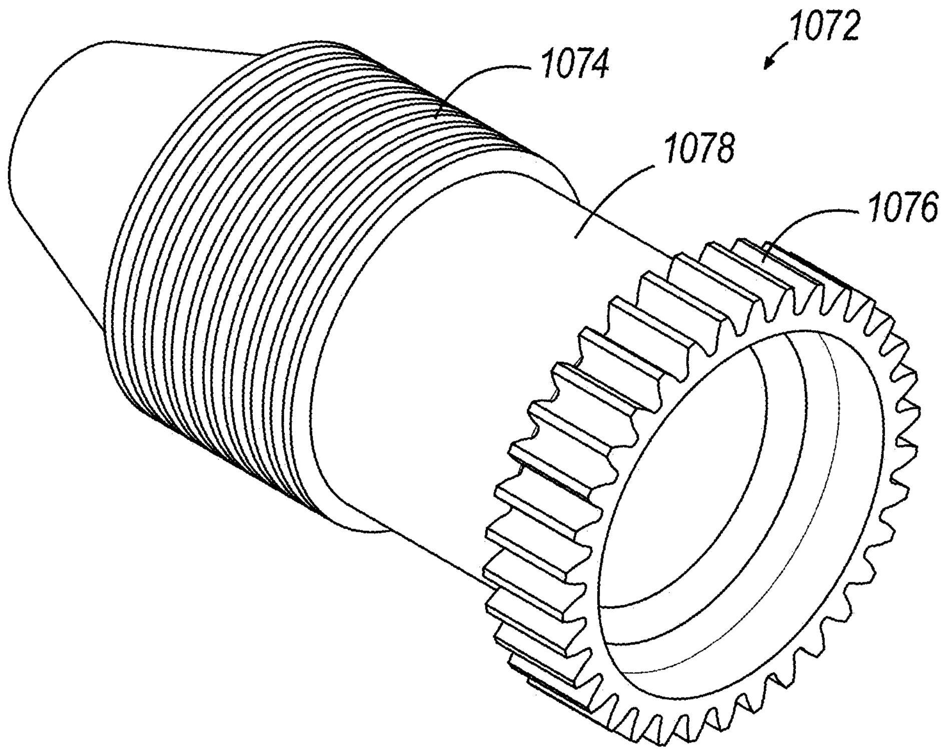
FIG. 21 depicts a perspective view of a proximal end of the clamp arm drive tube of FIG. 18.

Clamp arm drive tube (1070) includes a proximal end (1072), an elongated intermediate portion (1075), a flexible section (1080), and clamp arm coupling (1090). Clamp arm drive tube (1070) defines a central channel extending from an open proximal end to an open distal end, in order to house various components of instrument (1030), as exemplified in FIGS. 15-16. As shown in FIGS. 18 and 21, proximal end (1072) includes a tubular body (1078), a circular rack (1074) disposed on an outer surface of tubular body (1078), and a rotation gear (1076) disposed on a proximal end of tubular body (1078).

Proximal end (1072) is housed within a proximal drive section (1102) (see FIG. 22) of drive chassis (1043). As will be described in greater detail below, circular rack (1074) is dimensioned to mesh with suitable components of a clamp arm closure drive assembly (1120) (see FIG. 23A) of proximal drive section (1102) (see FIG. 23A) such that clamp arm closure drive assembly (1120) (see FIG. 23A) is configured to drive translation of clamp arm drive tube (1070), thereby driving clamp arm (1052) between the open configuration and the closed configuration. As will also be described in greater detail below, rotation gear (1076) is dimensioned to mesh with suitable components of clamp arm rotary drive assembly (1140) (see FIG. 23A) of proximal drive section (1102) (see FIG. 23A) such that clamp arm rotary drive assembly (1140) (see FIG. 23A) is configured to drive rotation of clamp arm drive tube (1070), thereby rolling clamp arm (1052) (see FIG. 23A) about axis (BA) relative to blade (1060) (see FIG. 23A).

Elongated intermediate portion (1075) extends between proximal end (1072) and flexible section (1080). Intermediate portion (1075) is sufficiently rigid to suitably transmit rotational and translational forces from proximal end (1072) to flexible section (1080).

Referring back to FIGS. 15-16, flexible section (1080) is housed between flexible portion (1068) of waveguide sheath (1066) and links (1042, 1044, 1046) of articulation section (1040). Flexible section (1080) defines a tubular passageway housing flexible portion (1068) of waveguide sheath (1066). Flexible section (1080) is configured to rotate and translate relative to flexible portion (1068) of waveguide sheath (1066) and links (1042, 1044, 1046) of articulation section (1040), regardless of whether articulation section (1040) is straight (as exemplified in FIG. 16) or bent to suitably articulate end effector (1050) (see FIG. 17).

In the current example shown in FIGS. 16-20, flexible section (1080) includes a first plurality of longitudinal connecting members (1082), a second plurality of longitudinal connecting members (1084), and a plurality of circumferential connecting members (1086) that together define a multitude of gaps (1088) to promote connecting members (1082, 1084, 1086) to flex toward and away from each other. To this end, each longitudinal section of connecting members (1082, 1084) include a pair of connecting members (1082, 1084) that are angularly offset from each other 180 degrees in order to partially define the tubular passageway housing waveguide sheath (1066). Longitudinal connecting members (1082, 1084) extend from intermediate portion (1075) toward clamp arm coupling (1090) in an alternating fashion. Additionally, the first plurality of longitudinal connecting members (1082) and the second plurality of longitudinal connecting members (1084) are angularly offset from each other by 90 degrees. Circumferential connecting members (1086) couple the first plurality of longitudinal connecting members (1082) with directly adjacent second plurality of connecting members (1084). Circumferential connecting members (1086) also partially defining the tubular passageway housing waveguide sheath (1066).

Connecting members (1082, 1084, 1086) are sufficiently flexible such that connecting members (1082, 1084, 1086) allow flexible section (1080) to bend in response articulation section (1040) bending to deflect end effector (1050) in accordance with the description herein. Flexible section (1080) may bend due to contact with flexible portion (1068) of waveguide sheath (1066) and/or contact with the internal surfaces of links (1042, 1044, 1046) of articulation section (1040). In some instances, connecting members (1082, 1084, 1086) may also be sufficiently resilient toward the position associated with end effector (1050) being in the straight configuration.

In addition to being sufficiently flexible to bend in response to bending of articulation section (1040), connecting members (1082, 1084, 1086) are sufficiently rigid to suitably transmit torque from proximal end (1072) to clamp arm coupling (1090) to thereby rotate clamp arm coupling (1090) relative to distal shaft portion (1038) in accordance with the description herein. Further, connecting members (1082, 1084, 1086) are sufficiently rigid to transmit such torque regardless of whether articulation section (1040) is straight (as exemplified in FIG. 16) or bent to suitably articulate end effector (1050).

Connecting members (1082, 1084, 1086) are also sufficiently rigid to suitably transmit translational forces to clamp arm coupling (1090) to drive the opening and closing of clamp arm (1052) relative to blade (1060) in accordance with the description herein. Similarly, connecting members (1082, 1084, 1086) are sufficiently rigid to transmit such translational forces regardless of whether articulation section (1040) is straight (as exemplified in FIG. 16) or bent to suitably articulate end effector (1050).

Flexible section (1080) may be formed from any suitable material as would be apparent to one skilled in the art in view of the teachings herein. In the present example, are collectively formed together such that flexible section (1080) is singularly and unitarily formed from a distal end thereof to a proximal end thereof. For instances, flexible section (1080) may be formed of nitinol.

While longitudinally extending connecting members (1082, 1084) are generally linearly shaped and circumferentially extending connecting members (1086) are generally annularly shaped in the current example, connecting members may have any suitable geometry as would be apparent to one skilled in the art in view of the teachings herein. For instance, connecting members may extend diagonally while defining a tubular opening, connecting members may form a cross-hatch pattern, connecting members may form a braided pattern, etc.

E. Exemplary Drive Chassis of Articulating Shaft Assembly

As mentioned above with respect to FIGS. 9, 10, 22 and 23A, drive chassis (1034) is configured to be slidably housed within chassis housing (1002) of instrument base (1000). As also mentioned above, and as will be described in greater detail below, drive chassis (1034) is configured to slidably attach to splined shafts (1016) and receive threaded rod (1018) such that rotation of splined shaft (1016) and threaded rod (1018) drives actuation of shaft assembly (1032) and/or end effector (1050).

Figure 22:
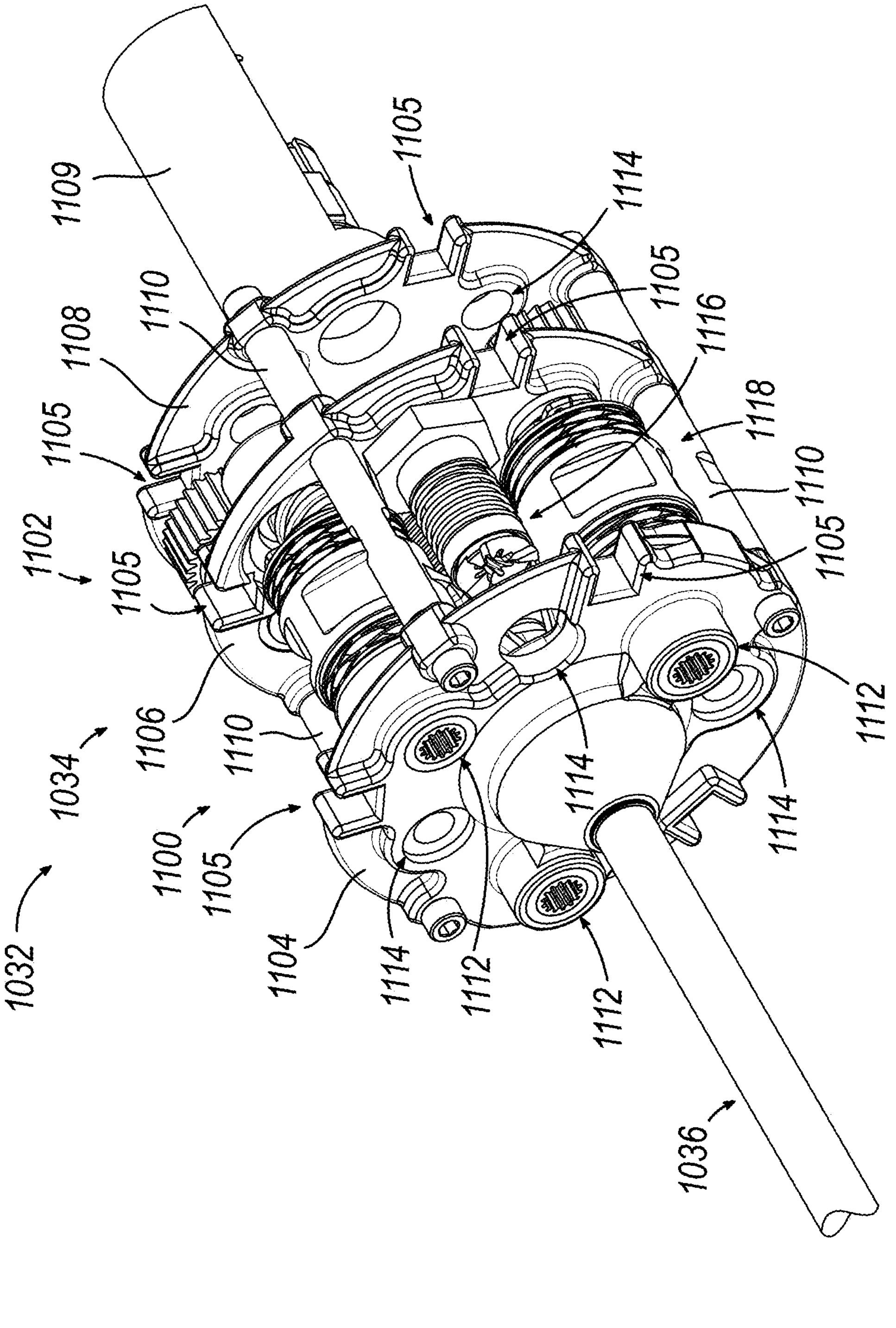
FIG. 22 depicts a perspective view of a drive chassis of the shaft assembly of FIG. 11A, where the drive chassis includes a proximal drive section and a distal drive section.

Drive chassis (1034) shown in FIG. 22 includes a distal drive section (1100), a proximal drive section (1102), distal chassis plate (1104), intermediate chassis plate (1106), proximal chassis plate (1108), and a transducer sheath (1109) extending proximally from proximal chassis plate (1108). Chassis plates (1104, 1106, 1108) are fixed to each other via coupling members (1110). Therefore, chassis plates (1104, 1106, 1108) act as a mechanical frame for distal drive section (1100) and proximal drive section (1102). As mentioned above, chassis plates (1104, 1106, 1108) define channels (1105) dimensioned to receive guide rails (1006) (see FIG. 10) of chassis housing (1002) (see FIG. 10).

Each chassis plate (1104, 1106, 1108) also defines a plurality of openings (1114). Openings (1114) of individual chassis plates (1104, 1106, 1108) are aligned with corresponding openings (1114) of other chassis plates (1104, 1106, 1108) along an axis that extends parallel with longitudinal axis (LA) of proximal shaft portion (1036). Aligned openings (1114) are associated with a drive assembly (1116, 1118, 1120, 1140) and dimensioned to receive either splined shaft (1016) (see FIG. 10) or threaded rod (1018) (see FIG. 10) such that the received splined shaft (1016) (see FIG. 10) or threaded rod (1018) (see FIG. 10) suitably interacts with the corresponding drive assembly (1116, 1118, 1120, 1140) in accordance with the description herein.

Distal drive section (1100) is housed between distal chassis plate (1104) and intermediate chassis plate (1106). Distal drive section (1100) includes linear drive assembly (1116) and a pair of articulation drive assemblies (1118). Linear drive assembly (1116) is fixed to intermediate plate (1106) and includes an internal female threading configured to mesh the with threading of threaded rod (1018) (see FIG. 10). Since the internal female threading of linear drive assembly (1116) is fixed to intermediate plate (1106), and intermediate plate (1106) is rotationally constrained within chassis housing (1002) (see FIG. 10), rotation of threaded rod (1018) (see FIG. 10) in accordance with the description herein drives linear actuation of drive chassis (1034), the rest of shaft assembly (1032) (see FIG. 11A), and end effector (1050) (see FIG. 11A) relative to chassis housing (1002) (see FIG. 11A) and distally extending sheath (1020) (see FIG. 11A). Therefore, rotation of threaded rod (1018) (see FIG. 10), while coupled with linear drive assembly (1116), may actuate end effector (1050) (see FIG. 11A) relative to chassis housing (1002) (see FIG. 11A) between a proximal position (see FIG. 11A) and a distal position (see FIG. 11B).

Each articulation drive assembly (1118) comprises an internal splined rotary body (1112) dimensioned to slidably receive a corresponding splined shaft (1016), thereby promoting the slidably coupled nature of drive chassis (1034) (see FIG. 11A) and chassis housing (1002) (see FIG. 11A). Internal splined rotary bodies (1112) are rotationally supported to a suitable chassis plate (1104, 1106, 1108). In the current example, internal splined rotary bodies (1112) are rotationally supported by distal chassis plate (1104). Each articulation drive assembly (1118) is coupled to a corresponding articulation band (1048). Articulation drive assemblies (1118) are configured to convert rotational motion of a corresponding splined shaft (1016) into linear motion of articulation bands (1048) in order to bend articulation section (1040) in accordance with the description herein. Articulation drive assemblies (1118) may have any suitable components as would be apparent to one skilled in the art in view of the teachings herein.

Proximal drive section (1102) is housed between proximal chassis plate (1108) and intermediate chassis plate (1106). As best shown in FIGS. 23A-23D, proximal drive section (1102) includes a clamp arm closure drive assembly (1120) and a clamp arm rotary drive assembly (1140). As will be described in greater detail below, clamp arm closure drive assembly (1120) is configured to mesh with circular rack (1074) of clamp arm drive tube (1070) in order to drive translation of clamp arm drive tube (1070), thereby driving clamp arm (1052) (see FIG. 13) between the open configuration and the closed configuration. As will also be described in greater detail below, clamp arm rotary drive assembly (1140) is configured to mesh with rotation gear (1076) of clamp arm drive tube (1070) in order to drive rotation of clamp arm drive tube (1070), thereby driving rotation of clamp arm (1052) (see FIG. 13) about longitudinal axis (BA) of blade (1060) (see FIG. 13) into any suitable roll position relative to blade (1060) (see FIG. 13).

With continued reference to FIGS. 23A-23D, clamp arm closure drive assembly (1120) includes a first gear member (1122) rotatable about a first drive axis (DA1), and a second gear member (1130) rotatable about a second drive axis (DA2). First gear member (1122) includes an internal splined rotary body (1124), a shaft (1126), and helical, forty-five-degree gear teeth (1128). Internal splined rotary body (1124) may be substantially similar to internal splined rotary body (1112) described above. Therefore, internal splined rotary body (1124) is dimensioned to slidably receive a corresponding splined shaft (1016), thereby promoting the slidably coupled nature of drive chassis (1034) and chassis housing (1002) (see FIG. 10). Internal splined rotary body (1124) is rotationally supported to a suitable chassis plate (1104, 1106, 1108) such that first gear member (1122) actuates with drive chassis (1034), but also such that first gear member (1122) may rotate relative to drive chassis (1034) about drive axis (DA1). Rotary body (1124) is fixed to the rest of first gear member (1122) such that rotation of rotary body (1124) about drive axis (DA1) directly drives rotation of shaft (1126) and gear teeth (1128). Therefore, rotation of corresponding splined shaft (1016) about drive axis (DA1) drives rotation of first gear member (1122).

Shaft (1126) defines a channel dimensioned to accommodate the corresponding splined shaft (1016) (see FIG. 10). Gear teeth (1128) are dimensioned to mesh with gear teeth (1138) of second gear member (1130) such that rotation of first gear member (1122) about drive axis (DA1) drives rotation of second gear member (1130) about drives axis (DA2).

Second gear member (1130) includes a pinion gear (1132), a shaft (1136), and helical, forty-five-degree gear teeth (1138). Shaft (1136) couples pinion gear (1132) with gear teeth (1138). As mentioned above, second gear member (1130) is rotatable about drive axis (DA2). Further, second gear member (1130) is rotationally supported to a suitable chassis plate (1104, 1106, 1108) such that first gear member (1122) actuates with drive chassis (1034), but also such that first gear member (1122) may rotate relative to drive chassis (1034) about drive axis (DA2).

Complementary gear teeth (1128, 1138) suitably mesh with each other such that rotation of first gear member (1122) in a first angular direction about drive axis (DA1) drives rotation of second gear member (1130) in a first angular direction about drive axis (DA2). Additionally, rotation of first gear member (1122) in a second, opposite, angular direction about drive axis (DA1) drives rotation of second gear member (1130) in a second, opposite, angular direction about drive axis (DA2). Drive axes (DA1, DA2) are perpendicular with each other.

Pinion gear (1132) meshes with circular rack (1074) such that rotation of pinion gear (1132) in the first angular direction about drive axis (DA2) drives distal translation of circular rack (1074) along drive axis (DA3), and therefore the rest of clamp arm drive tube (1070). Conversely, rotation of pinion gear (1132) in the second, opposite, angular direction about drive axis (DA2) drives proximal translation of circular rack (1074) along drive axis (DA3), and therefore the rest of clamp arm drive tube (1070). As mentioned above, translation of drive tube (1070) is configured to open and close clamp arm (1052) (see FIG. 13) relative to blade (1060) (see FIG. 13). Therefore, clamp arm closure drive assembly (1120) may open and close clamp arm (1052) depending on the angular direction first gear member (1122) and second gear member (1130) rotate. Pinion gear (1132) is configured to mesh with circular rack (1074) regardless of the angular position of circular rack (1074) about longitudinal axis (LA).

Clamp arm rotary drive assembly (1140) includes a gear member (1142) rotatable about rotary axis (R1). Gear member (1142) includes an internal splined rotary body (1144), a shaft (1146), and gear teeth (1148). Internal splined rotary body (1144) may be substantially similar to internal splined rotary body (1112) described above. Therefore, internal splined rotary body (1144) is dimensioned to slidably receive a corresponding splined shaft (1016) (see FIG. 13) (see FIG. 10), thereby promoting the slidably coupled nature of drive chassis (1034) and chassis housing (1002) (see FIG. 10). Internal splined rotary body (1144) is rotationally supported to a suitable chassis plate (1104, 1106, 1108) such that gear member (1142) actuates with drive chassis (1034) and also such that gear member (1142) may rotate relative to drive chassis (1034) about rotary axis (R1). Rotary body (1144) is fixed to the rest of gear member (1142) such that rotation of rotary body (1144) about rotary axis (R1) directly drives rotation of shaft (1146) and gear teeth (1148). Therefore, rotation of corresponding splined shaft (1016) about rotary axis (R1) drives rotation of gear member (1142).

Shaft (1146) defines a channel dimensioned to accommodate the corresponding splined shaft (1016) (see FIG. 10). Gear teeth (1148) are dimensioned to mesh with rotation gear (1076) such that rotation of gear member (1142) about rotary axis (R1) drives rotation of tubular body (1078) and elongated intermediate portion (1075) about rotary axis (R2). Therefore, rotation of gear member (1142) in a first angular direction about rotary axis (R1) drives rotation of tubular body (1078) and elongated intermediate portion (1075) in a second, opposite, angular direction about rotary axis (R2). Conversely, rotation of gear member (1142) in the second angular direction about rotary ais (R1) drives rotation of tubular body (1078) and elongated intermediate portion (1075) in the first, opposite, angular direction about rotary axis (R2).

As mentioned above, rotation of drive tube (1070) is configured to drive rotation of clamp arm (1052) (see FIG. 13) about longitudinal axis (BA) of blade (1060) (see FIG. 13) into any suitable roll position relative to blade (1060) (see FIG. 13). Therefore, rotation of gear member (1142) about rotary axis (R1) is configured to drive rotation of clamp arm (1052) (see FIG. 13) about longitudinal axis (BA) of blade (1060).

It should be understood that gear teeth (1148) extend a sufficient length along a longitudinal path such that teeth (1148) and rotation gear (1076) still suitably engage each other, even as drive tube (1070) longitudinally translates along axis (DA3) in order to suitably open and close clamp arm (1052) in accordance with the description herein.

F. Exemplary Use of Dual Roll End Effector

FIG. 11A in conjunction with FIGS. 23A-24D—show an exemplary use of distal drive section (1100), proximal drive section (1102), and clamp arm drive tube (1070) in order to articulate end effector (1050), roll clamp arm (1052) about the longitudinal axis of blade (1060) while end effector (1050) remains articulated, and drive clamp arm (1052) between the open and closed configuration relative to blade (1060) while end effector (1050) remains articulated.

It should be understood that end effector (1050) and shaft assembly (1032) may be actuated longitudinally relative to instrument base (1000) to any suitable position in accordance with the description above, prior to, during, or after the exemplary use of clamp arm drive tube (1070) described below.

As mentioned above, end effector (1050), shaft assembly (1032), and instrument base (1000) are configured to be rotated about longitudinal axis (LA) defined by proximal shaft portion (1036) via interaction with a rotational assembly of a suitable robotic arm (similar to rotational assembly (70) of robotic arm (32) described above). It should be understood that rotation of end effector (1050) in its entirely about longitudinal axis (LA) (i.e. the “first roll” functionality) may be performed before, after, or at any time during the below mentioned process, thereby providing the operator a greater degree of control of end effector (1050).

Figure 24A:
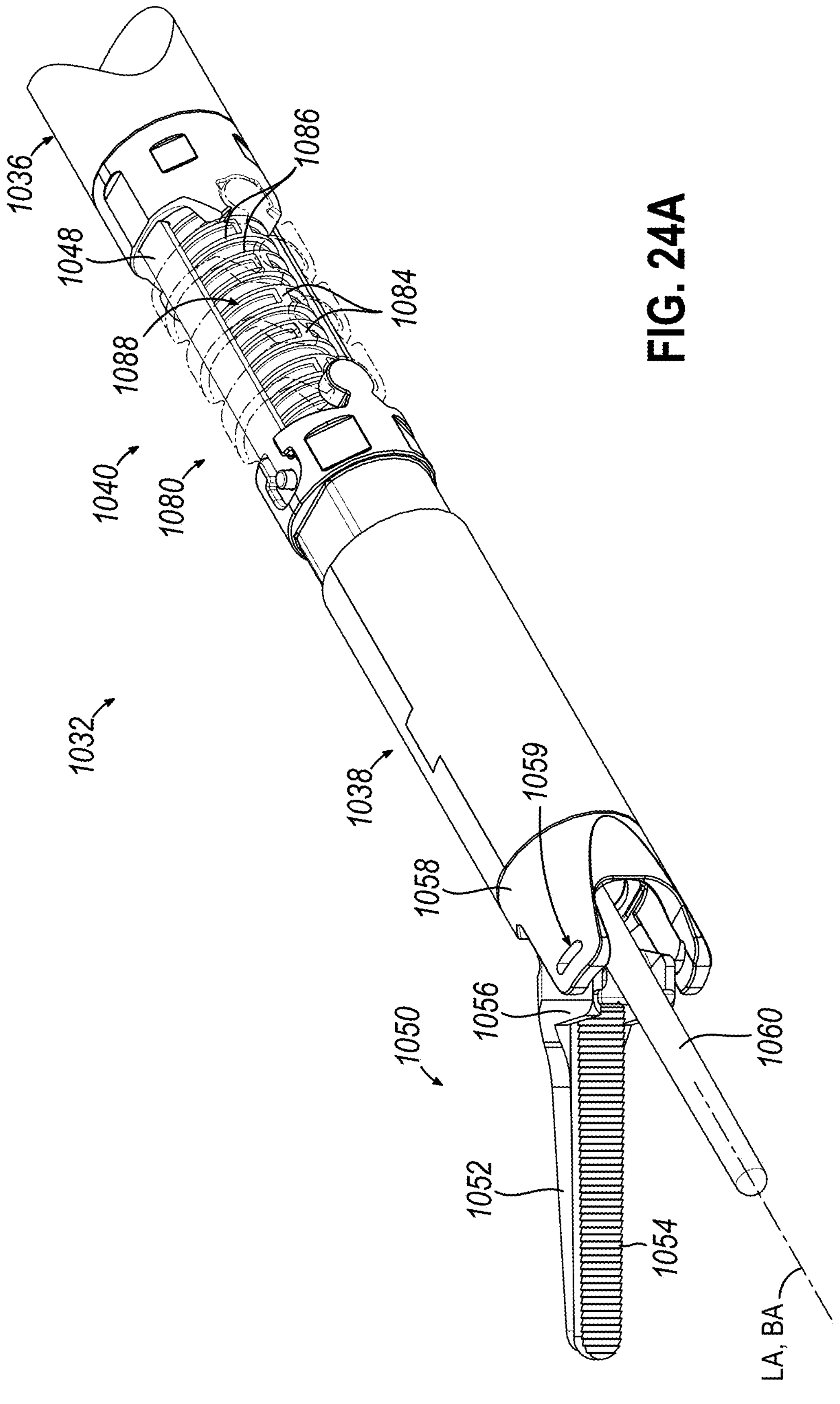
FIG. 24A depicts a perspective view of the articulation section of FIG. 16, and the end effector of FIG. 11A, with selected portions being transparent for purposes of clarity, where the articulation section is in the straight configuration, where a clamp arm of the end effector is in a first rotational position and an open position.
Figure 24B:
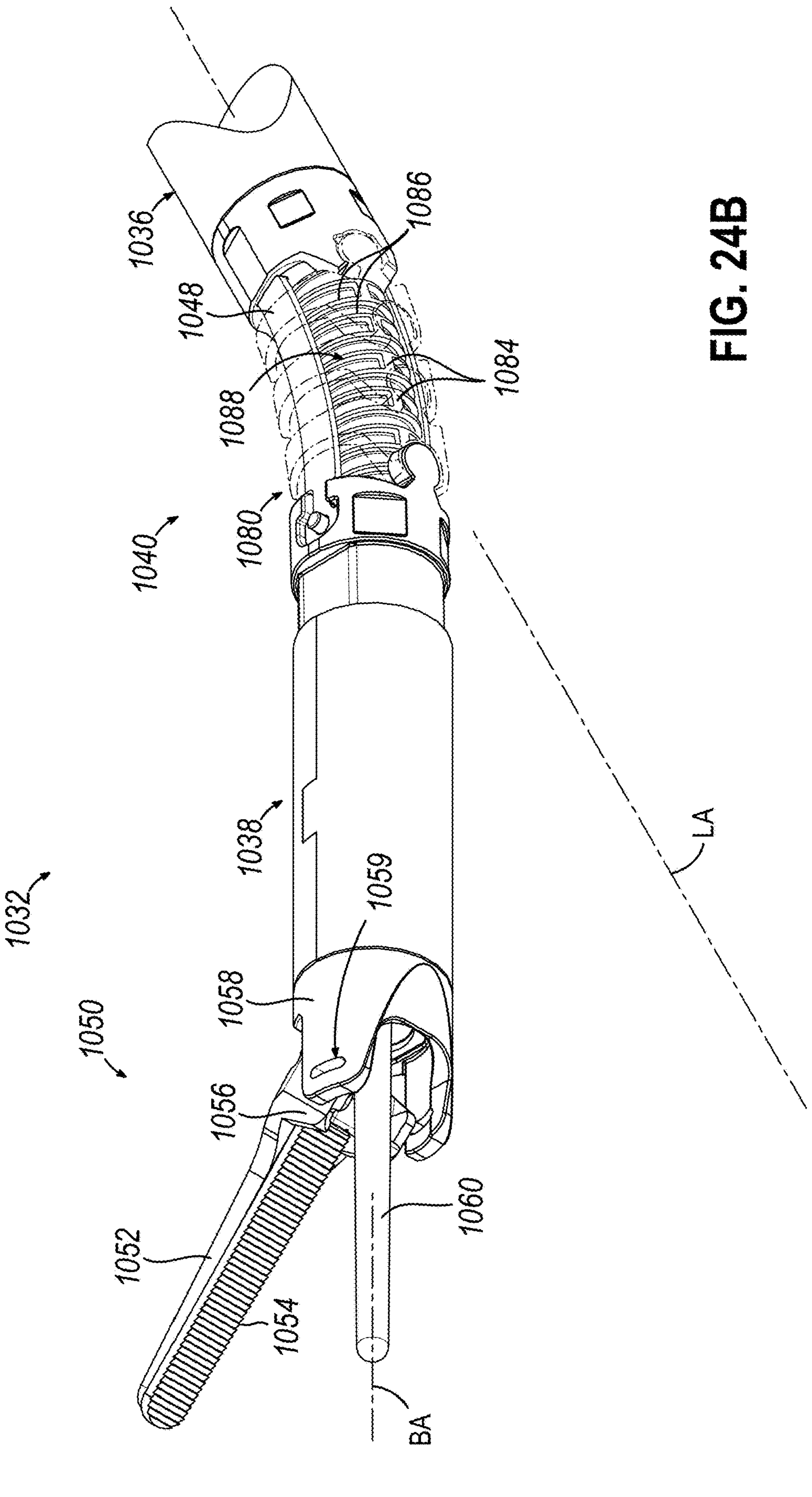
FIG. 24B depicts a perspective view of the articulation section of FIG. 16, and the end effector of FIG. 11A, with selected portions being transparent for purposes of clarity, where the articulation section is in the articulated configuration, where the clamp arm of FIG. 24A is in the first rotational position and the open position.

First, as shown between FIGS. 23A-23B and 24A-24B, the operator may articulate end effector (1050) by driving translation of articulation band (1048) in an opposing fashion in accordance with the description herein. As shown in FIG. 24A, while in the straight configuration, the longitudinal axis (BA) of blade (1060) and the longitudinal axis of proximal shaft portion (1036) are substantially aligned. As shown in FIG. 24B, while in the articulated configuration, the longitudinal axis of blade (BA) forms an angle with the longitudinal axis (LA) of proximal shaft portion (1036).

Figure 23A:
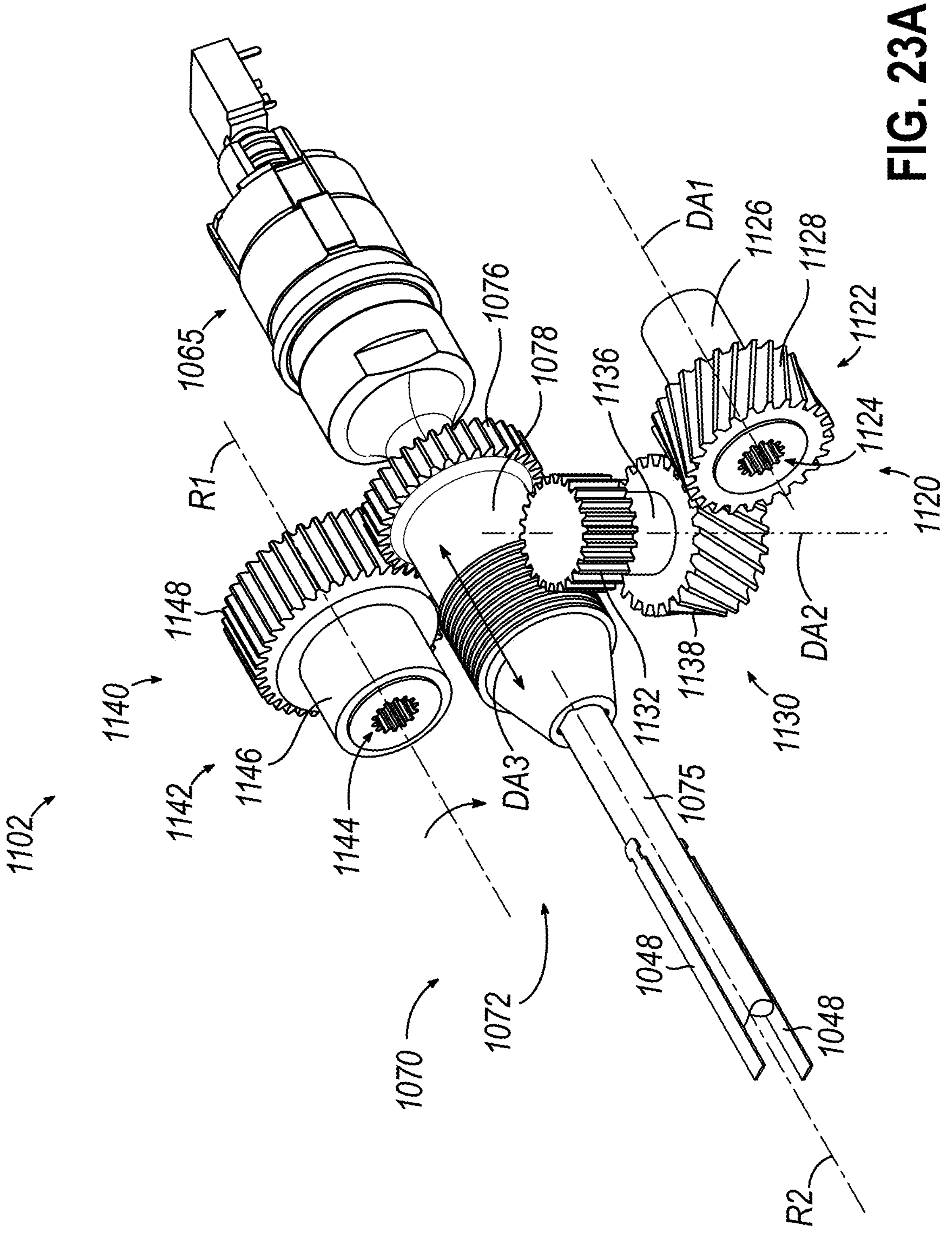
FIG. 23A depicts a perspective view of the proximal drive section of FIG. 22 and a pair of articulation bands associated with the distal drive section of FIG. 22, where the articulation bands are in a first configuration associated with the articulation section of FIG. 16 being in a straight configuration.
Figure 23B:
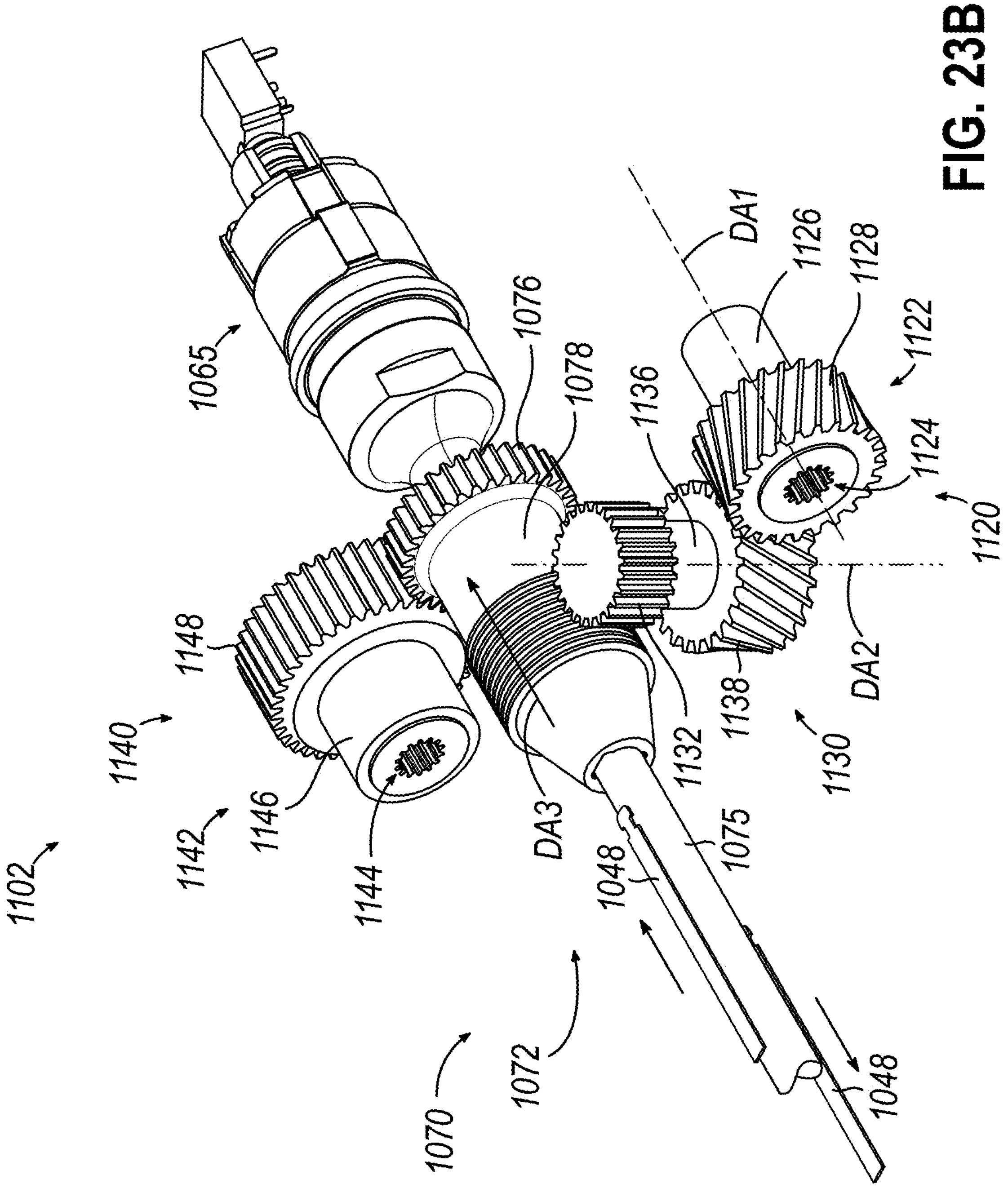
FIG. 23B depicts a perspective view of the proximal drive section of FIG. 22 and the pair of articulation bands of FIG. 23A, where the articulation bands are in a second configuration associated with the articulation section of FIG. 16 being in an articulated configuration.
Figure 23C:
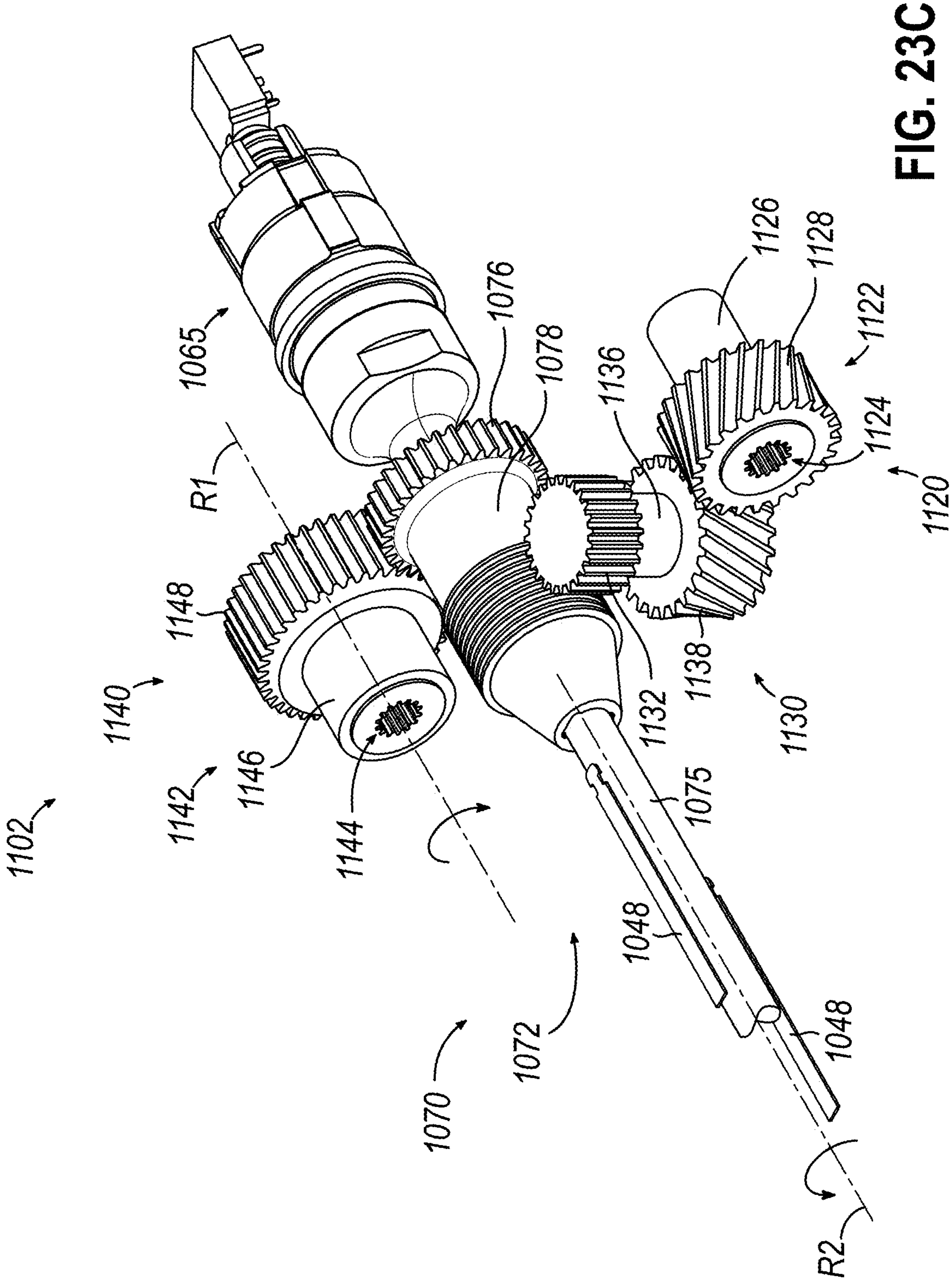
FIG. 23C depicts a perspective view of the proximal drive section of FIG. 22 and the pair of articulation bands of FIG. 23A, where the articulation bands are in the second configuration associated with the articulation section of FIG. 16 being in the articulated configuration, where the proximal drive section drives rotation of the clamp arm drive tube of FIG. 18.

While end effector (1050) is in the articulated configuration, as shown in FIG. 24B, the operator may desire to roll clamp arm (1052) about blade (1060) in order to grasp tissue along a different longitudinally extending contact surface of blade (1060). Therefore, as shown in FIG. 23C, the operator may drive rotation clamp arm rotary drive (1140) in accordance with the description herein, to thereby rotate clamp arm drive tube (1070). It should be understood that the operator may rotate clamp arm drive tube (1070) in either angular direction about rotary axis (R2) with any suitable angular displacement as would be apparent to one skilled in the art in view of the teachings herein.

Figure 24C:
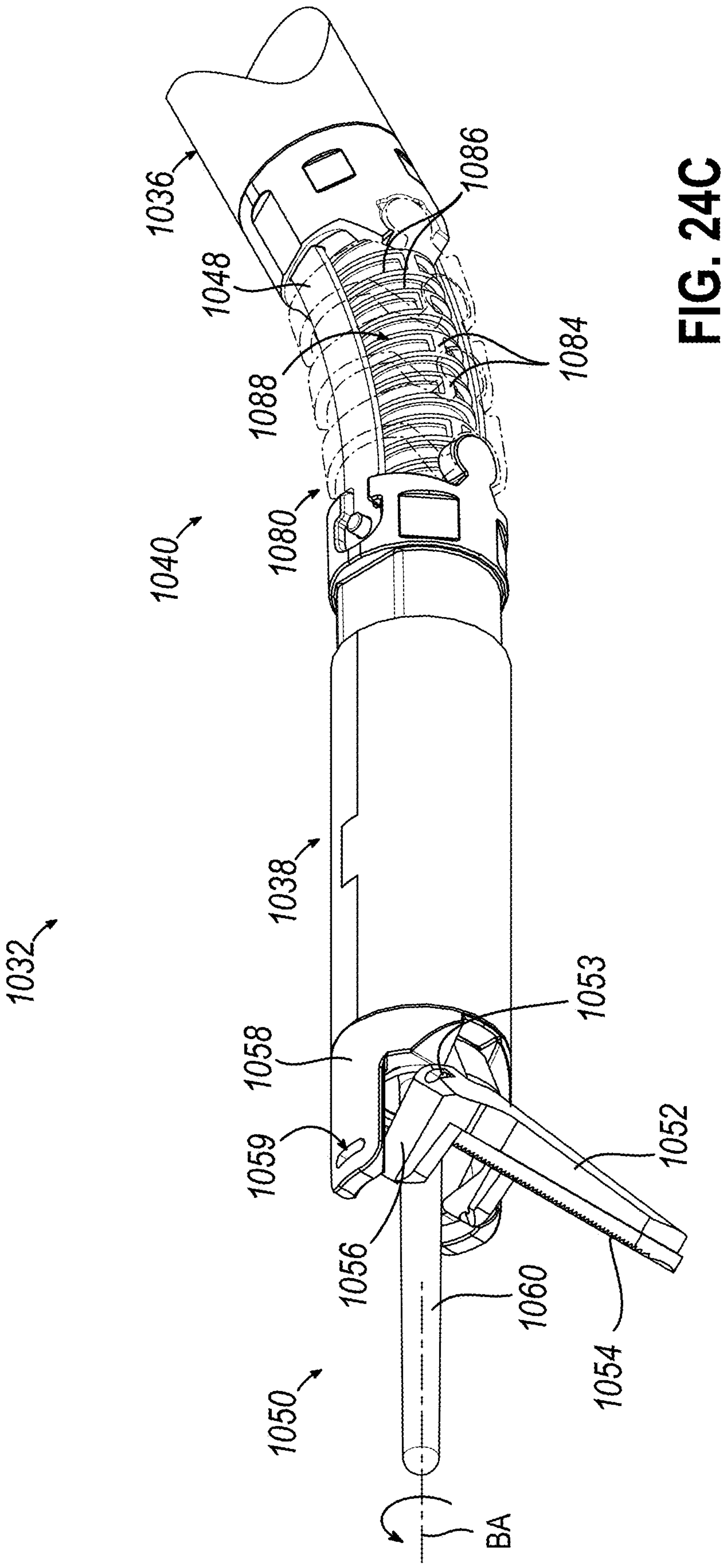
FIG. 24C depicts a perspective view of the articulation section of FIG. 16, and the end effector of FIG. 11A, with selected portions being transparent for purposes of clarity, where the articulation section is in the articulated configuration, where the clamp arm of FIG. 24A is in a second rotational position and the open position.

As shown in FIG. 23C, rotation of clamp arm rotary drive (1140) rotates tubular body (1078) and elongated intermediate portion (1075). As shown in FIG. 24C, rotation of elongated intermediate portion (1075) is suitably transferred to flexible section (1080), which contains sufficient rigidity to transfer the rotational forces to tongues (1058, 1094) to thereby roll clamp arm (1052) about longitudinal axis of blade (BA). Therefore, the operator may selectively roll clamp arm (1052) to any suitable rotational position about blade (1060) in order to grasp tissue along a desired longitudinally extending contact surface of blade (1060). This is the “second roll” functionally of end effector (1050), compared to the “first roll” functionally of rotating end effector (1050) in its entirety about longitudinal axis (LA) of proximal shaft portion (1036).

It should be understood that the plurality of longitudinally extending connecting members (1084) shown in FIG. 24B are angularly offset 180 degrees from the plurality of longitudinally extending connecting members (1084) shown in FIG. 24C due to rotation of flexible section (1080) in accordance with the description herein.

Figure 23D:
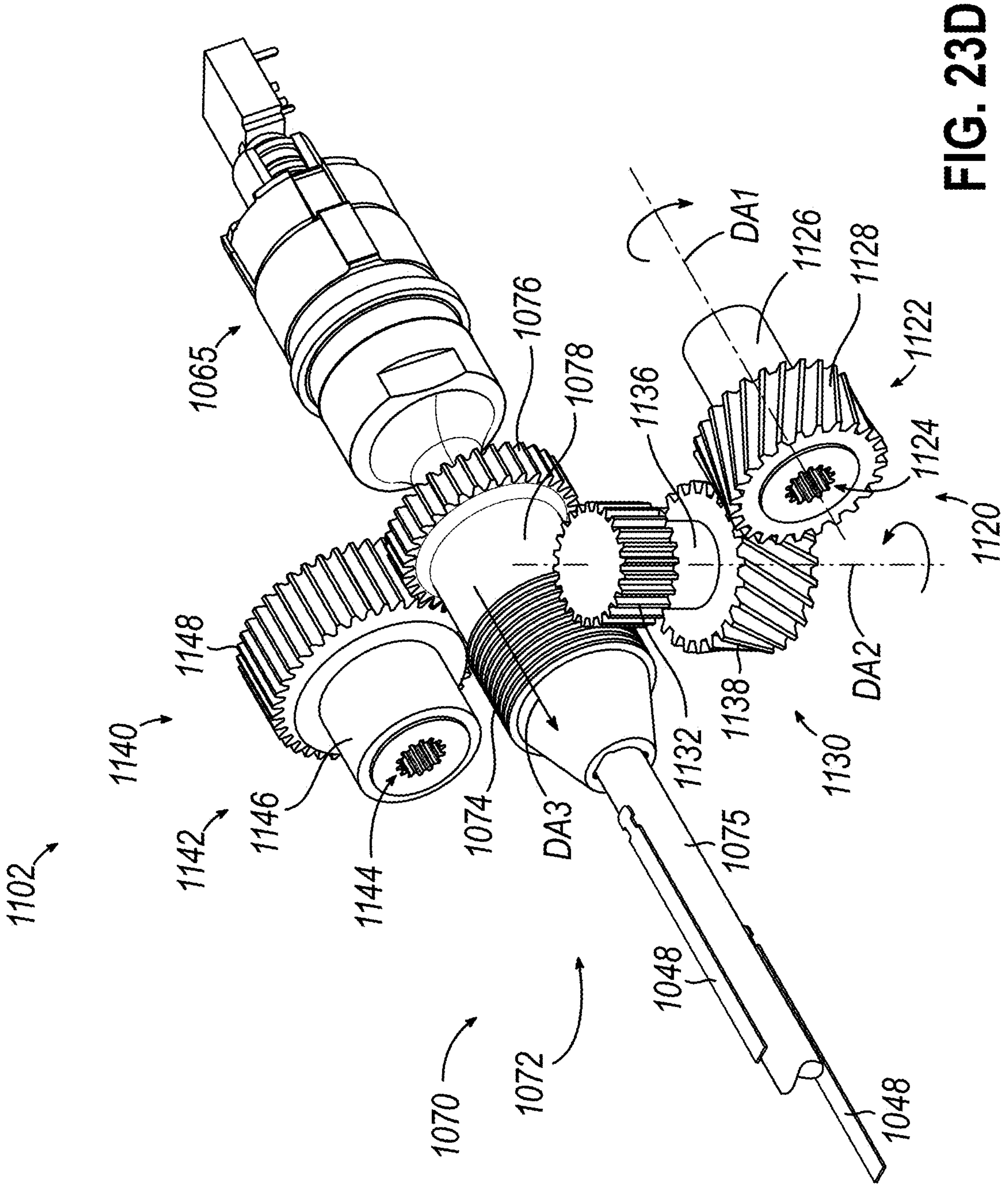
FIG. 23D depicts a perspective view of the proximal drive section of FIG. 22 and the pair of articulation bands of FIG. 23A, where the articulation bands are in the second configuration associated with the articulation section of FIG. 16 being in the articulated configuration, where the proximal drive section linearly actuates the clamp arm drive tube of FIG. 18.
Figure 24D:
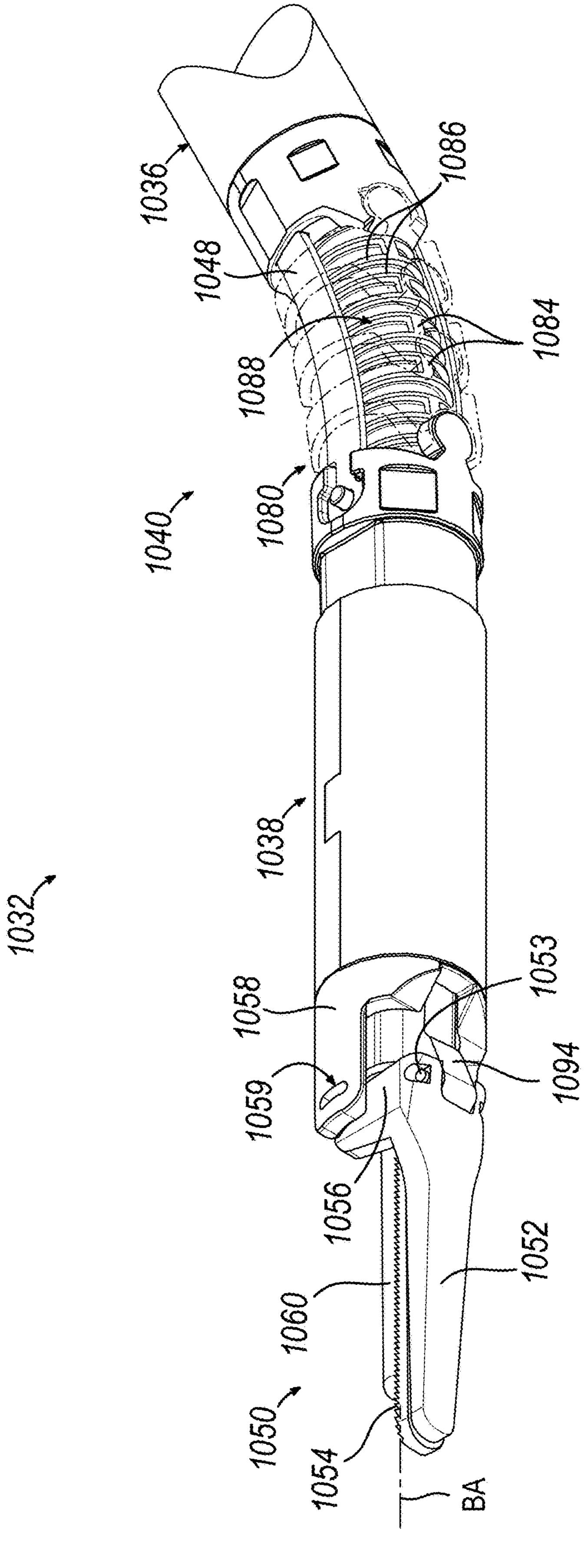
FIG. 24D depicts a perspective view of the articulation section of FIG. 16, and the end effector of FIG. 11A, with selected portions being transparent for purposes of clarity, where the articulation section is in the articulated configuration, where the clamp arm of FIG. 24A is in the second rotational position and a closed position.

With the desired roll angle achieved, next the operator may desire to grasp tissue in order to manipulate and/or operate on tissue in accordance with the description herein. Therefore, as shown in FIG. 23D, the operator may drive distal translation of clamp arm drive tube (1070) via clamp arm closure drive (1120) in accordance with the description herein. As shown in FIG. 24D, distal translation is transferred through flexible section (1080) in order to translate tongue (1094) of clamp arm coupling (1090) distally along longitudinal axis (BA) of blade (1060) to thereby close clamp arm (1052) in accordance with the description herein. With clamp arm (1052) closed, the operator may activate blade (1060) in order to transect/seal tissue in accordance with the description herein.

It should be understood that the operator may open/close clamp arm (1052) and reorient clamp arm (1052) or end effector (1050) in accordance with the description herein using any combination of actions described above to suitably grasp and manipulate tissue as would be apparent to one skilled in the art in view of the teachings herein.

It should also be understood that while the operator may roll clamp arm (1052), and open and close clamp arm (1052), relative to blade (1060) while end effector (1050) is articulated, clamp arm drive tube (1070) is also configured to perform the same functionality while end effector (1050) is in a straight configuration.

Figure 25A:
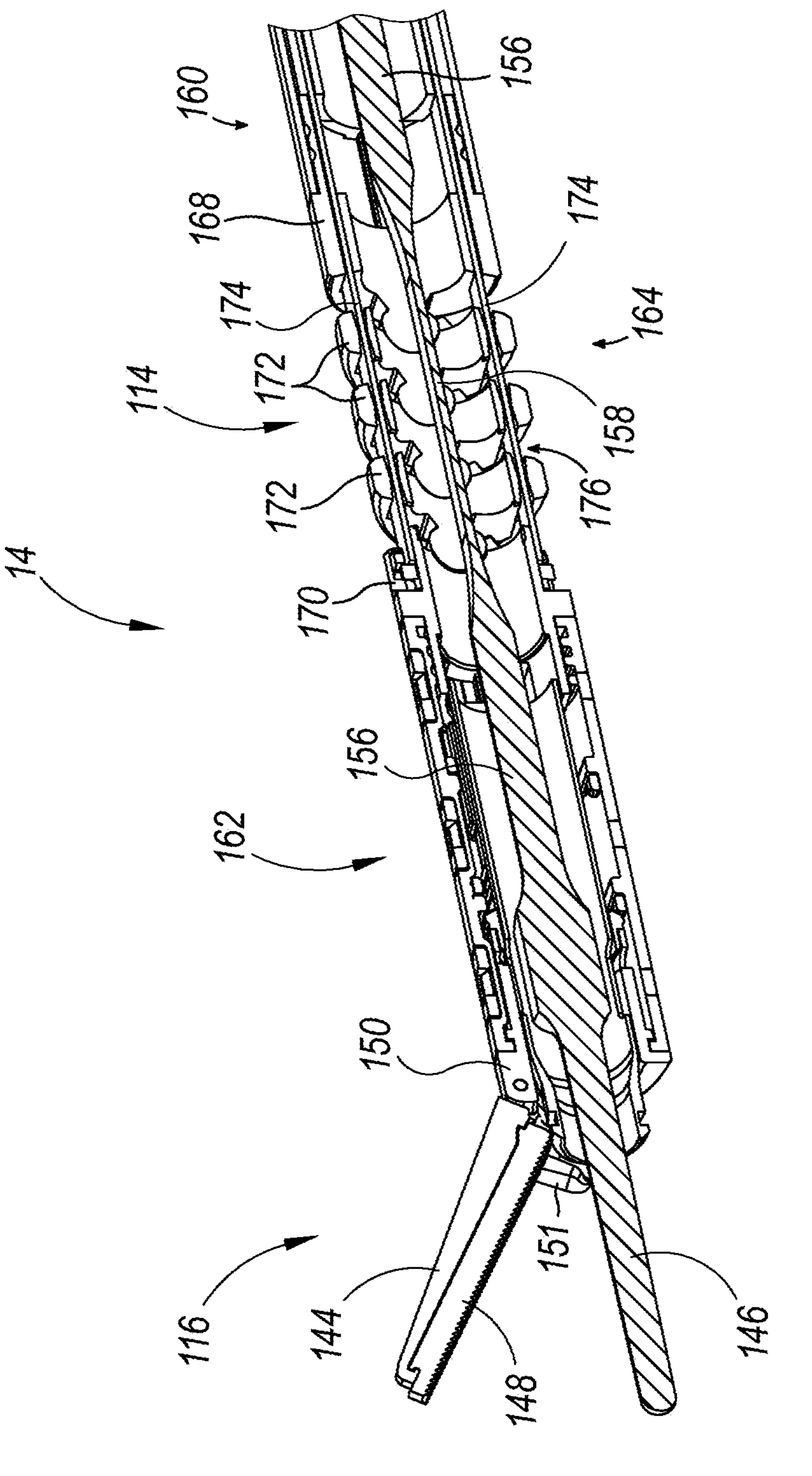
FIG. 25A depicts an enlarged sectional perspective view of the surgical instrument of FIG. 6A with the end effector of FIG. 7A in the open position and the shaft assembly of FIG. 7A the straight configuration.
Figure 25B:
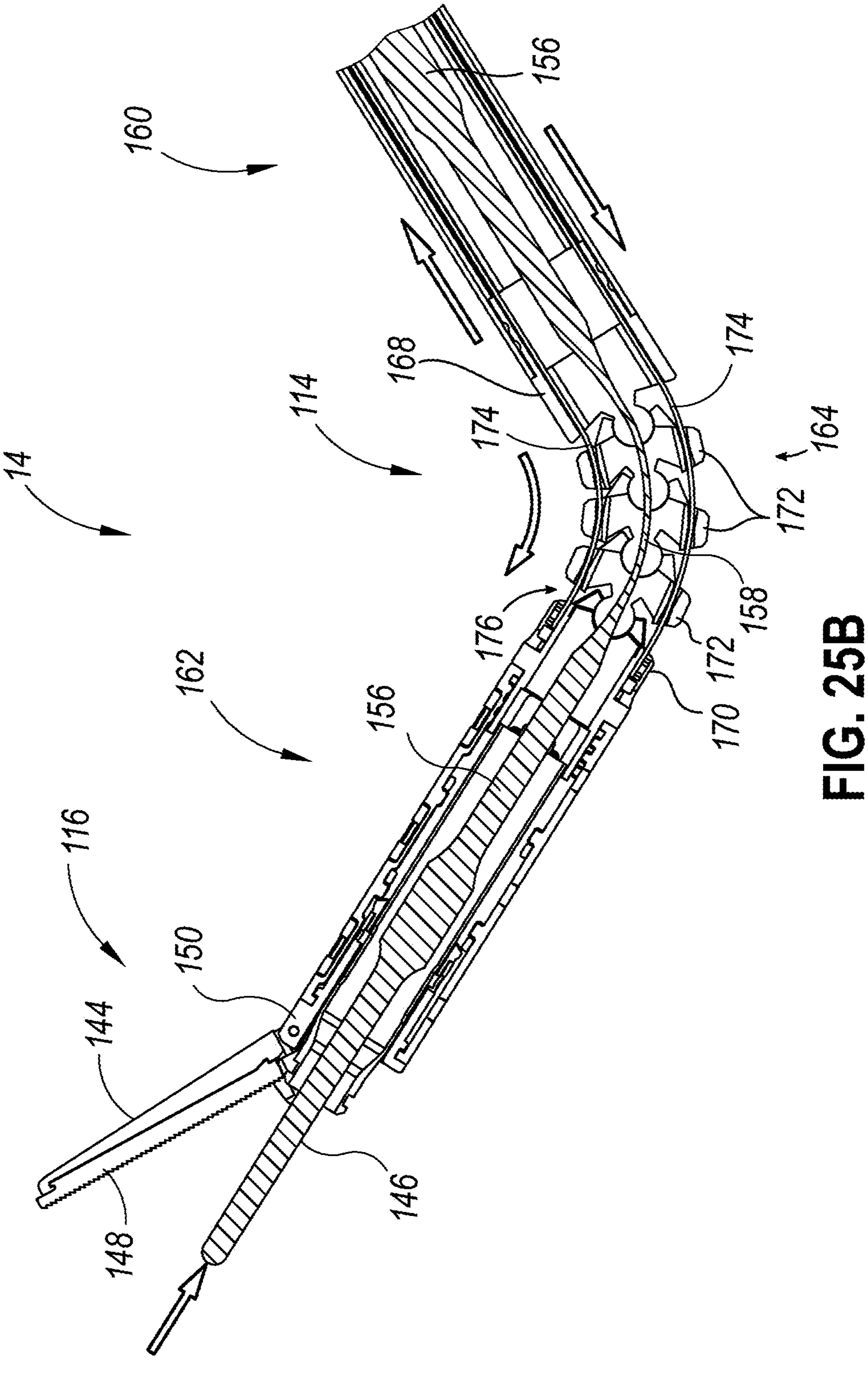
FIG. 25B depicts an enlarged sectional perspective view of the surgical instrument similar to FIG. 9A, but with the end effector in the open position and the shaft assembly in the first articulated configuration.
Figure 26A:
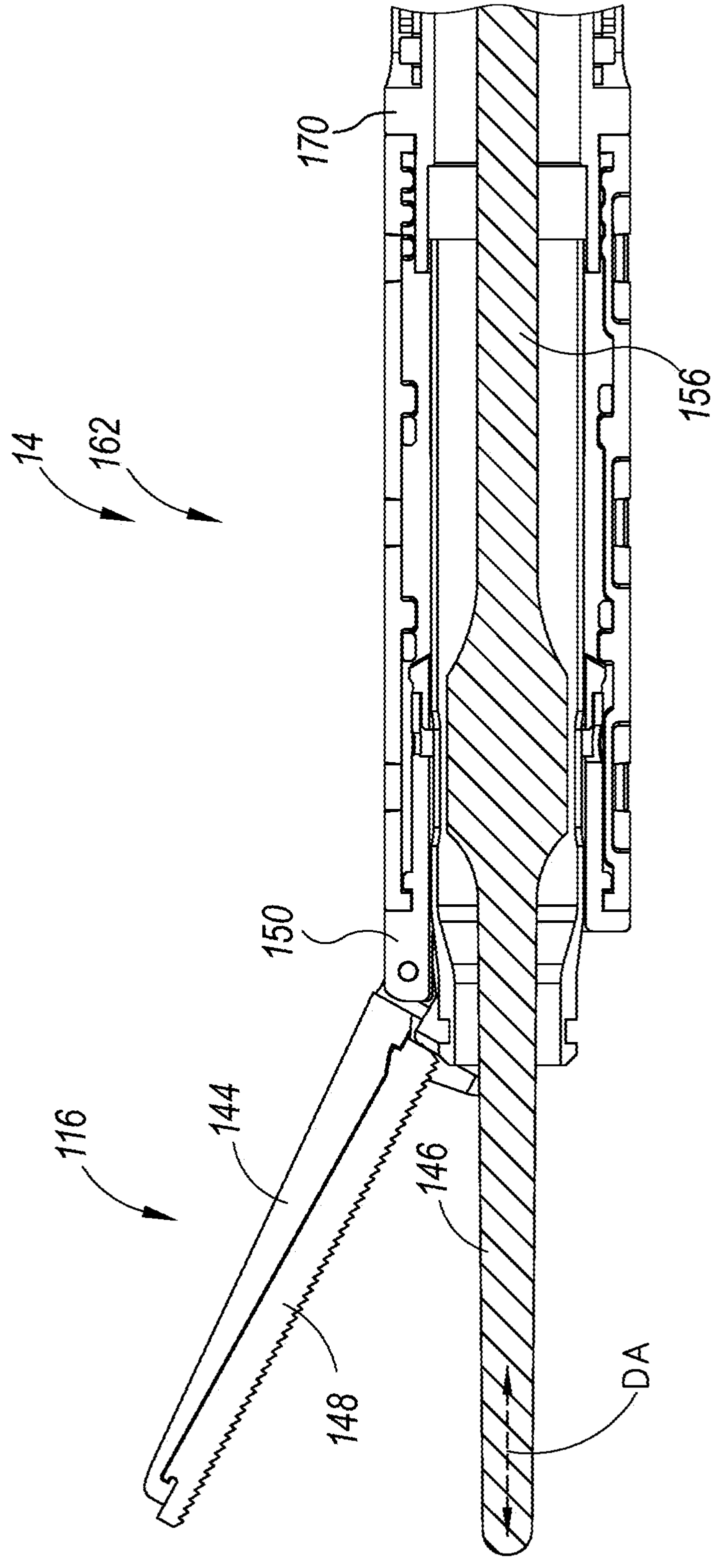
FIG. 26A depicts an enlarged cross-sectional view of the surgical instrument of FIG. 6A taken along a centerline thereof with the end effector of FIG. 7A in the open position and the shaft assembly of FIG. 7A in the straight configuration.
Figure 26B:
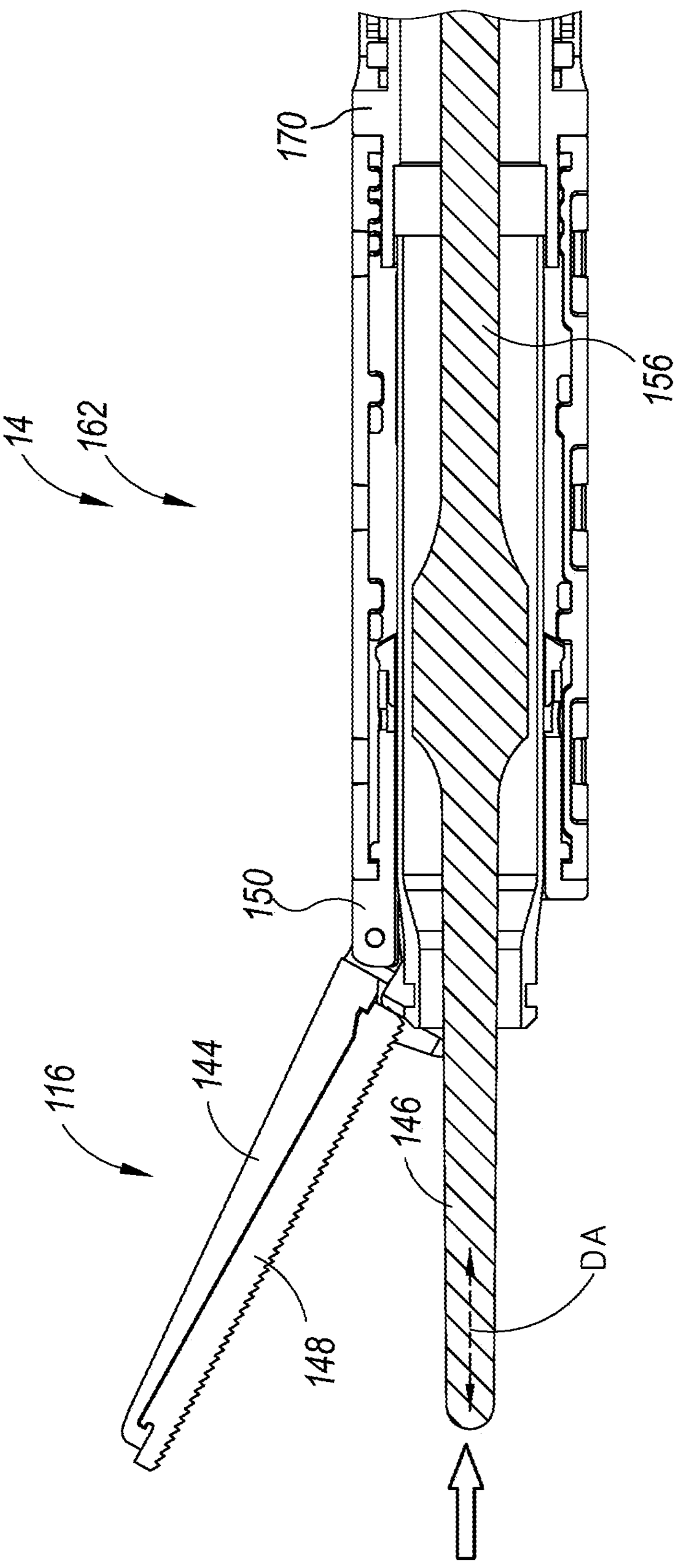
FIG. 26B depicts an enlarged cross-sectional view of the surgical instrument similar to FIG. 9A but with the end effector in the open position and the shaft assembly in the first articulated configuration.

III. Exemplary Ultrasonic Surgical Instrument with Distally Grounded Waveguide As mentioned above, end effector (116) is coupled to distal shaft portion (162), while distal shaft portion (162) is coupled with distal link (170) of articulation section (164). As also mentioned above, the distal ends of articulation bands (174) are coupled with distal link (170) such that opposing translation of articulation bands (174) causes articulation section (164) and flexible portion (158) of waveguide (156) to bend (see FIGS. 25A-25B), thereby laterally deflecting end effector (116) away from longitudinal axis (161). Waveguide (156) extends from transducer assembly (not shown) to blade (146) (see FIGS. 25A-26B) in order to transmit mechanical oscillations from transducer assembly (not shown) to blade (146) in accordance with the description herein. Therefore, blade (146) is coupled to a portion of waveguide (156) extending proximally from flexible portion (158) (see FIGS. 25A-25B).

Since clamp arm (144) deflects away from longitudinal axis (161) by following distal shaft portion (162), and since blade (146) deflects from longitudinal axis (61) by the bending of flexible portion (158) of waveguide (156), clamp arm (144) and blade (146) may deflect from longitudinal axis (161) along different arc lengths. In other words, the curve length which flexible portion (158) bends while articulation section (164) is in a first articulated configuration may be different than the curve length of the various elements that connect to and deflect clamp arm (144) while articulation section (164) is in the first articulated configuration. The difference in respective arc lengths may result in a shift between blade (146) and clamp arm (144) along a distal axis (DA) (see FIGS. 26A-26B) while articulation section (164) is in an articulated configuration (see FIG. 26B) as compared to a straight configuration (see FIG. 26A). Additionally, various other factors may also contribute to a shifting mismatch between blade (146) and clamp arm (144) relative to each other along distal axis (DA) between the articulated configuration (see FIG. 26B) and the straight configuration (see FIG. 26A). The term “straight configuration” may also be referred to as a “non-articulated configuration” as used herein.

Therefore, It may be desirable for shaft assembly (114) and end effector (116) to have features that accommodate for the above mentioned shift between blade (146) and clamp arm (144) such that blade (146) and clamp arm (144) are substantially aligned relative to each other along distal axis (DA) which blade (146) extends along, regardless of the articulated configuration of shaft assembly (114) and end effector (116). It should be understood that distal axis (DA) may be substantially aligned with longitudinal axis (161) (see FIGS. 7A-7B) of proximal shaft portion (160) when shaft assembly (114) and end effector (116) are in the straight configuration. It should also be understood that distal axis (DA) deflects relative to longitudinal axis (161) along with distal shaft portion (162) when shaft assembly (114) and end effector (116) are in articulated configurations.

Figure 27A:
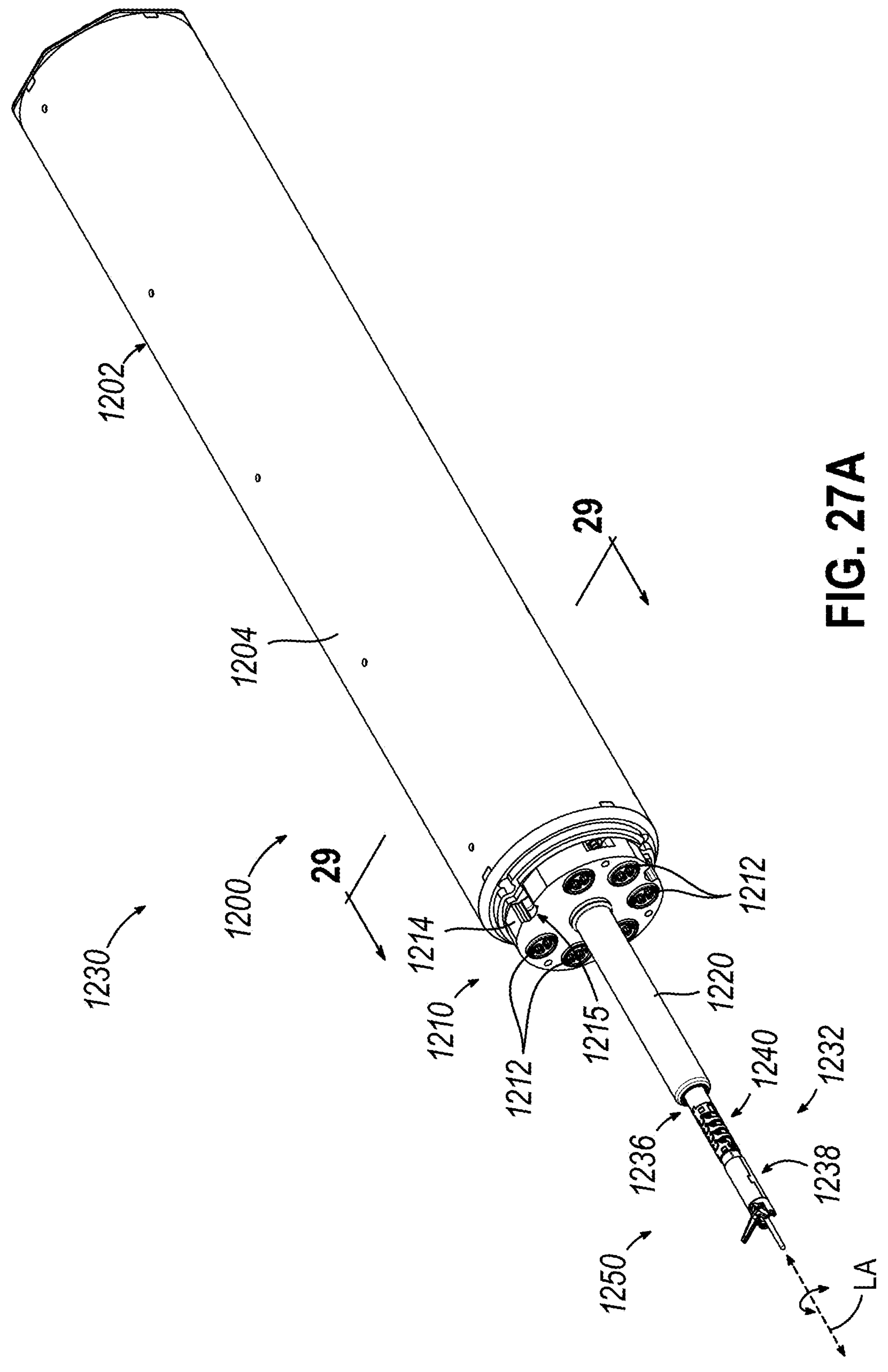
FIG. 27A depicts a perspective view of an exemplary ultrasonic surgical instrument configured to couple with an exemplary robotic arm, where a shaft assembly and an end effector of the surgical instrument are in a proximal position.
Figure 27B:
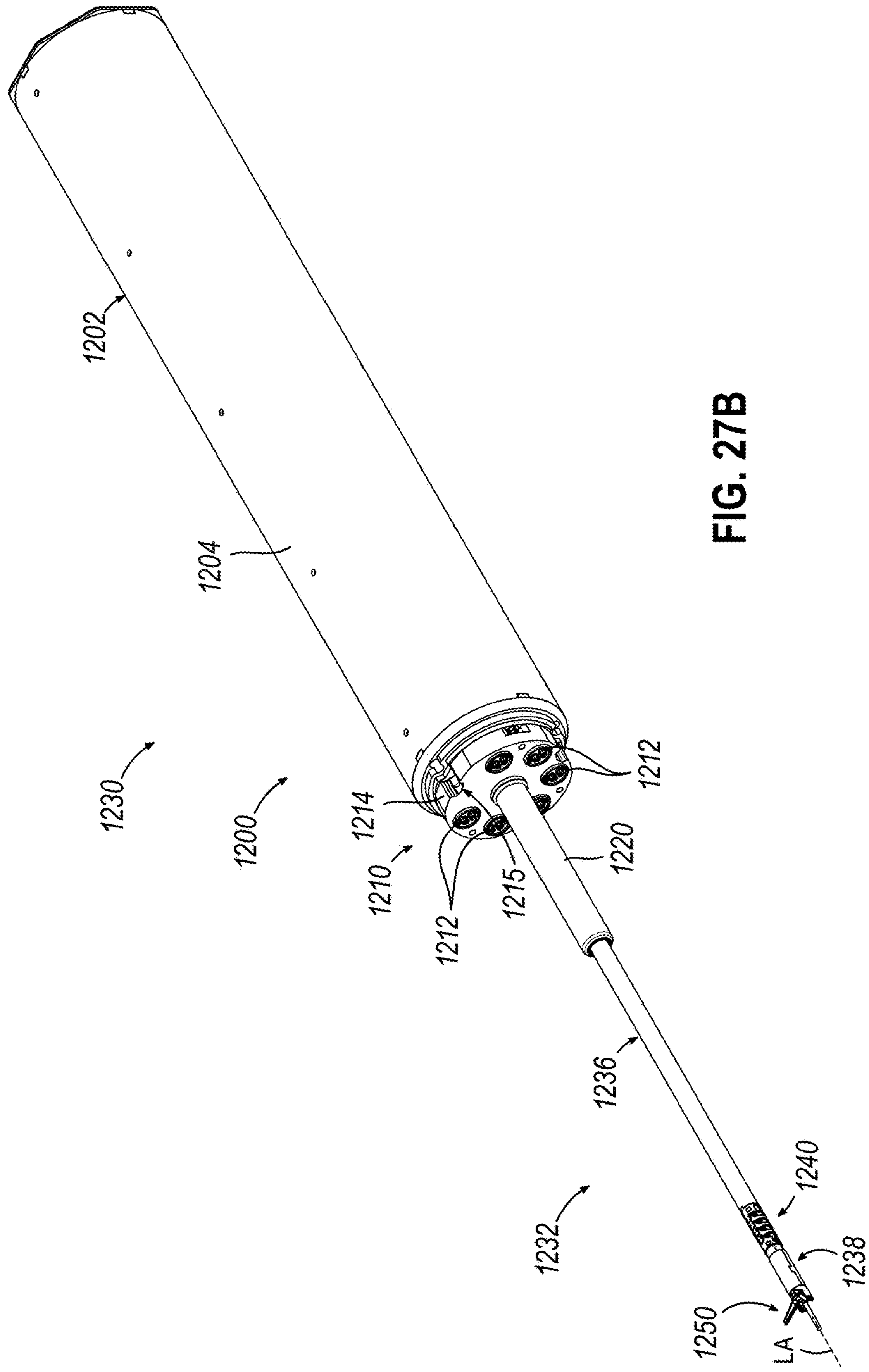
FIG. 27B depicts a perspective view the ultrasonic surgical instrument of FIG. 27A, where the shaft assembly and the end effector are in a distal position.

FIGS. 27A-27B show an alternative ultrasonic surgical instrument (1230) that may be incorporated into an exemplary robotic arm substantially similar to robotic arm (20, 32) described above, with difference elaborated below. Therefore, ultrasonic surgical instrument (1230) may be substantially similar to ultrasonic surgical instrument (14) described above, with differences elaborated below.

Ultrasonic surgical instrument (1230) includes an instrument base (1200), a shaft assembly (1232) partially housed within, and extending distally from, instrument base (1200), and an end effector (1250) extending distally from shaft assembly (1232). Instrument base (1200), shaft assembly (1232), and end effector (1250) may be substantially similar to instrument base (76), shaft assembly (114), and end effector (116) described above, with differences elaborated below.

As will be described in greater detail below, instrument base (1200) is configured to couple with a suitable robotic arm such that instrument base (1200) may actuate shaft assembly (1232) and end effector (1250) in accordance with the description herein. As will also be described in greater detail below, end effector (1250) includes a waveguide grounding assembly (1280) (see FIGS. 34-35) configured to prevent shifting of ultrasonic blade (1260) relative to clamp arm (1252) (see FIGS. 33-34) in the articulated configuration in order to keep an ultrasonic blade (1260) and a clamp arm (1252) substantially aligned relative to each other along distal axis (DA) of blade (1260), regardless of the articulated configuration of end effector (1250).

A. Exemplary Instrument Base

FIGS. 27A-29 show ultrasonic surgical instrument (1230) with instrument base (1200) as briefly discussed above. Instrument base (1200) includes a chassis housing (1202), an attachment interface (1210), and a distally extending sheath (1220). Chassis housing (1202) includes a cylindrical chamber (1204) dimensioned to slidably house a drive chassis (1234) of shaft assembly (1232). While in the current example, chamber (1204) is cylindrically shaped, any other suitably shape may be used as would be apparent to one skilled in the art in view of the teachings herein.

Figure 30:
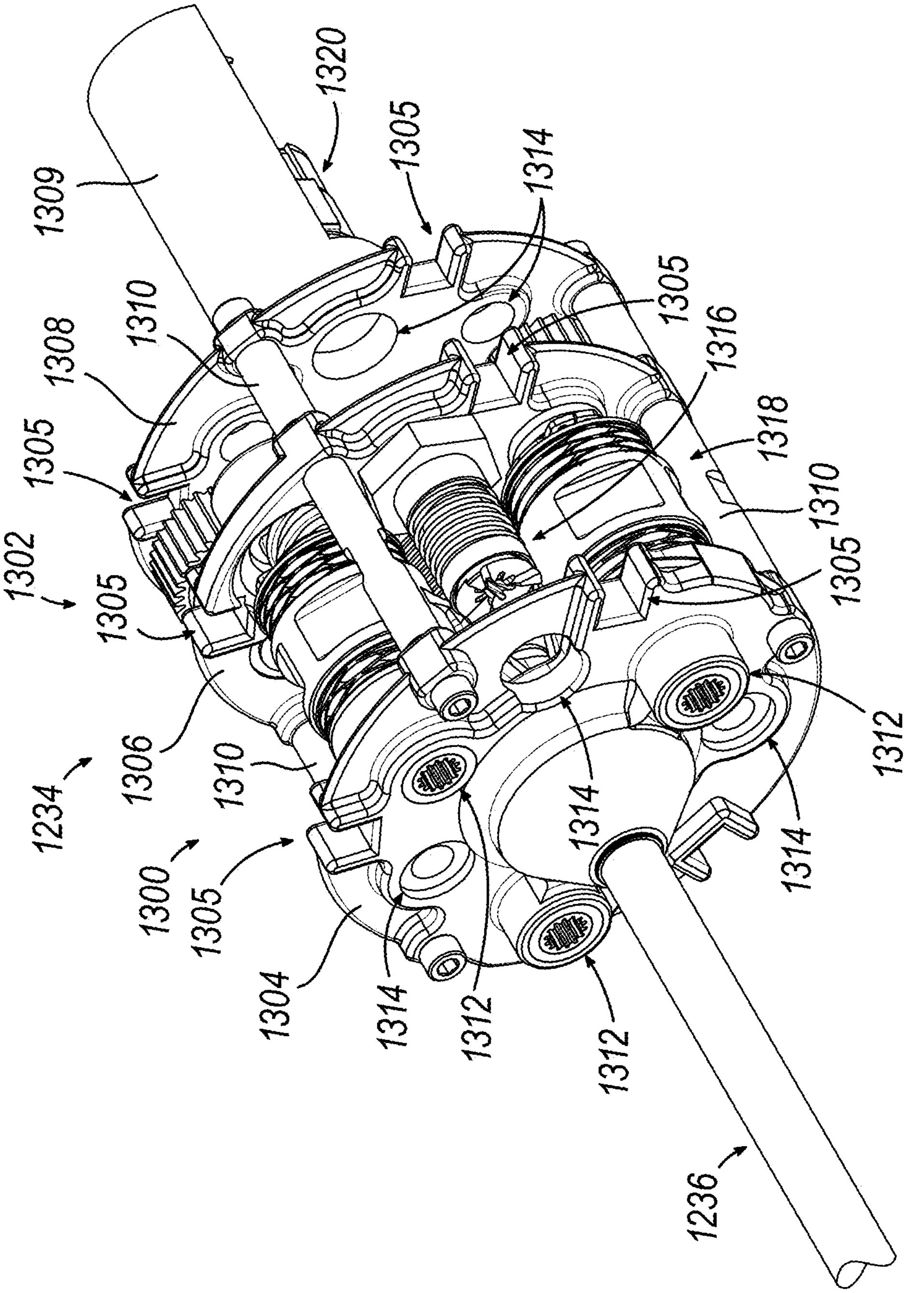
FIG. 30 depicts an enlarged perspective view of a drive chassis of the shaft assembly of FIG. 27A.
Figure 31:
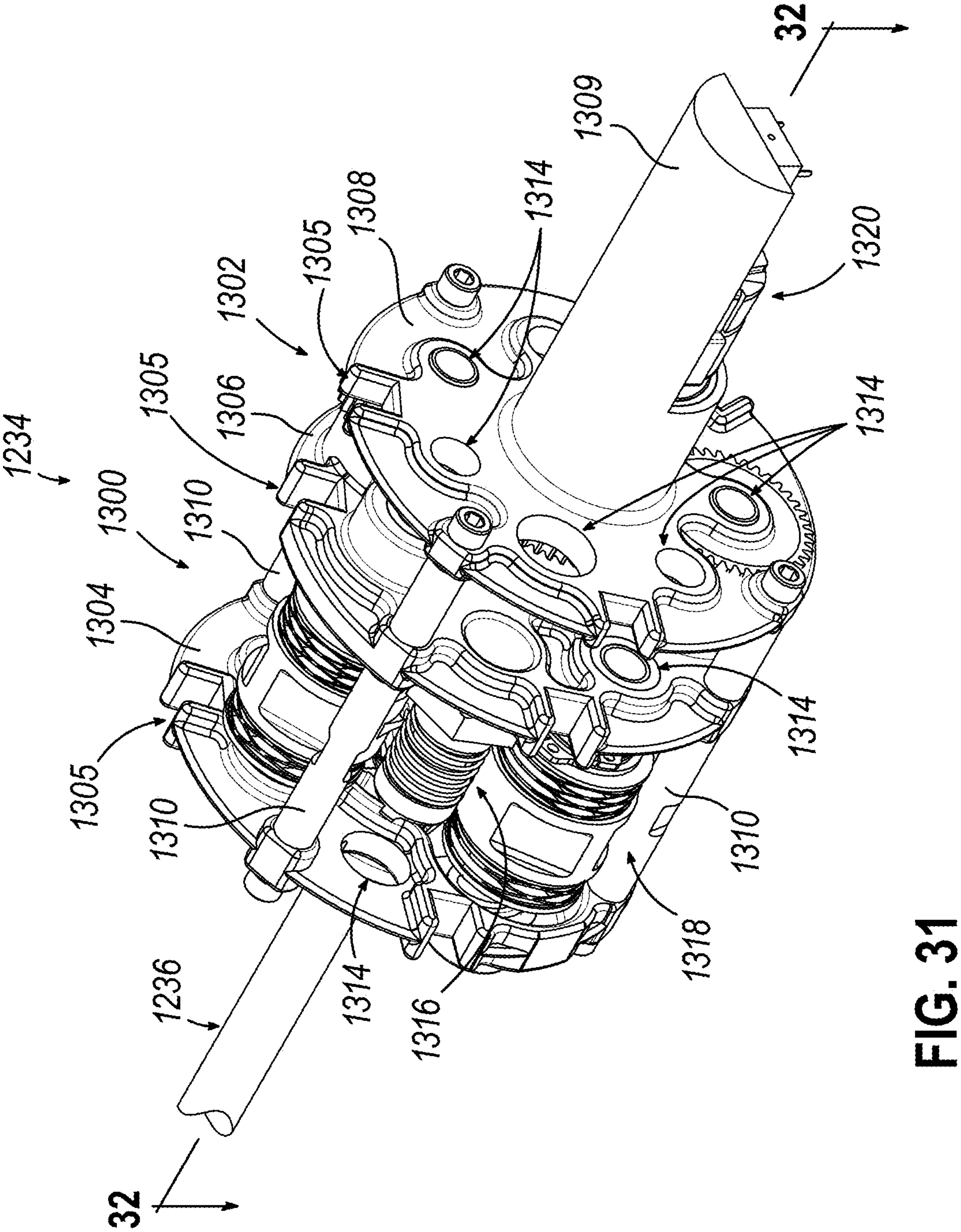
FIG. 31 depicts another enlarged perspective view of the drive chassis of FIG. 30.

Chassis housing (1202) further includes three guide rails (1206) that are fixed to, and extend longitudinally along, an interior surface of cylindrical chamber (1204). Guide rails (1206) are dimensioned with fit within respective alignment channels (1305) of each chassis plate (1304, 1306, 1308) of drive chassis (1234) (see FIGS. 28 and 30) while cylindrical chamber (1204) slidably houses drive chassis (1234).

As will be described in greater detail below, drive chassis (1234) is configured to actuate longitudinally within cylindrical chamber (1204) such that guide rails (1206) define a longitudinal path for drive chassis (1234) to travel along. Additionally, as will be described in greater detail below, instrument base (1200) is configured to be rotated by a suitable rotational assembly of a suitable robotic arm (similar to rotational assembly (70) of robotic arm (32) described above), such that guide rails (1206) transmit rotational forces to drive chassis (1234), the rest of shaft assembly (1232), and end effector (1250), thereby rotating surgical instrument (1230) as a whole about longitudinal axis (LA) defined by a proximal portion (1236) of shaft assembly (1232) (see FIG. 27A).

Attachment interface (1210) is configured to couple instrument base (1200) with a suitable instrument driver, similar to instrument driver (66) described above. Attachment interface (1210) includes a plurality of drive inputs (1212), an interface plate (1214) defining a plurality of notches (1215), a plurality of elongated splined shafts (1216) extending proximally from a respective drive input (1212) into the interior of cylindrical chamber (1204), and an elongated threaded rod (1218) extending proximally from a respective drive input (1212) into the interior of cylindrical chamber (1204).

Interface plate (1214) is fixed to both chassis housing (1202) and distally extending sheath (1220). Therefore, rotation of interface plate (1214) drives rotation of both chassis housing (1202) and distally extending sheath (1220). Notches (1215) are dimensioned to receive selected portions of a rotational assembly of a suitable robotic arm (similar to rotational assembly (70) of robotic arm (32) described above) such that the rotational assembly of the robotic arm may rotate interface plate (1214), chassis housing (1202), and distally extending sheath (1220) about longitudinal axis (LA) defined by a proximal portion (1236) of shaft assembly (1232).

Figure 28:
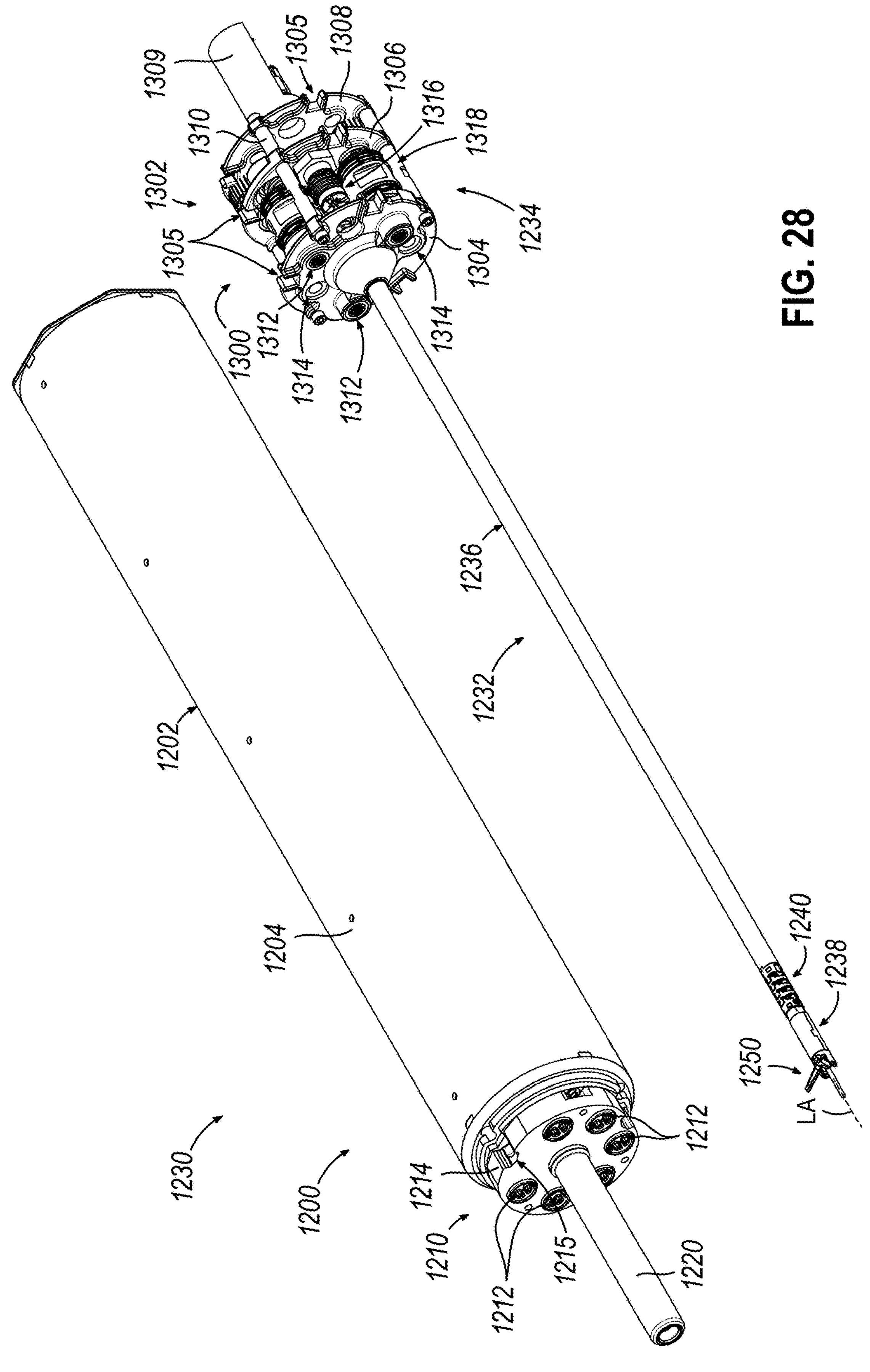
FIG. 28 depicts an exploded perspective view of the ultrasonic surgical instrument of FIG. 27A.
Figure 29:
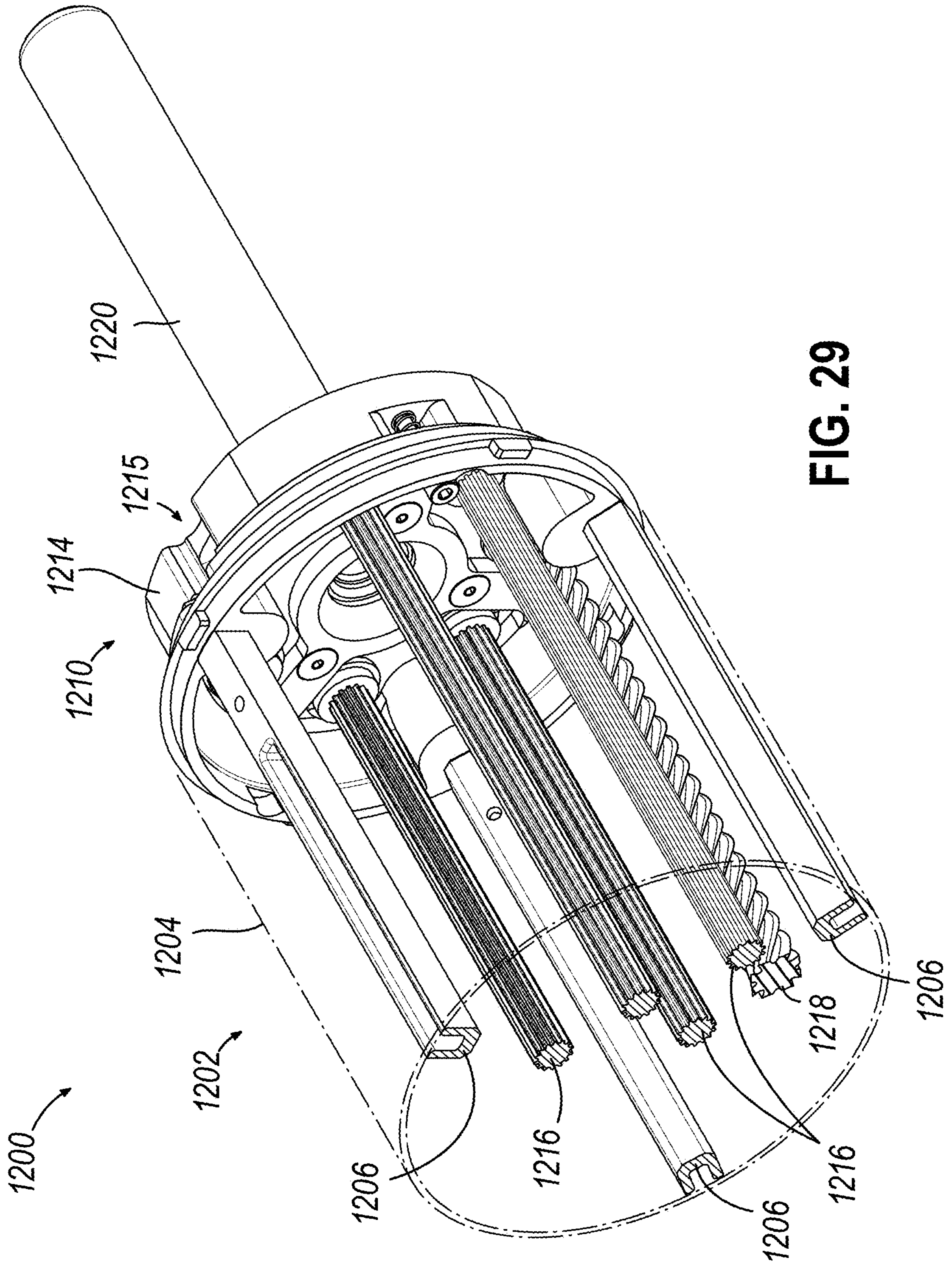
FIG. 29 depicts a sectional perspective view of an instrument base of the ultrasonic surgical instrument of FIG. 27A taken along section line 29-29 of FIG. 27A, with selected portions being transparent or removed for purposes of clarity.

As mentioned above, guide rails (1206) are dimensioned with fit within respective alignment channels (1305) of each chassis plate (1304, 1306, 1308) of drive chassis (1234) (see FIG. 28). Therefore, rotation of interface plate (1214) via interaction with the rotational assembly (similar to rotational assembly (70) described above) of a suitable robotic arm is configured to drive rotation of the entire ultrasonic surgical instrument (1230) about longitudinal axis (LA) by transmitting rotational forces from instrument base (1200) to shaft assembly (1232) and end effector (1250) via guide rails (1206) and alignment channels (1305). In other words, rotation of interface plate (1214) caused by the rotational assembly of a suitable robotic arm (similar to rotational assembly (70) of robotic arm (32) described above) may provide the capability of end effector (1250) to roll about longitudinal axis (LA) in its entirety.

While interface plate (1214) mates with the rotational assembly of a suitable robotic arm via notches (1215), any other suitable features may be used to suitably couple interface plate (1214) and/or instrument base (1200) with the rotational assembly as would be apparent to one skilled in the art in view of the teachings herein.

Interface plate (1214) defines a central through hole such that the interior of distally extending sheath (1220) and chassis housing (1202) are in communication with each other via the central through hole of interface plate (1214). Therefore, a proximal shaft portion (1236) of shaft assembly (1232) may slidably extend from the interior of chassis housing (1202) through interface plate (1214) and distally extending sheath (1220). Distally extending sheath (1220) is dimensioned to slidably house selective portions of proximal shaft portion (1236).

Drive inputs (1212) are rotatably coupled with interface plate (1214) such that drive inputs (1212) may be independently rotated about their own axis relative to interface plate (1214). Drive inputs (1212) may be rotatably coupled with interface plate (1214) via any suitable features as would be apparent to one skilled in the art in view of the teachings herein, such as rotary bearings. Similar to drive inputs (80) described above, drive inputs (1212) are configured to respectively couple with corresponding drive outputs of a suitable robotic arm (similar to drive outputs (68) of robotic arm (32) described above). Therefore, drive outputs of a suitable robotic arm are configured to independently rotate drive inputs (1212) about their own axis relative to interface plate (1214).

It should be understood that drive inputs (1212) of the current example are distally presented on interface plate (1214) such that drive inputs of a suitable robotic arm (similar to drive outputs (68) of robotic arm (32) described above) would be proximally presented in order to suitably couple with drive inputs (1212). This feature is opposite to that showed in FIG. 5, where drive outputs (68) are distally presented and drive inputs (80) are proximally presented. Therefore, in the current example shown in FIGS. 27A-28, distally presented sheath (1220) would extend through a clearance bore of the instrument driver (similar to clearance bore (67) of instrument driver (66) described above) such that chassis housing (1202) would extend proximally from the instrument driver; while a distal end of distally extending sheath (1220) would extend distally from the instrument driver (similar to instrument driver (66) described above). Of course, this is merely optional, as drive inputs (1212) may be placed and presented at any other suitable location as would be apparent to one skilled in the art in view of the teachings herein.

Drive inputs (1212) are fixed to a respective elongated splined shaft (1216) or elongated threaded rod (1218) such that rotation of drive inputs (1212) leads to rotation of the respective elongated splined shaft (1216) or threaded rod (1218).

Splined shafts (1216) and threaded rod (1218) extend proximally from drive inputs (1212) into a proximal end chassis housing (1202) along a respective longitudinal axis, where each respective longitudinal axis is parallel with longitudinal axis (LA). Splined shafts (1216) and threaded rod (1218) are each rotatably supported by the proximal end of chassis housing (1202). Splined shafts (1216) and threaded rod (1218) may be rotatably supported by the proximal end of chassis housing (1202) via any suitable features as would be apparent to one skilled in the art in view of the teachings herein. For example, splined shafts (1216) and threaded rod (1218) may be coupled to proximal end of chassis housing (1202) via rotatory bearings.

Therefore, splined shafts (1216) and threaded rods (1218) are independently rotatable about their own longitudinal axis via interaction between respective drive inputs (1212) and corresponding drive outputs (similar to drive outputs (68) described above). As will be described in greater detail below, splined shaft (1216) and threaded rods (1218) may be suitably coupled to respective portions of drive chassis (1234) such that rotation of respective splined shafts (1216) and threaded rod (1218) drives actuation of shaft assembly (1232) and/or end effector (1250) in accordance with the description herein.

While in the current example, there are six drive inputs (1212), any suitable number of drive inputs (1212) may be used as would be apparent to one skilled in the art in view of the teachings herein. Also, in the current example, there are four splined shafts (1216), but any other suitable number of splined shafts (1216) may be used as would be apparent to one skilled in the art in view of the teachings herein.

B. Exemplary End Effector

With respect to FIGS. 28-34, end effector (1250) includes an ultrasonic blade (1260) and a clamp arm (1252) having a clamp pad (1254) and a pair of arms (1256); which may be substantially similar to ultrasonic blade (146), clamp arm (144), clamp pad (148), and arms (151), respectively, with differences elaborated below.

Blade (1260) of the present example is positioned at a distal end of an acoustic drivetrain. This acoustic drivetrain includes a transducer assembly (1320) and an acoustic waveguide (1262) having a flexible portion (1264); which may be substantially similar to transducer assembly (not shown), acoustic waveguide (156), and flexible portion (158), described above, respectively, with difference elaborated below.

Blade (1260) is fixedly attached to waveguide (1262) at a distal flange (1265) of waveguide (1262). A proximal end of waveguide (1262) is coupled to transducer assembly (1320) at a coupling section (1322). Waveguide (1262) may be selectively coupled to transducer assembly (1320). When suitably coupled to each other, transducer assembly (1320) is configured to generate ultrasonic vibrations and transmit such vibrations to through waveguide (1262) to reach blade (1260).

Additionally, when suitably coupled to each other, transducer assembly (1320), waveguide (1262), and blade (1260) may move within three-dimensional space with each other. In other words, coupling section (1322) may suitably couple waveguide (1262) with transducer assembly (1320) such that forces imparted on transducer assembly (1320) to rotate/translate transducer assembly (1320) may be transferred onto waveguide (1262) via coupling section (1322), thereby rotating/translating waveguide (1262) and blade (1260) along with transducer assembly (1320). Waveguide (1262) may be selectively coupled to transducer assembly (1320) via any suitably manner as would be apparent to one skilled in the art in view of the teachings herein.

As shown in FIGS. 33-36B, acoustic waveguide (1262) in housed within a waveguide sheath (1266). Waveguide sheath (1266) includes a flexible portion (1268) configured to house corresponding flexible portion (1264) of waveguide (1262). Waveguide sheath (1266) may protect waveguide (1262) from exposure to and accumulation of various external matter during exemplary use. Additionally, flexible portion (1268) of waveguide sheath (1266) may protect flexible portion (1264) from coming into accidental contact with various other structures of instrument (1230) during exemplary use. Waveguide sheath (1266) and waveguide (1262) are housed within corresponding portions of a distal shaft portion (1238), an articulation section (1240), a proximal shaft portion (1236) of shaft assembly (1232), and drive chassis (1234).

Clamp arm (1252) is pivotally coupled to a first tongue (1258) via vertical slots (1259) defined by first tongue (1058) and protrusions (not shown) extending from arms (1256) of clamp arm (1252). Additionally, clamp arm (1252) is pivotally coupled to a second tongue (1270). Relative movement between first tongue (1258) and second tongue (1270) drives clamp arm (1252) to pivot between an open position and a closed position relative to blade (1260) (similar to the pivotal motion of clamp arm (144) shown between FIGS. 7A-7B).

C. Exemplary Articulating Shaft Assembly

Referring back to FIG. 28, shaft assembly (1232) includes drive chassis (1234), proximal shaft portion (1236), articulation section (1240), and distal shaft portion (1238). Drive chassis (1234) is located on a proximal end of proximal shaft portion (1236). Proximal shaft portion (1236), articulation section (1240), and distal shaft portion (1238) may be substantially similar to proximal shaft portion (160), articulation section (164), and distal shaft portion (162) described above, respectively, with differences elaborated below.

Figure 33:
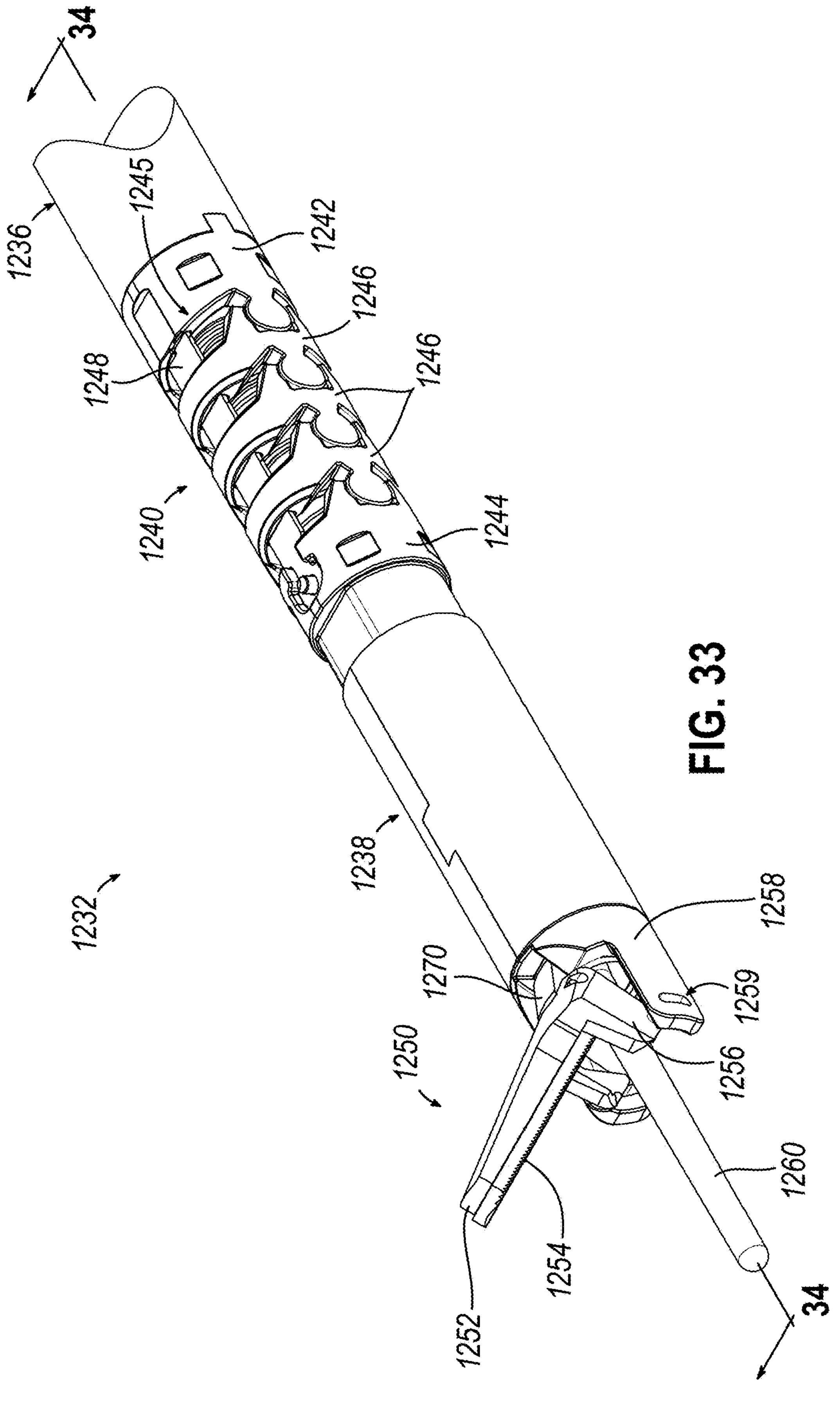
FIG. 33 depicts an enlarged perspective view of a distal end of the shaft assembly and the end effector of FIG. 27A.
Figure 36A:
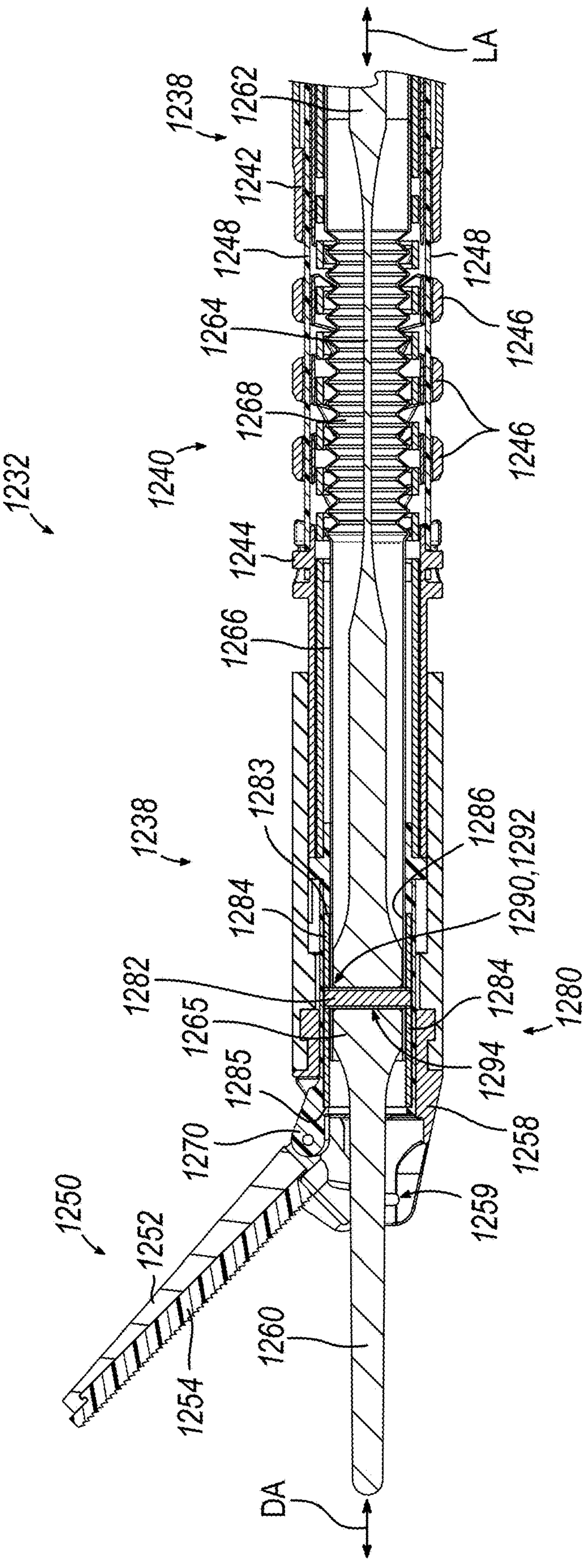
FIG. 36A depicts an enlarged cross-sectional view of the surgical instrument of FIG. 27A taken along a centerline thereof with the end effector in the open position and the shaft assembly in a straight configuration.
Figure 36B:
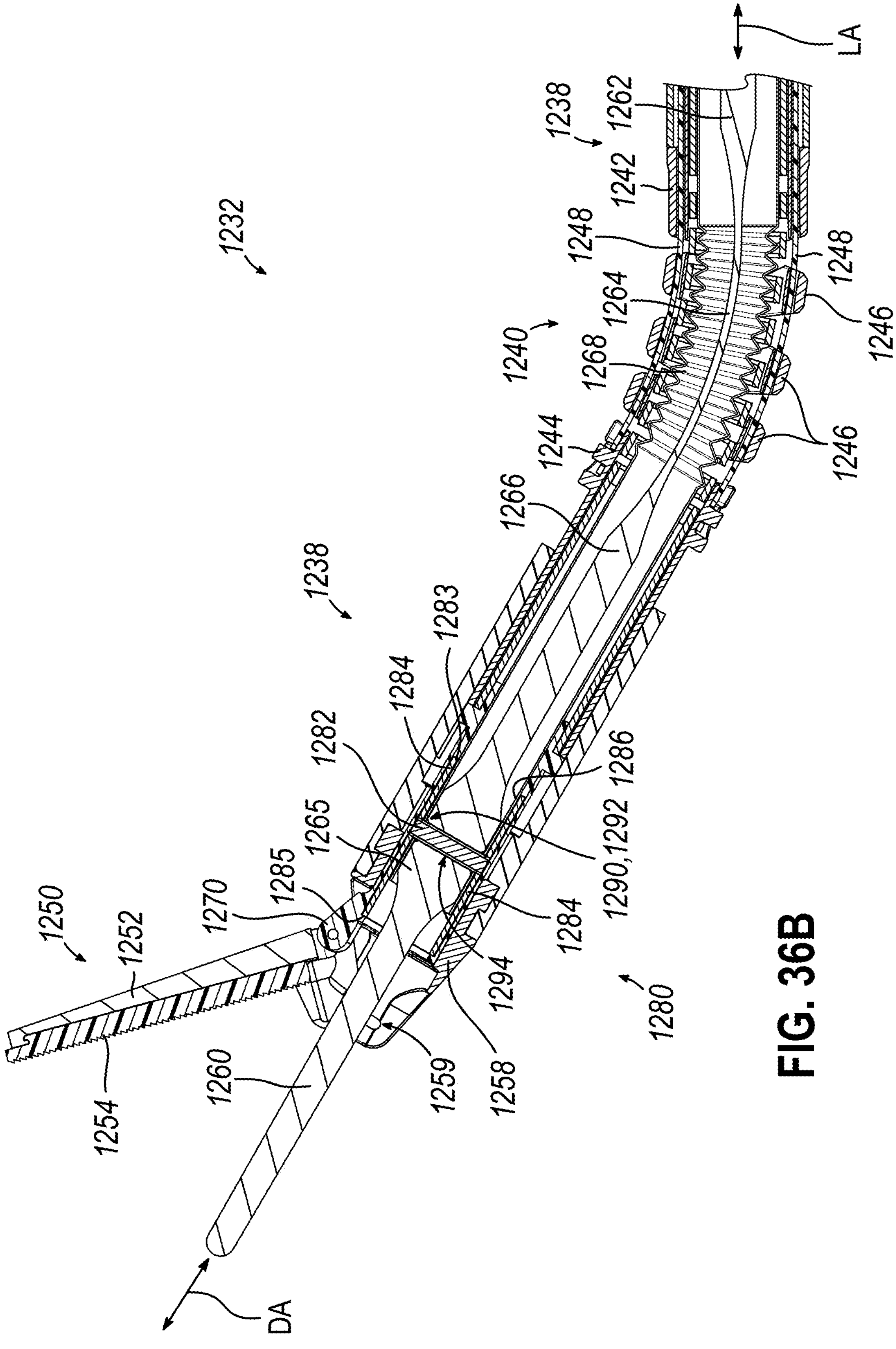
FIG. 36B depicts an enlarged cross-sectional view of the surgical instrument similar to FIG. 36A, but with the end effector in the open position and the shaft assembly in a first articulated configuration.

Therefore, as exemplified in FIGS. 33, 36A, and 36B, articulation section (1240) is configured to selectively position end effector (1250) at various lateral deflection angles relative to longitudinal axis (LA) defined by proximal shaft portion (1236). Articulation section (1240) includes a proximal link (1242), a distal link (1244), a plurality of intermediate links (1246), and a pair of articulation bands (1248) extending through respective channels (1245); which are substantially similar to proximal link (168), distal link (170), intermediate links (172), articulation bands (174), and channels (176), respectively, described above. Therefore articulation bands (1248) are configured to translate in an opposing fashion to drive bending of links (1242, 1244, 1246) to thereby laterally defect end effector (1250) away from longitudinal axis (LA) defined by proximal shaft portion (1236).

As mentioned above and again referring back to FIG. 28 as well as FIGS. 29-32, drive chassis (1234) is configured to be slidably housed within chassis housing (1202) of instrument base (1200). As also mentioned above, and as will be described in greater detail below, drive chassis (1234) is configured to slidably attach to splined shafts (1216) and receive threaded rod (1218) such that rotation of splined shaft (1216) and threaded rod (1218) drives actuation of shaft assembly (1232) and/or end effector (1250).

Drive chassis (1234) includes a distal drive section (1300), a proximal drive section (1302), distal chassis plate (1304), intermediate chassis plate (1306), proximal chassis plate (1308), and a transducer sheath (1309) fixed to, and extending proximally from, proximal chassis plate (1308). Chassis plates (1304, 1306, 1308) are fixed to each other via coupling members (1310). Therefore, chassis plates (1304, 1306, 1308) act as a mechanical frame for distal drive section (1300) and proximal drive section (1302). As mentioned above, chassis plates (1304, 1306, 1308) define channels (1305) dimensioned to receive guide rails (1206) of chassis housing (1202) such that rotation of chassis housing (1202) in accordance with the description herein drives corresponding rotation of chassis plates (1304, 1306, 1308).

Transducer sheath (1309) of proximal chassis plate (1308) includes a coupling flange (1307) that suitably couples transducer assembly (1320) with transducer sheath (1309). Coupling flange (1307) is suitably coupled between proximal chassis plate (1308) and transducer assembly (1320) such that movement of proximal chassis plate (1308) drives corresponding movement of transducer assembly (1320) via coupling flange (1307). Therefore, movement of chassis plates (1304, 1306, 1308) in accordance with the description herein may drive corresponding movement of transducer assembly (1320), waveguide (1262), and blade (1260) via transducer sheath (1309) and coupling flange (1307). For instance rotation of drive chassis (1234) about longitudinal axis (LA), in accordance with the description above, drives corresponding rotation of transducer assembly (1320), waveguide (1262), and blade (1260) about longitudinal axis (LA) via transducer sheath (1309) and coupling flange (1307).

It should be understood that coupling flange (1307) engages transducer assembly (1320) such that transducer assembly may still suitably generate and transfer ultrasonic vibrations to waveguide (1262) in accordance with the description herein. Coupling flange (1307) may be formed of any suitable material as would be apparent to one skilled in the art in view of the teachings herein.

Each chassis plate (1304, 1306, 1308) also defines a plurality of openings (1314). Openings (1314) of individual chassis plates (1304, 1306, 1308) are aligned with corresponding openings (1314) of other chassis plates (1304, 1306, 1308) along an axis that extends parallel with longitudinal axis (LA) of proximal shaft portion (1236). Aligned openings (1314) may be associated with a respective drive assembly and dimensioned to receive either splined shaft (1216) or threaded rod (1218) such that the received splined shaft (1216) or threaded rod (1218) suitably interacts with the corresponding drive assembly (1116, 1118) in accordance with the description herein.

Distal drive section (1300) is housed between distal chassis plate (1304) and intermediate chassis plate (1306). Distal drive section (1300) includes linear drive assembly (1316) and a pair of drive assemblies (1318) associated with articulation section (1240). Proximal drive section (1302) is housed between intermediate chassis plate (1306) and proximal chassis plate (1308). Similarly, proximal drive section (1302) may include any drive assembly (1316, 1318) as would be apparent to one skilled in the art in view of the teachings herein.

Linear drive assembly (1316) is fixed to intermediate plate (1306) and includes an internal female threading configured to mesh the with threading of threaded rod (1218). Since the internal female threading of linear drive assembly (1316) is fixed to intermediate plate (1306), and intermediate plate (1306) is rotationally constrained within chassis housing (1202), rotation of threaded rod (1218) in accordance with the description herein drives linear actuation of drive chassis (1234), the rest of shaft assembly (1232), and end effector (1250) relative to chassis housing (1202) and distally extending sheath (1220). Therefore, rotation of threaded rod (1218), while coupled with linear drive assembly (1316), may actuate end effector (1250) relative to chassis housing (1202) between a proximal position (see FIG. 27A) and a distal position (see FIG. 27B).

Each drive assembly (1318) comprises an internal splined rotary body (1312) dimensioned to slidably receive a corresponding splined shaft (1216), thereby promoting the slidably coupled nature of drive chassis (1234) and chassis housing (1202). Internal splined rotary bodies (1312) are rotationally supported to a suitable chassis plate (1304, 1306, 1308).

Each drive assembly (1318) associated with articulation section (1240) is coupled to a corresponding articulation band (1248) (see FIG. 36A). Articulation drive assemblies (1318) are configured to convert rotational motion of a corresponding splined shaft (1216) into linear motion of articulation bands (1248) in order to bend articulation section (1240) in accordance with the description herein. Articulation drive assemblies (1318) may have any suitable components as would be apparent to one skilled in the art in view of the teachings herein.

Figure 32:
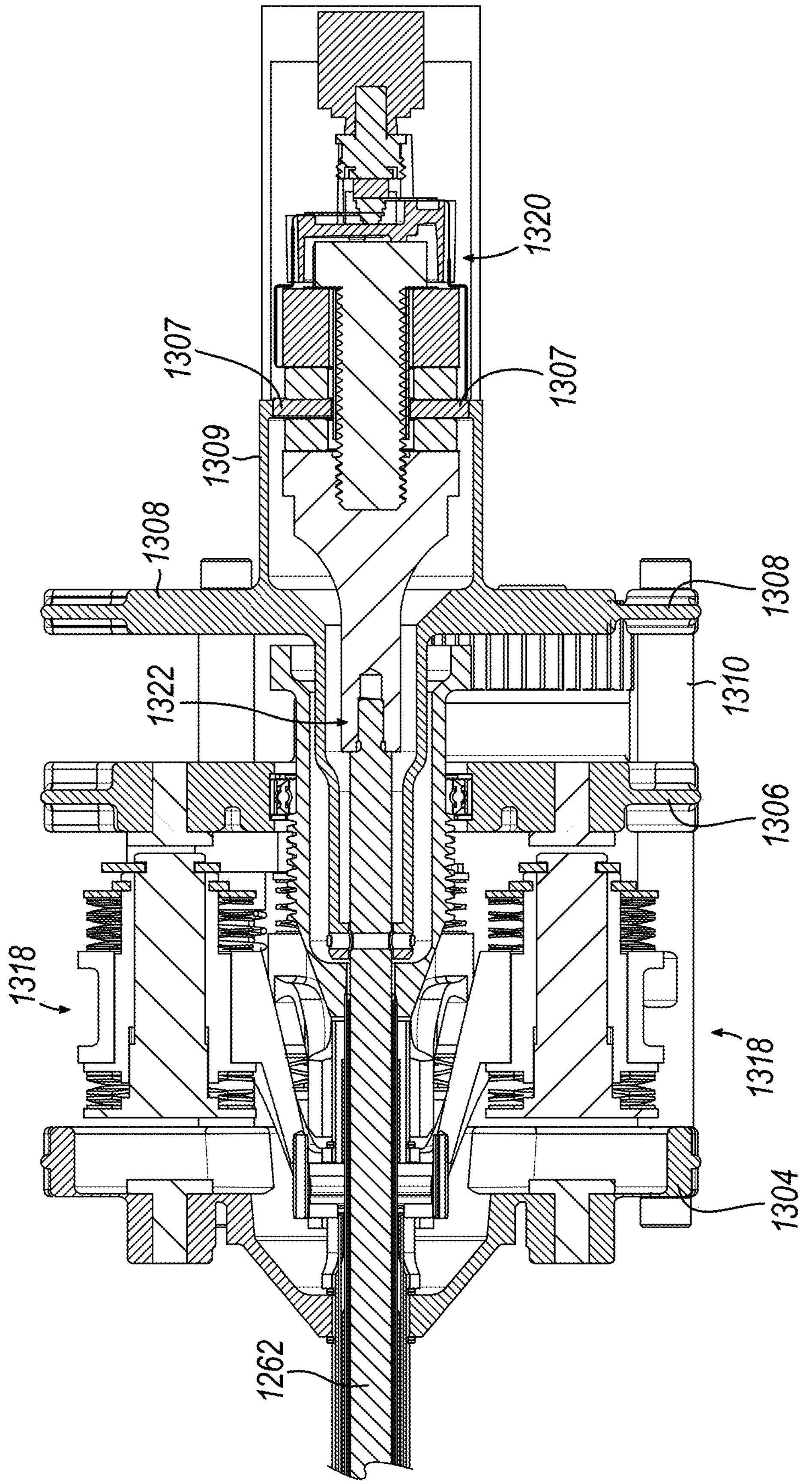
FIG. 32 depicts a cross-sectional view of the drive chassis of FIG. 30, taken along section line 32-32 of FIG. 31.
Figure 34:
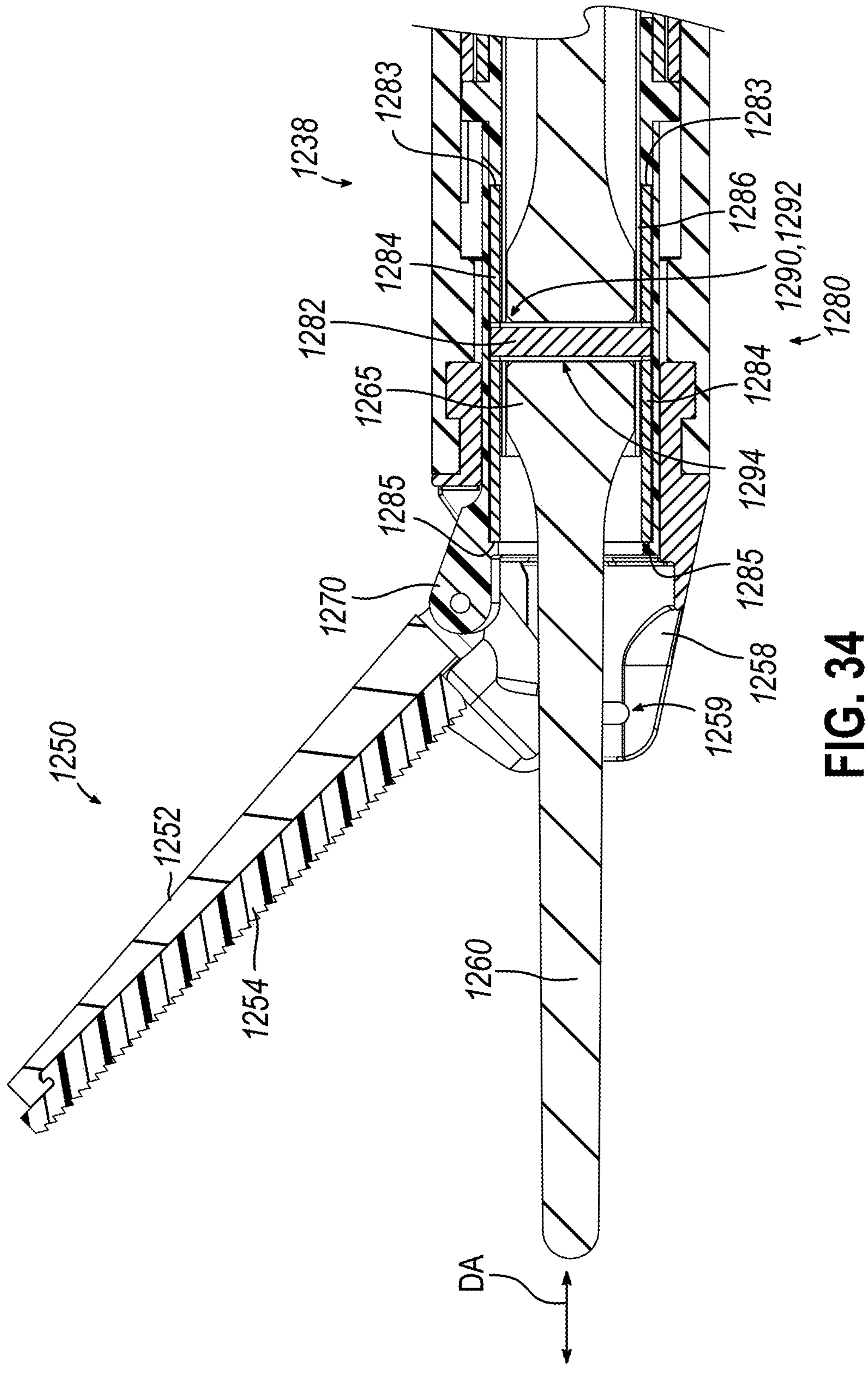
FIG. 34 depicts an enlarged cross-sectional view of the distal end of the shaft assembly and the end effector of FIG. 27A, taken along section line 34-34 of FIG. 33.
Figure 35:
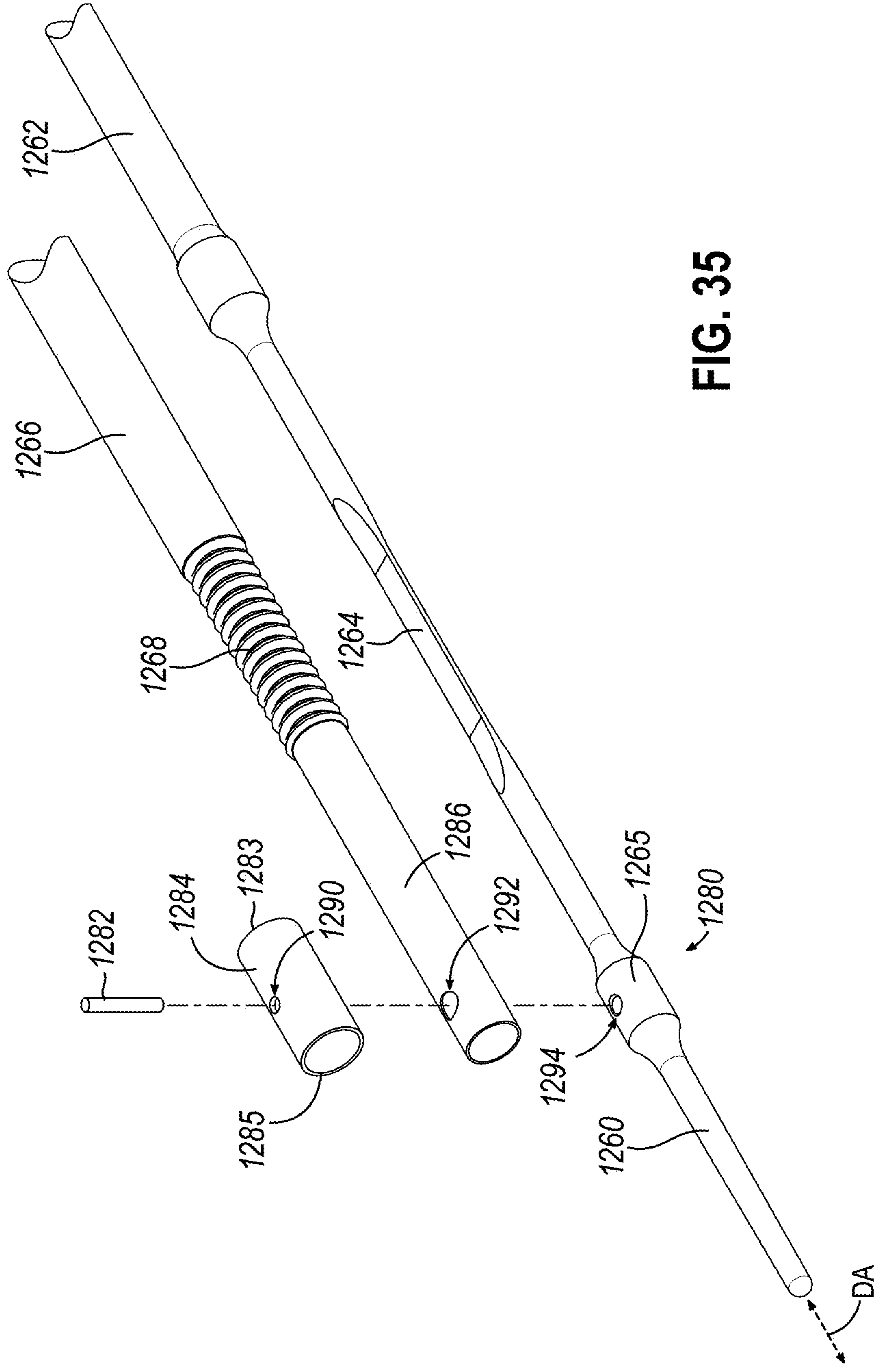
FIG. 35 depicts an exploded perspective view of waveguide and ultrasonic blade of the shaft assembly and end effector of FIG. 27A, respectively, and a waveguide grounding assembly.

Similarly, and with reference to FIGS. 32-34 drive assembly (1318) associated with clamp arm (1252) of end effector (1250) is coupled to one tongue (1258, 1270), while the other tongue (1258, 1270) is longitudinally fixed relative to distal shaft portion (1238) of shaft assembly (1232). Drive assembly (1318) associated with clamp arm (1252) is configured to convert rotational motion of a corresponding splined shaft (1216) into linear motion of tongue (1258, 1270) coupled with clamp arm (1252) in order to open and close clamp arm (1252) in accordance with the description herein. Drive assembly (1318) associated with clamp arm (1252) may have any suitable components as would be apparent to one skilled in the art in view of the teachings herein.

D. Exemplary Distally Grounding Assembly for Waveguide

As mentioned above, it may be desirable to prevent shifting of ultrasonic blade (1260) relative to clamp arm (1252) in the articulated configuration in order to substantially maintain the alignment of ultrasonic blade (1260) and clamp arm (1252) along distal axis (DA) of blade (1260), regardless of the articulated configuration of end effector (1250). FIGS. 34-36B show waveguide grounding assembly (1280) configured to keep ultrasonic blade (1260) and clamp arm (1252) of end effector (1250) as substantially aligned relative to each other along distal axis (DA) of blade (1260), regardless of the articulated configuration of end effector (1250).

Waveguide grounding assembly (1280) includes a grounding pin (1282), a flange sleeve (1284), a distal portion (1286) of waveguide sheath (1266), and distal flange (1265) of waveguide (1262). Flange sleeve (1284) and distal portion (1286) of waveguide sheath (1266) each define a hollow interior dimensioned to house distal flange (1265) such that flange sleeve (1284) covers distal portion (1286) of waveguide sheath (1266) and distal flange (1265) of waveguide (1262).

Flange sleeve (1284) includes an open proximal end (1283) and an open distal end (1285). Open ends (1283, 1285) are dimensioned to abut against interior surfaces of distal shaft portion (1238) to substantially longitudinally fix flange sleeve (1284) relative to distal shaft portion (1238).

Flange sleeve (1284) may also be dimensioned to abut against the interior of distal shaft portion (1238) with sufficient force in order to provide a suitable compressive force onto distal flange (1265). A suitable compressive force distributed from flange sleeve (1284) onto distal flange (1265) may help promote operative acoustic properties of waveguide (1262) such that waveguide (1262) may transmit suitable ultrasonic vibrations to blade (1260) while end effector (1250) is in a suitable articulated configuration. Flange sleeve (1284) may have any suitable geometry as would be apparent to one skilled in the art in view of the teachings herein. Flange sleeve (1284) may be formed of any suitable material as would be apparent to one skilled in the art in view of the teachings herein.

Flange sleeve (1284) and distal end (1286) of waveguide sheath (1266) each define a pair of respective pin holes (1290, 1292) dimensioned to house grounding pin (1282). Additionally, distal flange (1265) defines a pin hole (1294) dimensioned to also house grounding pin (1282). In particular, grounding pin (1282) is dimensioned to be housed within each pin hole (1290, 1292, 1294), when pin holes (1290, 1292, 1294) are suitably aligned, to thereby promote longitudinally fixing waveguide (1262) and blade (1260) relative to flange sleeve (1284) via grounding pin (1282) and pin holes (1290, 1294).

Since flange sleeve (1284) is substantially longitudinally fixed within the interior of distal shaft portion (1238) in accordance with the description above, waveguide (1262) and blade (1260) also remain substantially longitudinally fixed to distal shaft portion (1238) via interaction between grounding pin (1282) and sleeve (1284). In other words, waveguide grounding assembly (1280) promotes longitudinally fixing blade (1260) relative to distal shaft portion (1238) along distal axis (DA) defined by blade (1260).

Additionally, since clamp arm (1252) is pivotally coupled to a tongue (1258, 1270) that is substantially fixed to distal shaft portion (1238), a pivotable coupling at which blade (1260) pivots relative to blade (1260) remains substantially fixed relative to distal shaft portion (1238). Keeping blade (1260) and a pivotable coupling at which blade (1260) pivots both substantially fixed relative to distal shaft portion (1238) may help keep clamp arm (1252) suitably aligned with blade (1260) as end effector (1250) transitions between the straight configuration (FIG. 36A) and an articulated configuration (FIG. 36B). In other words, waveguide grounding assembly (1280) may help keep ultrasonic blade (1260) and clamp arm (1252) substantially aligned relative to each other along distal axis (DA) of blade (1260) during articulation.

FIGS. 36A-36B show an exemplary use of waveguide grounding assembly (1280) to keep clamp arm (1252) suitably aligned with blade (1260) as end effector transitions between a straight configuration (FIG. 36A) and an articulated configuration (FIG. 36B). While in the straight configuration, blade (1260) and clamp arm (1252) may be suitably aligned with each other. Once the operate drives end effector (1250) into the articulated configuration in accordance with the description herein, the curve length which flexible portion (1264) bends while articulation section (1240) is in the articulated configuration may be different than the curve length of the various elements that connect to and deflect clamp arm (1252) while articulation section (1240) is in the articulated configuration. This difference in curve length may try to drive or shift blade (1260) proximally relative to clamp arm (1252) compared to the position of blade (1260) relative to clamp arm (1252) in the straight configuration. However, since waveguide grounding assembly (1280) keeps blade (1260) and clamp arm (1252) substantially aligned relative to each other along the distal axis (DA) of blade (1260) during articulation, waveguide (1262) is inhibited from moving relative to clamp arm (1252) along distal axis (DA), thereby keeping blade (1260) and clamp arm (1252) substantially aligned with each other while in both the articulated configuration, as compared to the straight configuration.

Due to design constraints in previous robotically controlled surgical instruments, rotation about longitudinal axis (LA) of elements similar to proximal shaft portion (1236), articulation section (1240), distal shaft portion (1238), and end effector (1250), may have been performed relative to the drive elements similar to drive chassis (1234). In other words, rotation of end effector and about longitudinal axis (LA) would have been the chassis converting rotational movement of the robotic arm drivers into operative movement of the end effector. Therefore, such previously robotically controlled surgical instruments may present difficulties in fixing transducer assemblies to the mechanical grounding framing components of drive assemblies, (such as proximal chassis plate (1308)), as this would inhibit rotation of an acoustic drivetrain relative to drive elements similar to drive chassis (1234) described above.

In order to promote rotation of the acoustic drivetrain about longitudinal axis (LA) in previous robotically controlled surgical instruments, a pin may thus be inserted through the acoustic waveguide and proximal shaft portion, such that rotation of the proximal shaft portion relative to driving elements would drive corresponding rotation of the acoustic drivetrain via the proximal pin. Since this pin was proximal to the bending components of articulation section and the bending of the flexible portion of waveguide, this proximal pin would not be able to ground the clamp arm relative to the ultrasonic blade along a distal axis defined by the blade during articulation.

Previously, if a pin was inserted through a distal shaft portion (distal to flexible portion of waveguide) to accomplish the same rotational movement of the acoustic drivetrain and ground the clamp arm relative to the blade, the torsional forces that needed to be transmitted to the proximal end of the acoustic drivetrain may have torsionally twisted the flexible portion of waveguide about the longitudinal axis of the flexible portion of waveguide, thereby potentially damaging waveguide.

Therefore, since ultrasonic instrument (1230) has an acoustic drivetrain that rotates with drive chassis (1234) via coupling flange (1307), instead of relative to drive chassis (1234) about longitudinal axis (LA), a proximal pin that transmits rotational forces from proximal shaft portion (1236) onto acoustic drivetrain is not required. With no proximal pin required to suitably transmit rotational forces to the acoustic drivetrain, distal grounding pin (1282) may be the only pin required to extend within waveguide (1262). This may reduce design/manufacturing complications for instrument

IV. Exemplary Feedback System for Out-of-Plane Motion

As shown between FIGS. 8A-8B, FIGS. 25A-25B, and FIGS. 36A-36B, articulation section (164, 1240) may be configurated to deflect end effector (116, 1250) along only a single plane of motion. In some instances, articulation limited to a single plane of motion may make it difficult for an operator to control instrument (14, 1230).

For instance, an operator may be controlling instrument (14, 1230) and a robotic arm via a user interface device (UID) that seemingly accommodates for articulation of end effector (116, 1250) along more than a single plane of motion. When the operator inputs a command into the UID for articulation of end effector (116, 1250) in a plane that is unachievable by instrument (14, 1330), the operator may believe end effector (116, 1250) is in an inaccurate position, or become confused or frustrated as to why end effector (116, 1250) is not articulating in the desired, but unachievable, plane of articulation.

Therefore, it may be desirable to communicate to the operator that the movement which the operator desires to control instrument (14, 1230) is unachievable. For instance, a controller of a user interface device (UID) may be configured to provide haptic feedback to the operator when the operator attempts to articulate end effector (116, 1250) along a plane of articulation that is unachievable. Additionally, a display screen may also show an "out of range indication" to visually display to the operator that they plane of articulation is not achievable. During exemplary use, when the operator tries to control instrument (14, 1230) via the UID with motion that is unachievable, the operator will not assume the unachievable movement has occurred (leading to inaccurate positioning of end effector (116, 1250), or wonder why the commands are not being followed by the robotic instrument (leading to unnecessary delays in the procedure).

V. Exemplary Ultrasonic Surgical Instrument with Multiplanar Articulation Joint In some instances, with respect to FIGS. 6A-8B, it may be desirable to guide deflection of end effector (116) at least in part according to various properties and/or constraints associated with components passing through articulation section (164) during use. By way of example, greater variability in such deflection, such as by increased articulation along shaft assembly (114), may increase strain on one or more flexible components within articulation section (164). Articulation section (164) may thus be desirably articulated via links (168, 170, 172) in one example to accurately and precisely guide movement of flexible components within articulation section (164) while reducing strain that may otherwise occur through these flexible components, such as acoustic waveguide (156).

By way of further example, greater variability of deflection along shaft assembly (114) may incorporate one or more multiplanar articulation sections (2164) with respective links (2168, 2170, 2172*a*-*b*, 2173) for guiding a multi-flex acoustic waveguide (2156) through greater degrees of freedom than acoustic waveguide (156) of ultrasonic surgical instrument (14). To this end, shaft assembly (114) with end effector (116) is more generally configured to move longitudinally along longitudinal axis (161), laterally perpendicular to longitudinal axis (161), and transversely perpendicular to longitudinal axis (161) as well as rotate end effector (116) about longitudinal axis (161) and pivot end effector (116) along a plane, which may be pitch or yaw depending on the relative position of end effector (116). While such movement provides five degrees of freedom to end effector (116) via acoustic waveguide (156) during use, any one or more of the multiplanar articulation sections (2164, 2164*a*) and/or acoustic waveguide (2156) described below are configured to enable an end effector (2116) to pivot through an additional plane for six degrees of freedom. Multiplanar articulation sections (2164, 2164*a*) and/or acoustic waveguide (2156) are thus configured to guide deflection of end effector (2116) while reducing strain on acoustic waveguide (2156). While the following provides additional details with respect to an example of an ultrasonic surgical instrument (2014) having a single multiplanar articulation section (2164) as shown in FIGS. 37A-45, the invention is not intended to be unnecessarily limited to one or more of such articulation sections (2164). Indeed, any alternative articulation section including but not limited to articulation section (2164*a*) shown in FIG. 69 may be used alone or in combination for supporting acoustic waveguides having one or more flexible portions, such as acoustic waveguide (2156) described below in greater detail. In addition, like numbers below indicate like features described above in greater detail.

A. First Exemplary Multiplanar Articulation Section

FIGS. 37A-45 show another example of an ultrasonic surgical instrument (2014) having an instrument base (not shown), which may be similar to instrument base (76) (see FIGS. 5-6B), coupled to a distally extending multiplanar shaft assembly (2114) with end effector (2116). End effector (2116) of the present example includes a clamp arm (2144) and an ultrasonic blade (2146). Clamp arm (2144) has a clamp pad (2148) secured to an underside of clamp arm (2144), facing blade (2146). Clamp arm (2144) is pivotally secured to a distally projecting tongue (2150) of shaft assembly (2114). Clamp arm (2144) is operable to selectively pivot toward and away from blade (2146) to selectively clamp tissue between clamp arm (2144) and blade (2146). A pair of arms (2151) extend transversely from clamp arm (2144) and are secured to respective closure cables (2152) configured to longitudinally actuate to pivot clamp arm (2144) as indicated by an arrow (2153) between a closed position shown in FIG. 37A and an open position shown in FIG. 37B. In some versions, clamp arm (2144) may be biased toward one of its open or closed positions, such as via a resilient biasing member (not shown).

Blade (2146) of the present example is operable to vibrate at ultrasonic frequencies in order to effectively cut through and seal tissue. Blade (2146) is positioned at a distal end of an acoustic drivetrain. This acoustic drivetrain includes a transducer assembly (154) (see FIG. 7A) and a multi-flex acoustic waveguide (2156), which includes a flexible portion (2158) configured to provide flexing in more than one plane as discussed below in greater detail. Unless explicitly stated herein, end effector (2116) is constructed and operable as end effector (116) discussed above in greater detail.

Shaft assembly (2114) is similar to shaft assembly (114) discussed above in greater detail, but is configured for multiplanar articulation. More particularly, shaft assembly (2114) includes a proximal shaft portion (2160) extending along a proximal longitudinal axis (2161), a distal shaft portion (2162) distally projecting relative to proximal shaft portion (2160) along a distal longitudinal axis (2163) (and including tongue (2150)), and multiplanar articulation section (2164) extending between proximal and distal shaft portions (2160, 2162) at least partially along a middle longitudinal axis (2165). The instrument base (not shown) may thus be configured to direct articulation of multiplanar articulation section (2164) as discussed below. In this regard, axes (2161, 2163, 2165) may coincide with each other when in a straight configuration, while axis (2165) may be transversely and/or laterally oriented relative to one or both of axes (2161, 2163) when in one or more articulation configurations, as discussed below. Unless explicitly stated herein, shaft assembly (2114) is constructed and operable as shaft assembly (114) discussed above in greater detail.

Articulation section (2164) is configured to selectively position end effector (2116) at various lateral and/or transverse deflection angles relative to longitudinal axis (2161) defined by proximal shaft portion (2160) and/or relative to longitudinal axis (2165) defined by at least a portion of articulation section (2164) itself. Articulation section (2164) may take a variety of forms. In the present example, articulation section (2164) includes a proximal link (2168), a distal link (2170), and a pair of intermediate links (2172*a*, 2172*b*) connected in series between proximal and distal links (2168, 2170) with a middle link (2173) interposed between the pair of intermediate links (2172*a*, 2172*b*). Articulation section (2164) further includes a plurality of proximal articulation cable segments (2174*a-d*) and a plurality of distal articulation cable segments (2175*a-d*) extending along a plurality of respective channels (2176*a-d*, 2177*a-d*) collectively defined through links (2168, 2170, 2172*a-b*, 2173). In the example shown, proximal articulation cable segments (2174*a-d*) are grounded to middle link (2173) while distal articulation cable segments (2175*a-d*) are grounded to distal link (2170). In some versions, pairs of adjacent articulation cable segments (2174*a-d*, 2175*a-d*) may be integrally formed together as a single cable. For example, upper adjacent distal articulation cable segments (2175*a*, 2175*d*) may be integrally formed together as a single cable, lower adjacent distal articulation cable segments (2175*b*, 2175*c*) may be integrally formed together as a single cable, righthand adjacent proximal articulation cable segments (2174*a*, 2174*b*) may be integrally formed together as a single cable, and/or lefthand adjacent proximal articulation cable segments (2174*c*, 2174*d*) may be integrally formed together as a single cable. In any event, links (2168, 2170, 2172*a-b*, 2173) are generally configured to pivot relative to each other upon selective actuation of articulation cable segments (2174*a-d*, 2175*a-d*) to thereby bend articulation section (2164) with flexible portion (2158) of waveguide (2156) therein to achieve one or more articulated states.

Figure 37A:
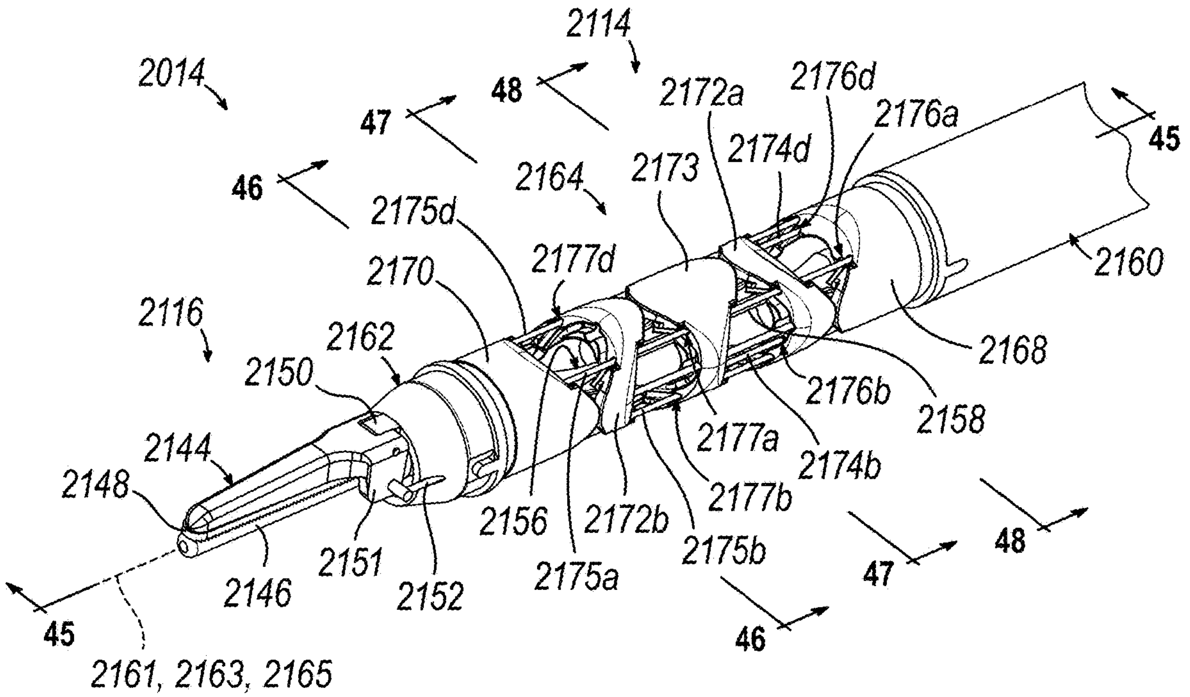
FIG. 37A depicts an enlarged perspective view of another exemplary surgical instrument with an end effector in a closed position and a shaft assembly in a straight configuration.
Figure 37B:
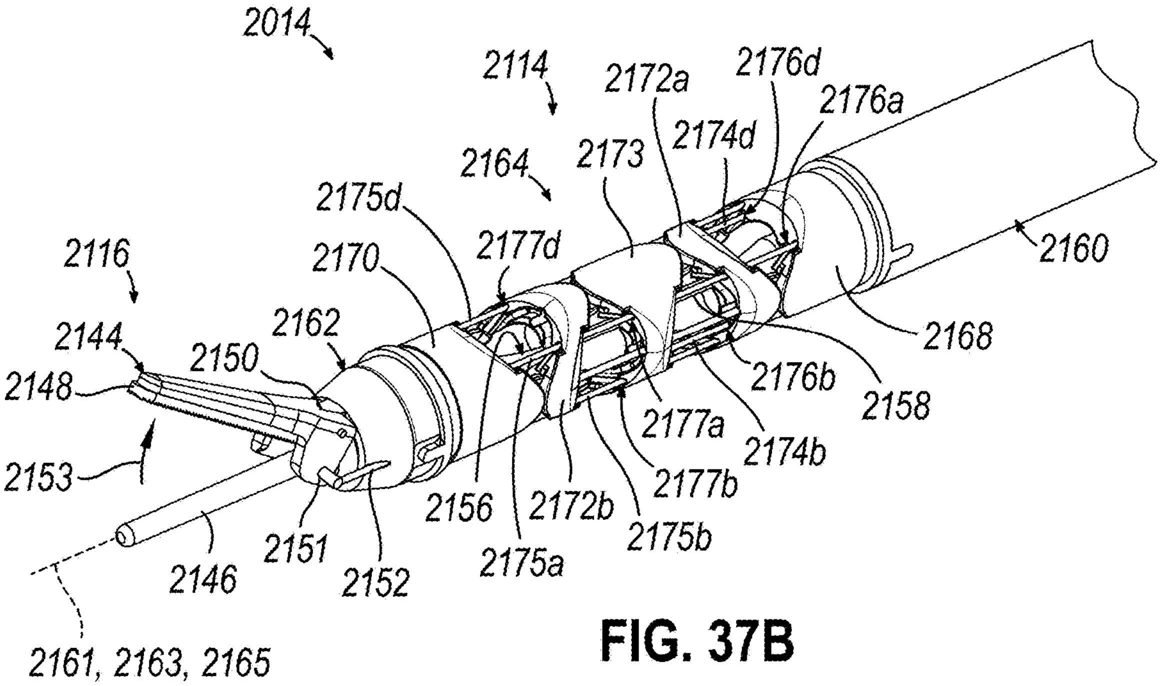
FIG. 37B depicts the enlarged perspective view of the surgical instrument similar to FIG. 37A, but showing the end effector in an open position.

Links (2168, 2170, 2172*a-b*, 2173) of the present example pivotally interlock to secure distal shaft portion (2162) relative to proximal shaft portion (2160) while allowing for deflection of distal shaft portion (2162) relative to longitudinal axis (2161) defined by proximal shaft portion (2160) and relative to longitudinal axis (2165) defined by at least a portion of articulation section (2164) (e.g., by at least middle link (2173)). In this regard, adjacent links (2168, 2170, 2172*a-b*, 2173) pivotally interlock to define corresponding rotational axes. In the present example, proximal link (2168) pivotally interlocks with proximal intermediate link (2172*a*) to define a proximal pitch axis (PP), proximal intermediate link (2172*a*) pivotally interlocks with middle link (2173) to define a proximal yaw axis (PY), middle link (2173) pivotally interlocks with distal intermediate link (2172*b*) to define a distal yaw axis (DY), and distal intermediate link (2172*b*) pivotally interlocks with distal link (2170) to define a distal pitch axis (DP). Thus, as a pair of adjacent proximal articulation cable segments (2174*a-d*) or a pair of distal articulation cable segments (2175*a-d*) translate longitudinally in a first direction and the opposing pair of adjacent proximal articulation cable segments (2174*a-d*) or the opposing pair of distal articulation cable segments (2175*a-d*) translate longitudinally in a second direction, this will cause articulation section (2164) to bend via links (2168, 2170, 2172*a-b*, 2173) thereby laterally and/or transversely deflecting end effector (2116) away from the longitudinal axis (2161) of proximal shaft portion (2160) and/or away from the longitudinal axis (2165) of articulation section (2164) from a straight configuration as shown in FIG. 37A to any one or more of available articulated configurations, such as one or more of those shown in FIGS. 38A-41B.

Figure 38A:
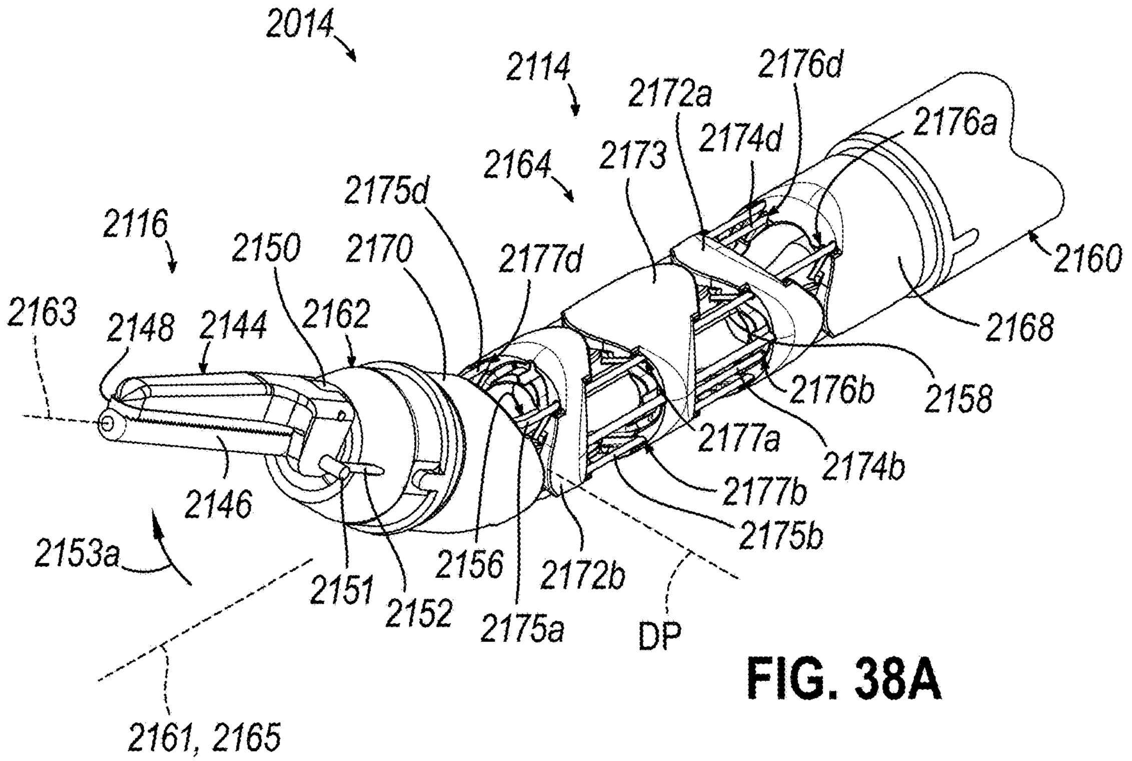
FIG. 38A depicts an enlarged perspective view of the surgical instrument of FIG. 37A with the end effector in a closed position and the shaft assembly in a first articulated configuration.
Figure 38B:
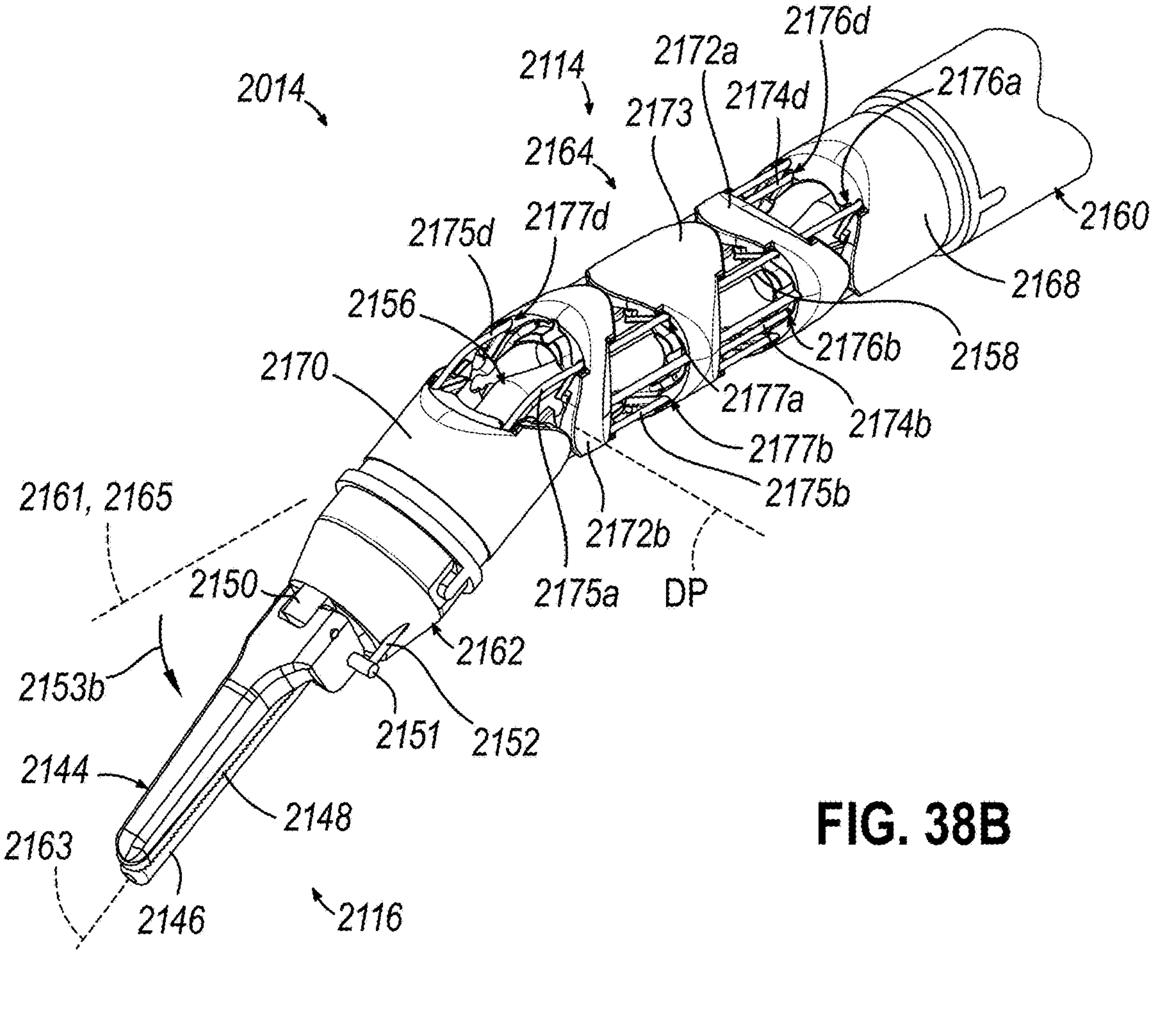
FIG. 38B depicts the enlarged perspective view of the surgical instrument similar to FIG. 38A, but with the shaft assembly in a second articulated configuration.

For example, as upper adjacent distal articulation cable segments (2175*a*, 2175*d*) translate proximally and lower adjacent distal articulation cable segments (2175*b*, 2175*c*) translate distally, distal link (2170) pivots relative to distal intermediate link (2172*b*) about distal pitch axis (DP) to an upwardly pitched configuration as shown in FIG. 38A and indicated by an arrow (2153*a*). As upper adjacent distal articulation cable segments (2175*a*, 2175*d*) translate distally and lower adjacent distal articulation cable segments (2175*b*, 2175*c*) translate proximally, distal link (2170) pivots relative to distal intermediate link (2172*b*) about distal pitch axis (DP) to a downwardly pitched configuration as shown in FIG. 38B and indicated by an arrow (2153*b*). In either case, longitudinal axis (2163) of distal shaft portion (2162) is transversely oriented relative to longitudinal axes (2161, 2165) of proximal shaft portion (2160) and articulation section (2164), which are aligned with each other, such that end effector (2116) is transversely deflected away from longitudinal axes (2161, 2165).

Figure 39A:
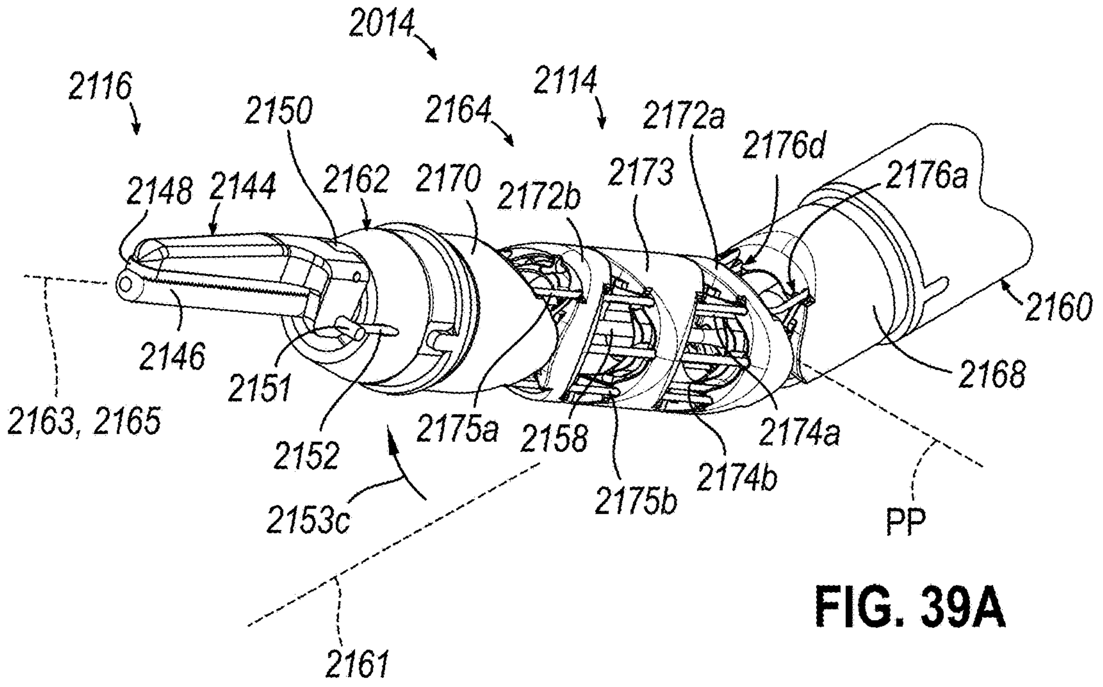
FIG. 39A depicts an enlarged perspective view of the surgical instrument of FIG. 37A with the end effector in a closed position and the shaft assembly in a third articulated configuration.
Figure 39B:
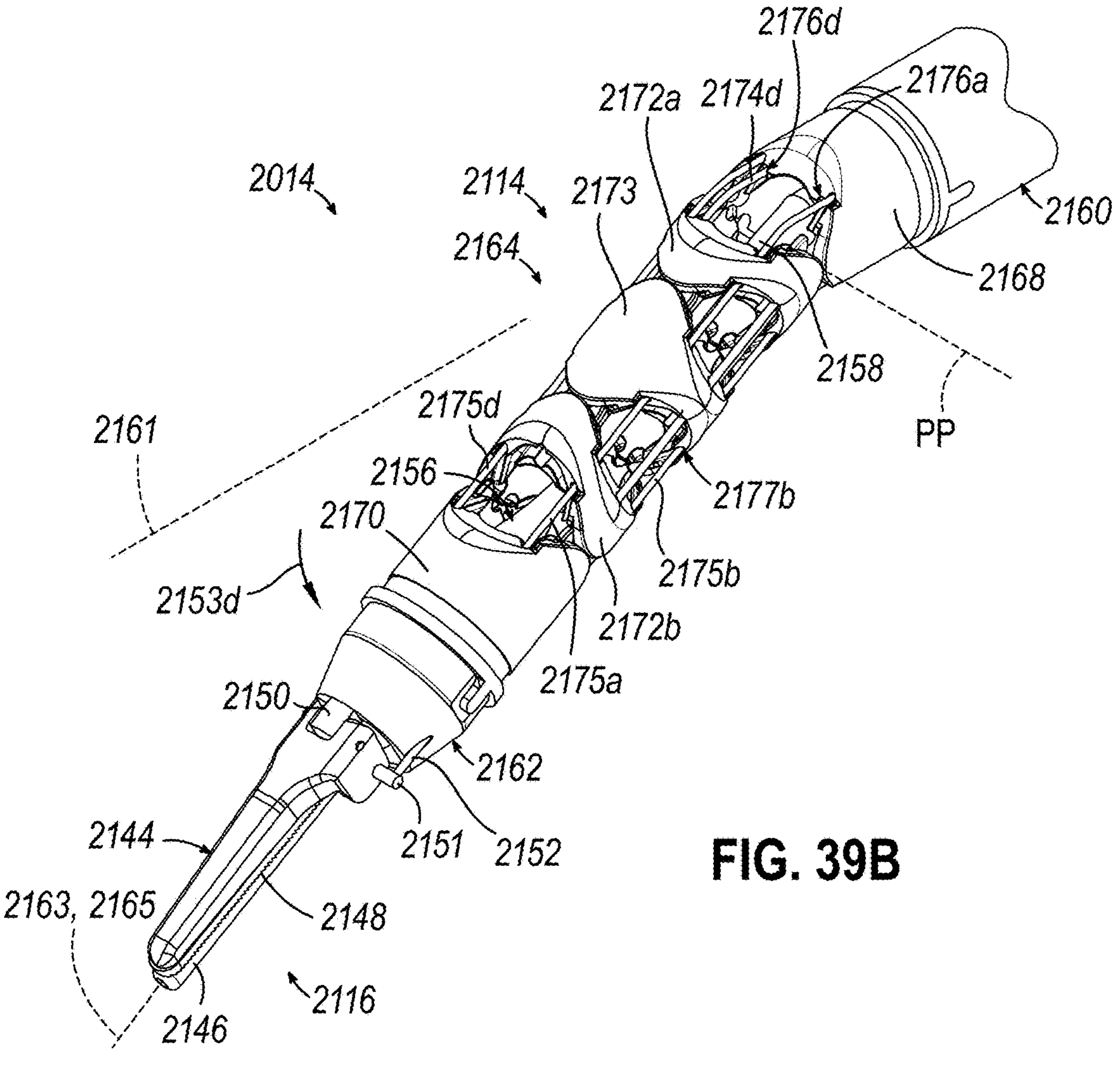
FIG. 39B depicts the enlarged perspective view of the surgical instrument similar to FIG. 39A, but with the shaft assembly in a fourth articulated configuration.

Similarly, as upper adjacent proximal articulation cable segments (2174*a*, 2174*d*) translate proximally and lower adjacent proximal articulation cable segments (2174*b*, 2174*c*) translate distally, proximal intermediate link (2172*a*) pivots relative to proximal link (2168) about proximal pitch axis (PP) to an upwardly pitched configuration as shown in FIG. 39A and indicated by an arrow (2153*c*). As upper adjacent proximal articulation cable segments (2174*a*, 2174*d*) translate distally and lower adjacent proximal articulation cable segments (2174*b*, 2174*c*) translate proximally, proximal intermediate link (2172*a*) pivots relative to proximal link (2168) about proximal pitch axis (PP) to a downwardly pitched configuration as shown in FIG. 39B and indicated by an arrow (2153*d*). In either case, longitudinal axis (2163) of distal shaft portion (2162) is aligned with longitudinal axis (2165) of articulation section (2164) and transversely oriented relative to longitudinal axis (2161) of proximal shaft portion (2160) such that end effector (2116) is transversely deflected away from longitudinal axis (2161).

Figure 40A:
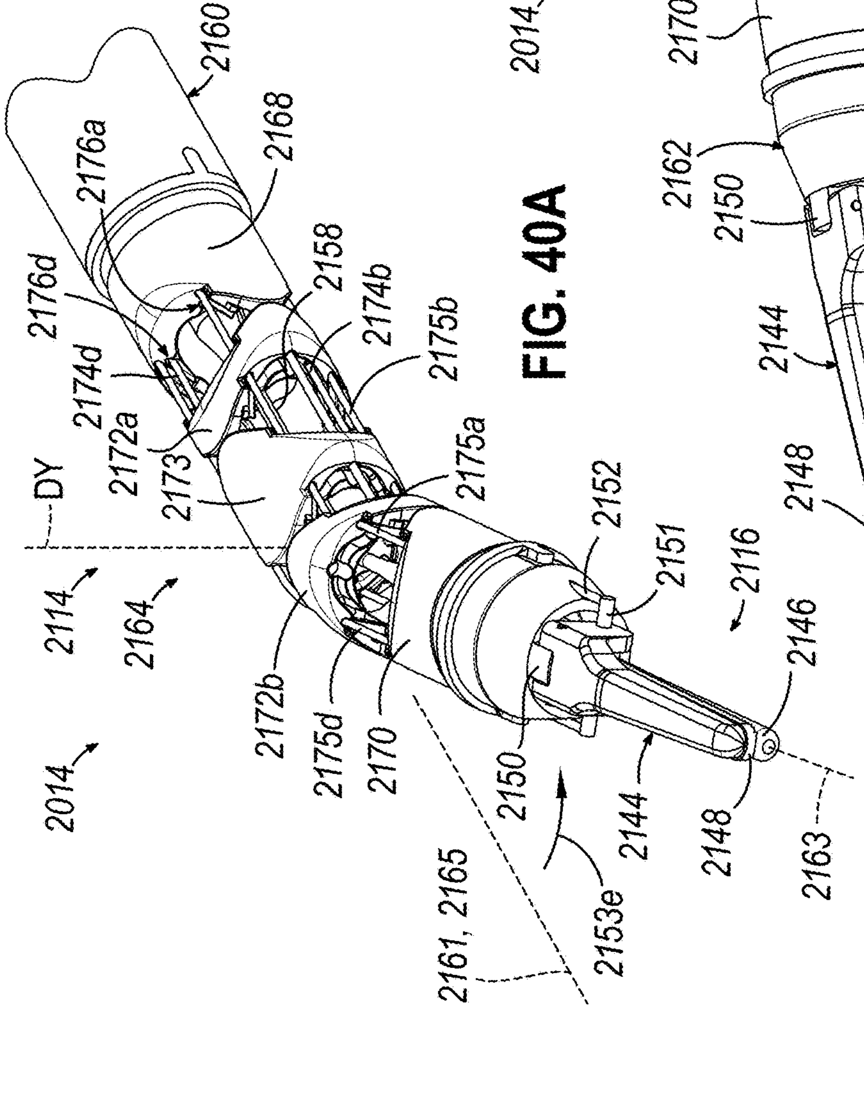
FIG. 40A depicts an enlarged perspective view of the surgical instrument of FIG. 37A with the end effector in a closed position and the shaft assembly in a fifth articulated configuration.
Figure 40B:
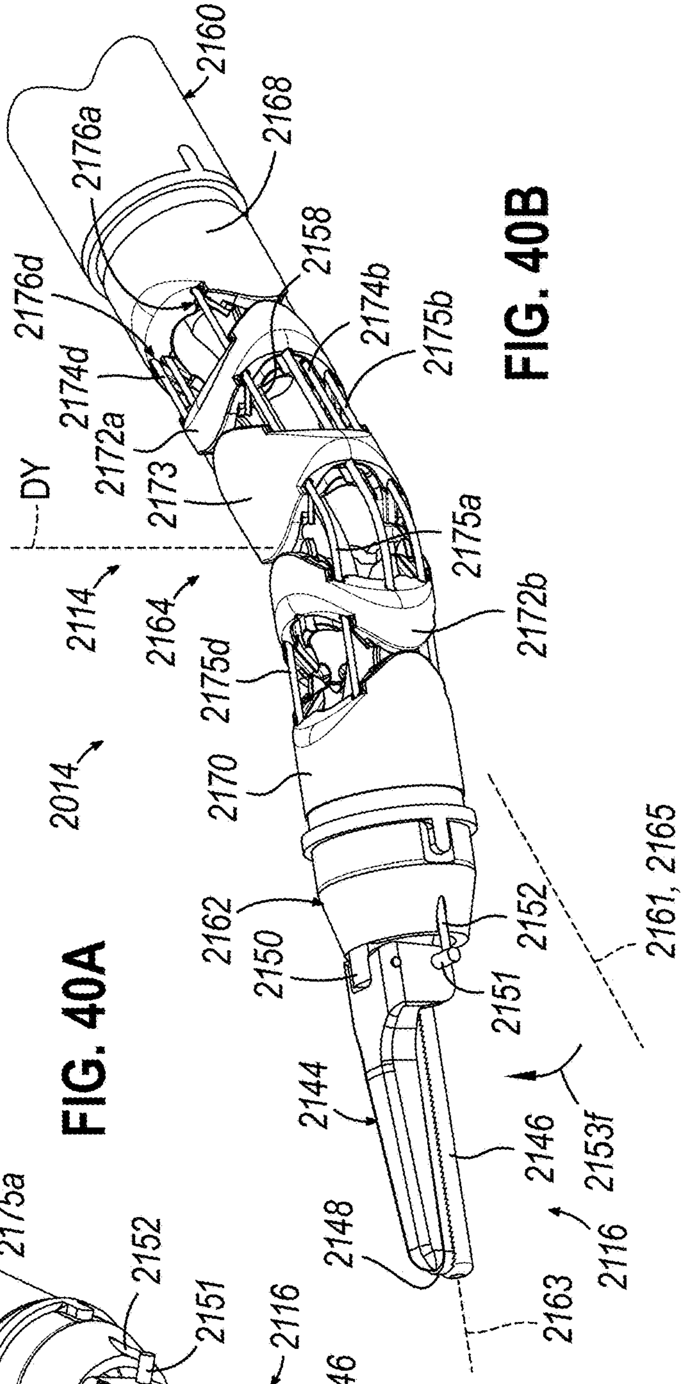
FIG. 40B depicts the enlarged perspective view of the surgical instrument similar to FIG. 40A, but with the shaft assembly in a sixth articulated configuration.

Likewise, as righthand adjacent distal articulation cable segments (2175*a*, 2175*b*) translate proximally and lefthand adjacent distal articulation cable segments (2175*c*, 2175*d*) translate distally, distal intermediate link (2172*b*) pivots relative to middle link (2173) about distal yaw axis (DY) to a rightwardly yawed configuration as shown in FIG. 40A and indicated by an arrow (2153*e*). As righthand adjacent distal articulation cable segments (2175*a*, 2175*b*) translate distally and lefthand adjacent distal articulation cable segments (2175*c*, 2175*d*) translate proximally, distal intermediate link (2172*b*) pivots relative to middle link (2173) about distal yaw axis (DY) to a leftwardly yawed configuration as shown in FIG. 40B and indicated by an arrow (2153*f*). In either case, longitudinal axis (2163) of distal shaft portion (2162) is laterally oriented relative to longitudinal axes (2161, 2165) of proximal shaft portion (2160) and articulation section (2164), which are aligned with each other, such that end effector (2116) is laterally deflected away from longitudinal axes (2161, 2165).

Figures 41A, 41B:
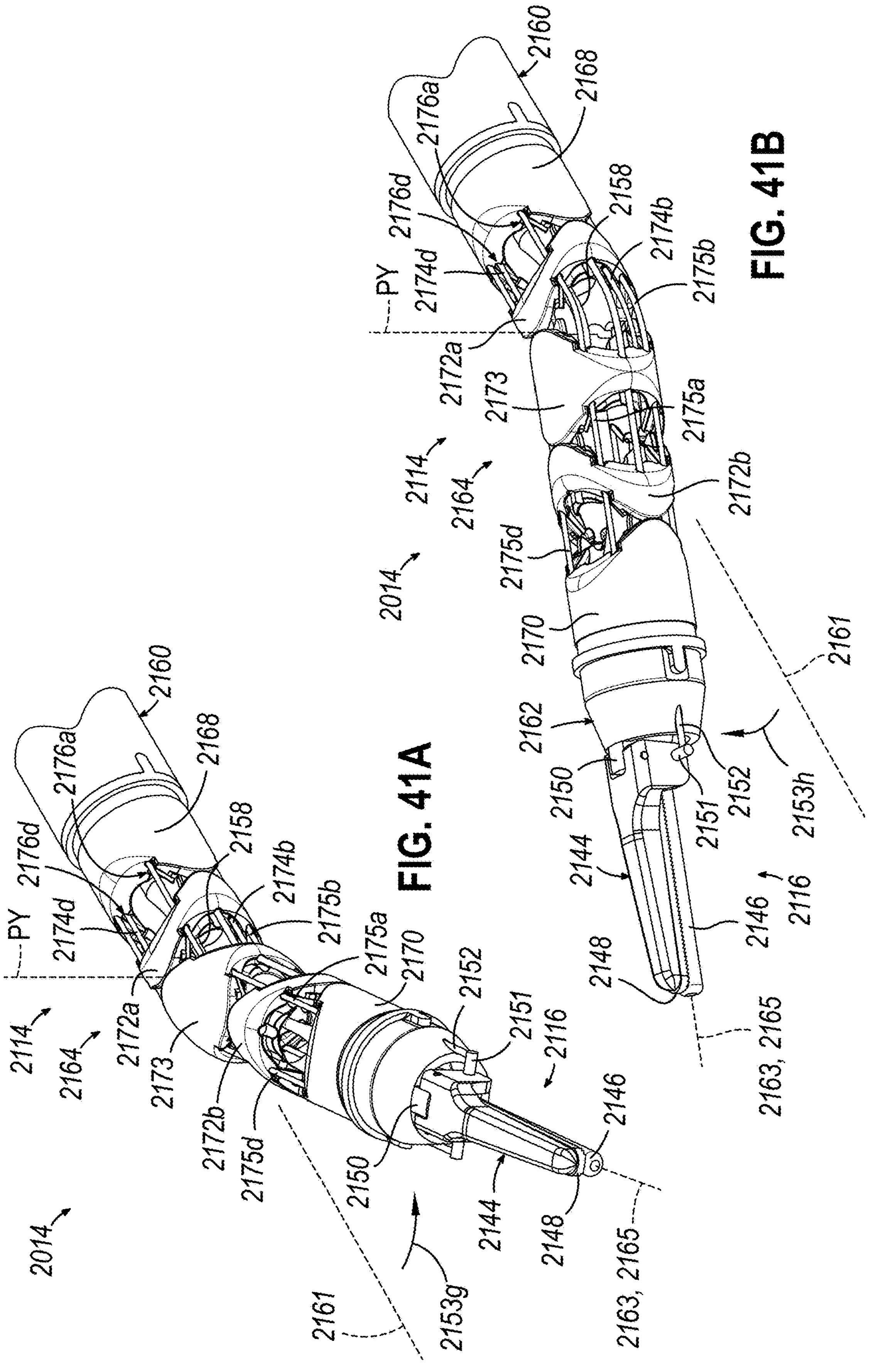
FIG. 41A depicts an enlarged perspective view of the surgical instrument of FIG. 37A with the end effector in a closed position and the shaft assembly in a seventh articulated configuration.
FIG. 41B depicts the enlarged perspective view of the surgical instrument similar to FIG. 41A, but with the shaft assembly in an eighth articulated configuration.

Similarly, as righthand adjacent proximal articulation cable segments (2174*a*, 2174*b*) translate proximally and lefthand adjacent proximal articulation cable segments (2174*c*, 2174*d*) translate distally, middle link (2173) pivots relative to proximal intermediate link (2172*a*) about proximal yaw axis (PY) to a rightwardly yawed configuration as shown in FIG. 41A and indicated by an arrow (2153*g*). As righthand adjacent proximal articulation cable segments (2174*a*, 2174*b*) translate distally and lefthand adjacent proximal articulation cable segments (2174*c*, 2174*d*) translate proximally, middle link (2173) pivots relative to proximal intermediate link (2172*a*) about proximal yaw axis (PY) to a leftwardly yawed configuration as shown in FIG. 41B and indicated by an arrow (2153*h*). In either case, longitudinal axis (2163) of distal shaft portion (2162) is aligned with longitudinal axis (2165) of articulation section (2164) and laterally oriented relative to longitudinal axis (2161) of proximal shaft portion (2160) such that end effector (2116) is laterally deflected away from longitudinal axis (2161).

Articulation section (2164) thus articulates through a pair of planes which are perpendicular to each other. Given the rotational orientation of shaft assembly (2114) as shown in FIGS. 37A-41B, distal link (2170) and proximal intermediate link (2172*a*) of articulation section (2164) each articulate through a pitch plane relative to clamp arm (2144), and distal intermediate link (2172*b*) and middle link (2173) of articulation section (2164) each articulate through a yaw plane relative to clamp arm (2144). However, it will be appreciated that such planes change relative to clamp arm (2144) and/or as oriented in FIGS. 37A-41B, such that the invention is not intended to be unnecessarily limited to the yaw and pitch planes as shown in the present example.

Figure 42:
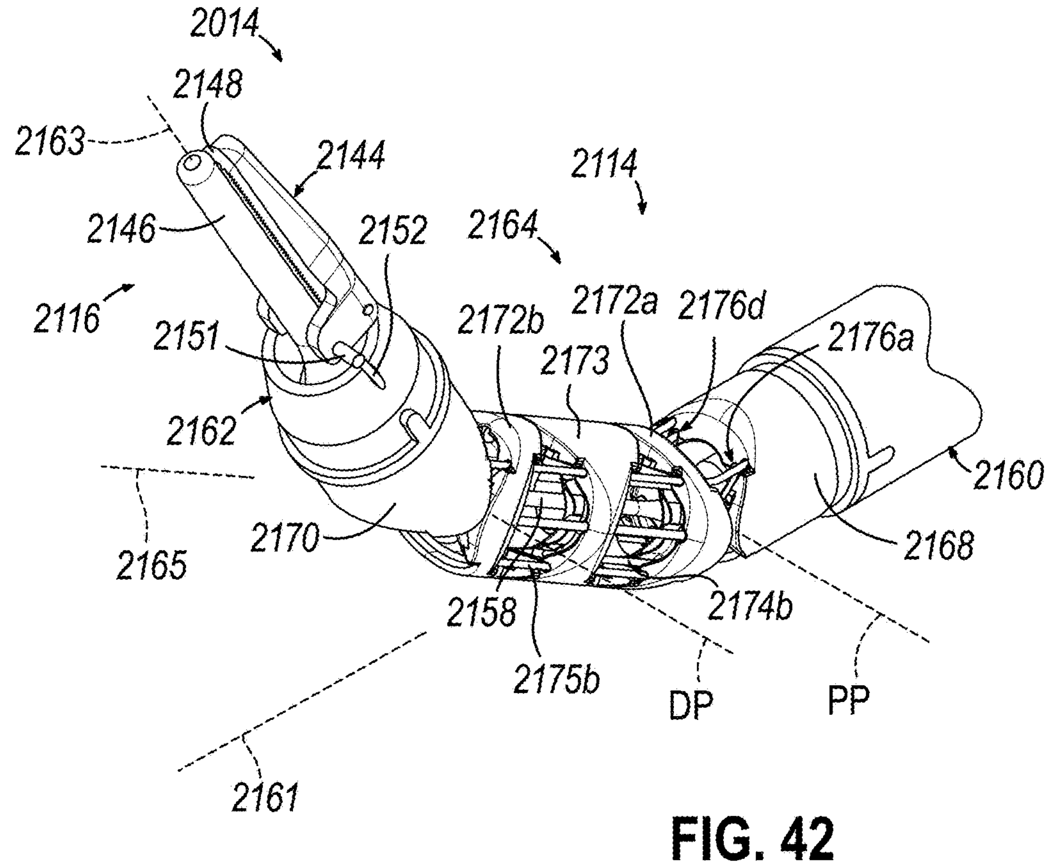
FIG. 42 depicts an enlarged perspective view of the surgical instrument of FIG. 37A with the end effector in a closed position and the shaft assembly in a first dual articulated configuration.
Figure 43:
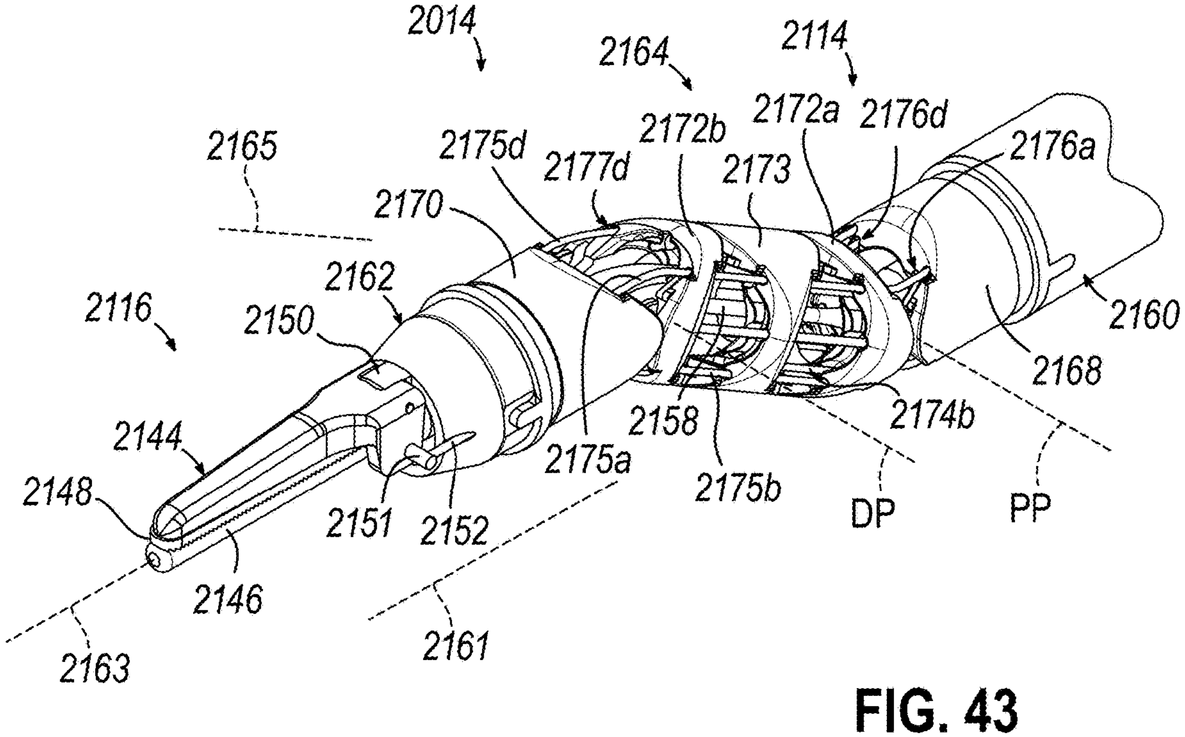
FIG. 43 depicts an enlarged perspective view of the surgical instrument of FIG. 37A with the end effector in a closed position and the shaft assembly in a second dual articulated configuration.
Figure 44:
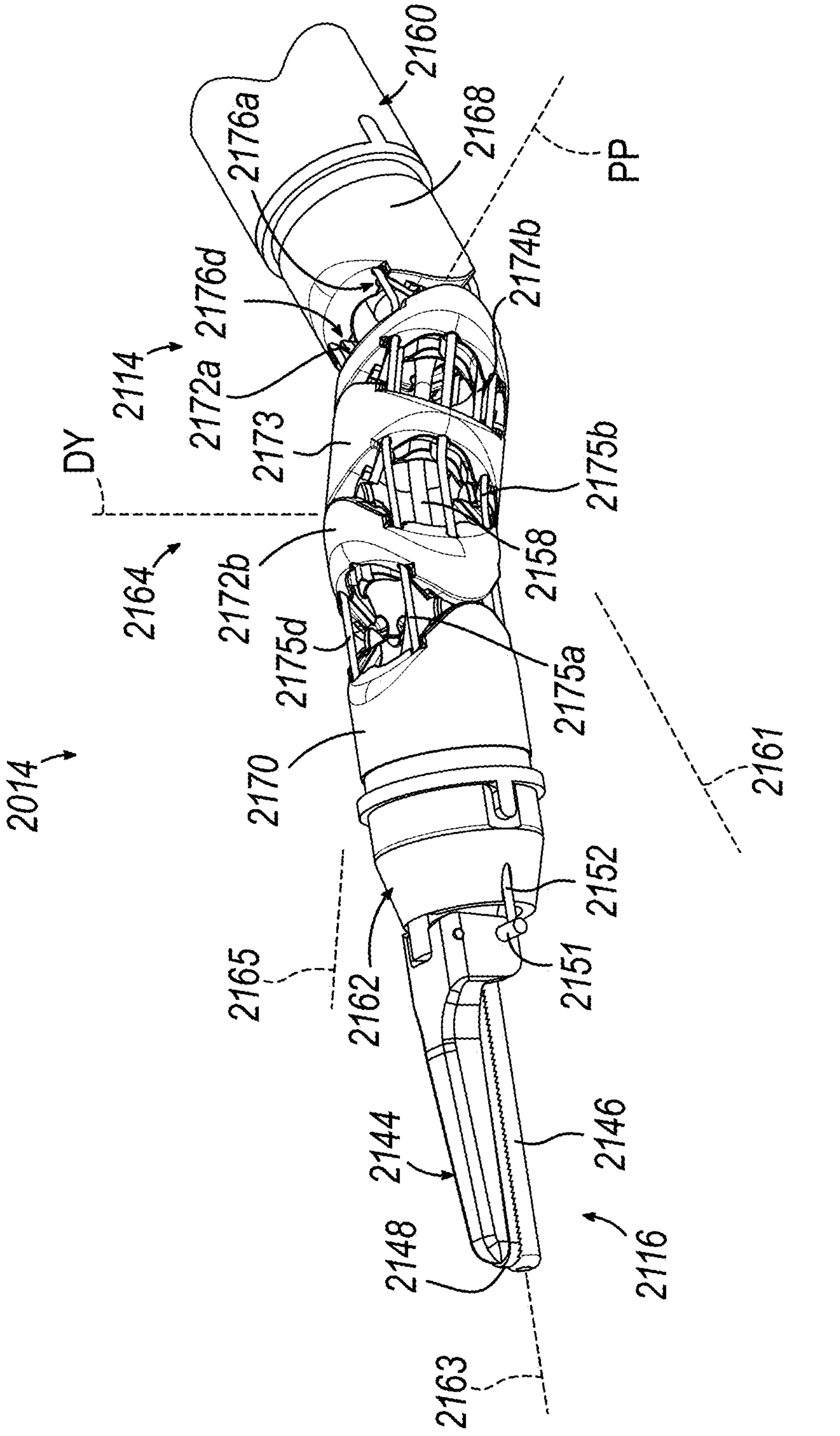
FIG. 44 depicts an enlarged perspective view of the surgical instrument of FIG. 37A with the end effector in a closed position and the shaft assembly in a third dual articulated configuration.

FIGS. 42-44 show various examples of dual articulation for articulation section (2164) such that articulation section (2164) is bent via links (2168, 2170, 2172*a*-*b*, 2173) at multiple (e.g., two) discrete longitudinal positions along the length of articulation section (2164).

FIG. 42 shows proximal intermediate link (2172*a*) upwardly pitched relative to proximal link (2168) about proximal pitch axis (PP) (e.g., via proximal translation of upper adjacent proximal articulation cable segments (2174*a*, 2174*d*) and distal translation of lower adjacent proximal articulation cable segments (2174*b*, 2174*c*)), and further shows distal link (2170) upwardly pitched relative to distal intermediate link (2172*b*) about distal pitch axis (DP) (e.g., via proximal translation of upper adjacent distal articulation cable segments (2175*a*, 2175*d*) and distal translation of lower adjacent distal articulation cable segments (2175*b*, 2175*c*)). In this case, longitudinal axis (2165) of articulation section (2164) is transversely oriented in one angular direction relative to longitudinal axis (2161) of proximal shaft portion (2160) and longitudinal axis (2163) of distal shaft portion (2162) is transversely oriented in the same angular direction relative to longitudinal axis (2165) of articulation section (2164). Thus, end effector (2116) may be selectively upwardly pitched relative to the longitudinal axis (2161) of proximal shaft portion (2160) to a greater degree than that which may be achieved by pitching about one of the proximal or distal pitch axes (PP, DP) alone. While the present example has longitudinal axes (2163, 2165) transversely oriented for upward pitching, longitudinal axes (2163, 2165) may be transversely oriented for downward pitching, or may be laterally oriented for either rightward or leftward yawing.

FIG. 43 shows proximal intermediate link (2172*a*) upwardly pitched relative to proximal link (2168) about proximal pitch axis (PP) (e.g., via proximal translation of upper adjacent proximal articulation cable segments (2174*a*, 2174*d*) and distal translation of lower adjacent proximal articulation cable segments (2174*b*, 2174*c*)), and further shows distal link (2170) downwardly pitched relative to distal intermediate link (2172*b*) about distal pitch axis (DP) (e.g., via distal translation of upper adjacent distal articulation cable segments (2175*a*, 2175*d*) and proximal translation of lower adjacent distal articulation cable segments (2175*b*, 2175*c*)). In this case, longitudinal axis (2165) of articulation section (2164) is transversely oriented at an angle in one angular direction relative to longitudinal axis (2161) of proximal shaft portion (2160) and longitudinal axis (2163) of distal shaft portion (2162) is transversely oriented at the same angle in the opposite angular direction relative to longitudinal axis (2165) of articulation section (2164). Thus, end effector (2116) may be selectively transversely offset from the longitudinal axis (2161) of proximal shaft portion (2160) while being oriented generally parallel thereto. While the present example has longitudinal axes (2163, 2165) transversely oriented at the same angle in opposite angular directions, one or both axes (2163, 2165) may have any relative angular orientation and are not intended to be limited to the angular orientation as shown and described herein.

FIG. 44 shows proximal intermediate link (2172*a*) upwardly pitched relative to proximal link (2168) about proximal pitch axis (PP) (e.g., via proximal translation of upper adjacent proximal articulation cable segments (2174*a*, 2174*d*) and distal translation of lower adjacent proximal articulation cable segments (2174*b*, 2174*c*)), and further shows distal intermediate link (2172*b*) yawed leftwardly relative to middle link (2173) about distal yaw axis (DY) (e.g., via distal translation of righthand adjacent distal articulation cable segments (2175*a*, 2175*b*) and proximal translation of lefthand adjacent distal articulation cable segments (2175*c*, 2175*d*). In this case, longitudinal axis (2165) of articulation section (2164) is transversely oriented relative to longitudinal axis (2161) of proximal shaft portion (2160) and longitudinal axis (2163) of distal shaft portion (2162) is laterally oriented relative to longitudinal axis (2165) of articulation section (2164). Thus, end effector (2116) may be selectively moved according to at least six degrees of freedom.

It will be further appreciated that any desired articulation and combination of respective articulations may be similarly used. Again, the invention is not intended to be unnecessarily limited to the particular angles of articulation shown in the yaw and pitch planes of the present example.

Figure 45:
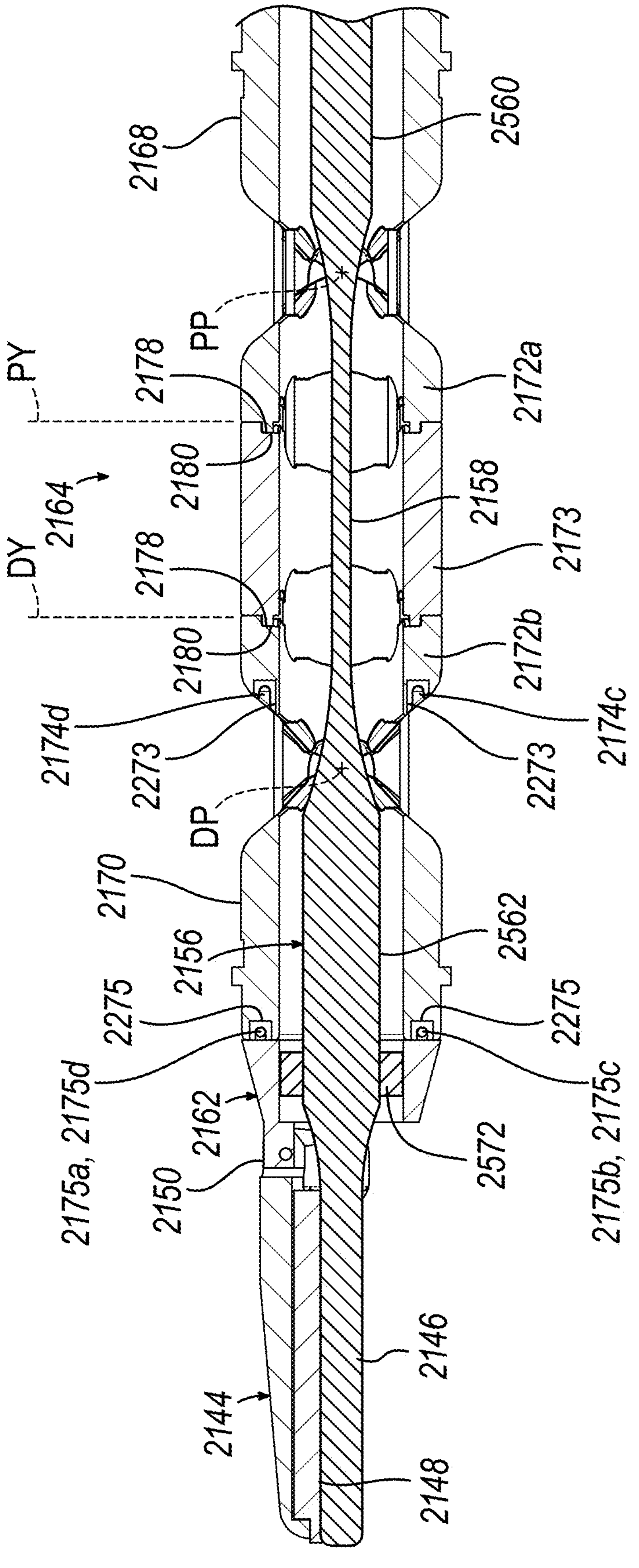
FIG. 45 depicts a cross sectional view of a distal portion of the surgical instrument of FIG. 37A taken along section line 45-45 of FIG. 37A.
Figure 46:
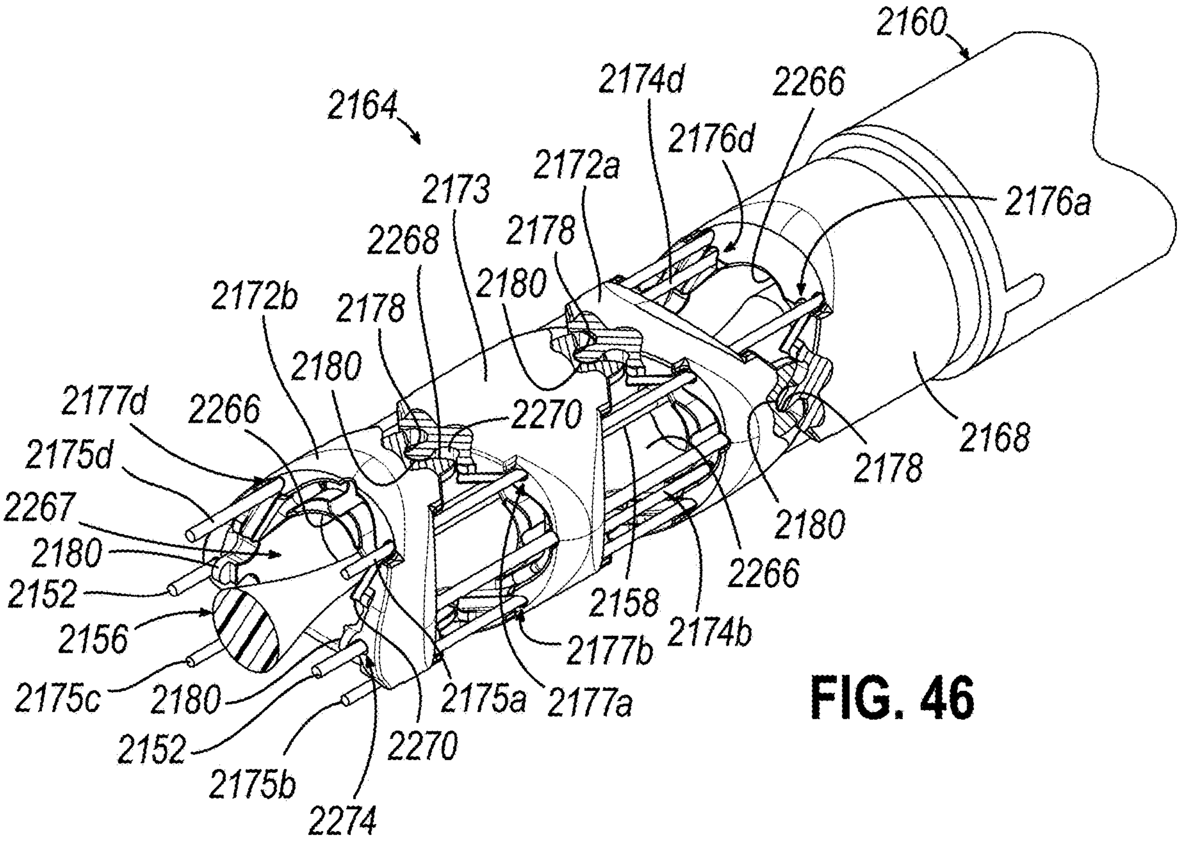
FIG. 46 depicts a sectional perspective view of the multiplanar articulation section of FIG. 37A taken along section line 46-46 of FIG. 37A and having various components removed for additional clarity.
Figure 47:
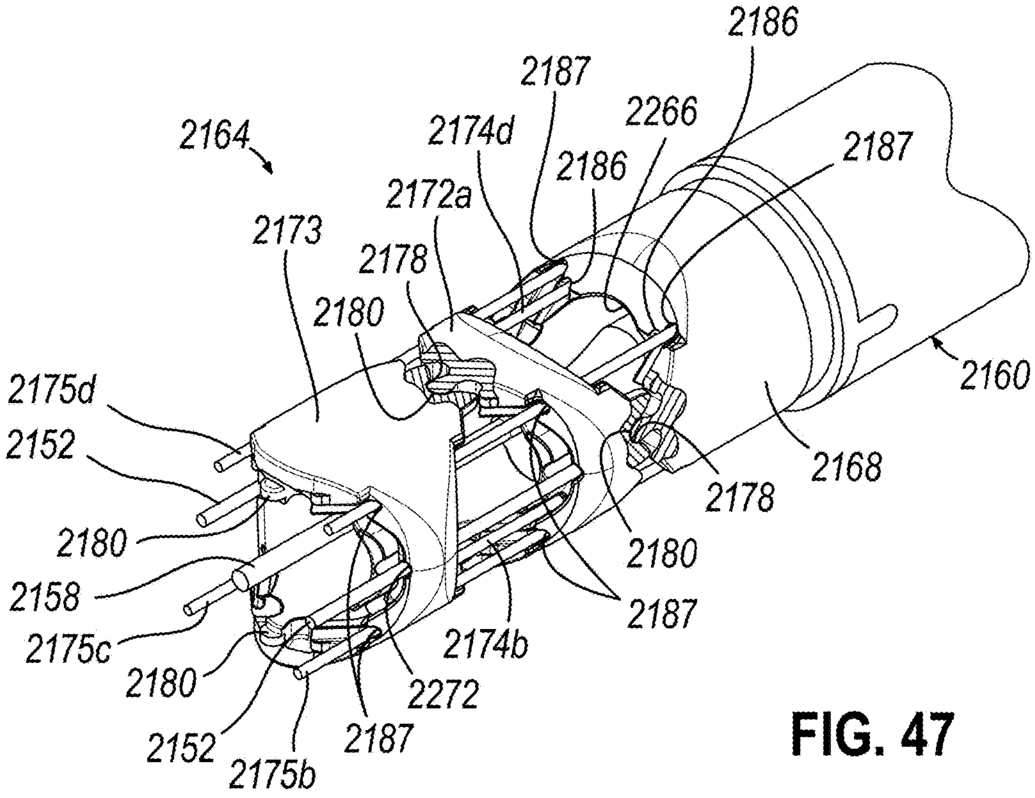
FIG. 47 depicts a sectional perspective view of the multiplanar articulation section of FIG. 37A taken along section line 47-47 of FIG. 37A and having various components removed for additional clarity.
Figure 48:
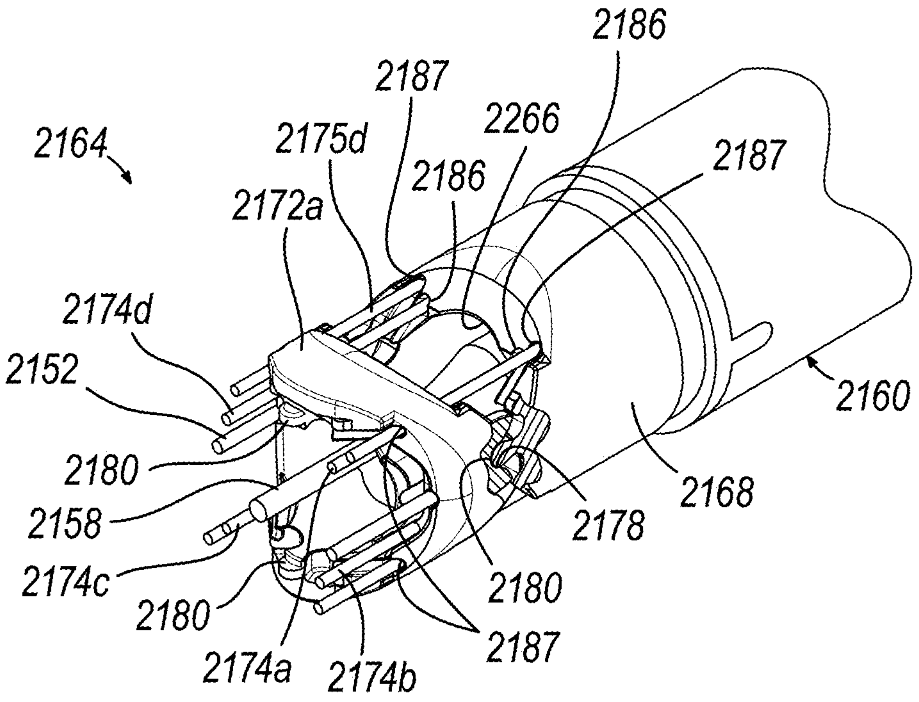
FIG. 48 depicts a sectional perspective view of the multiplanar articulation section of FIG. 37A taken along section line 48-48 of FIG. 37A and having various components removed for additional clarity.
Figure 49:
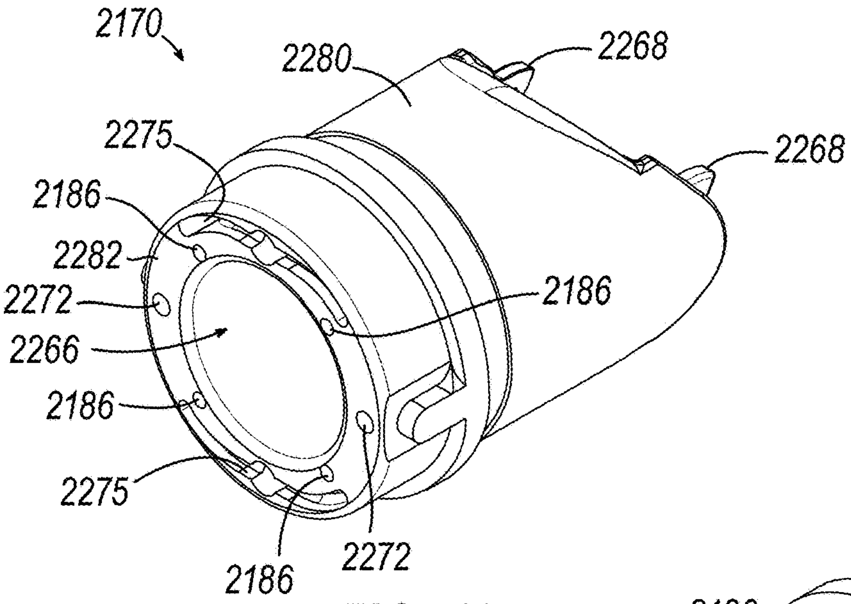
FIG. 49 depicts a rear, distal perspective view of a distal link of the multiplanar articulation section of FIG. 37A.
Figure 50:
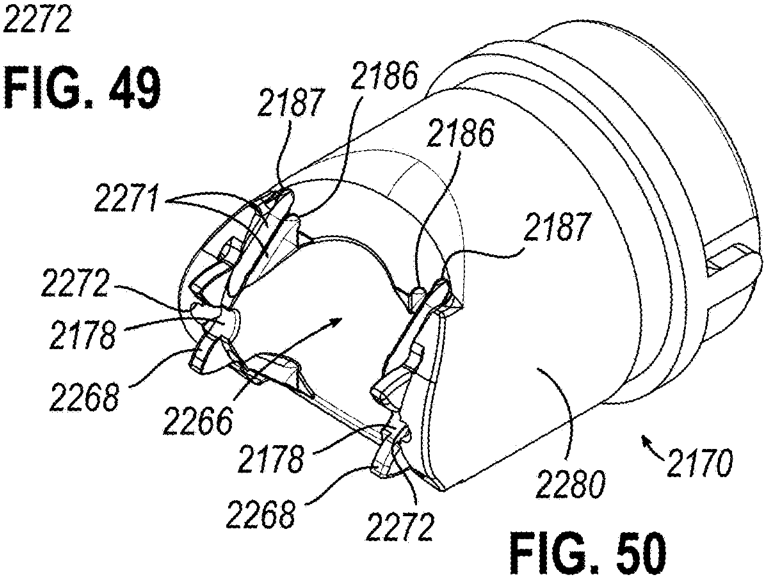
FIG. 50 depicts a rear, proximal perspective view of the distal link of FIG. 49.
Figure 51:
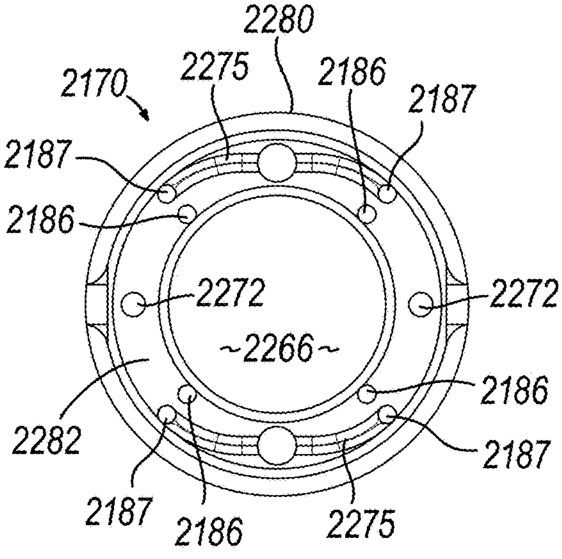
FIG. 51 depicts a distal end elevational view of the distal link of FIG. 49.
Figure 52:
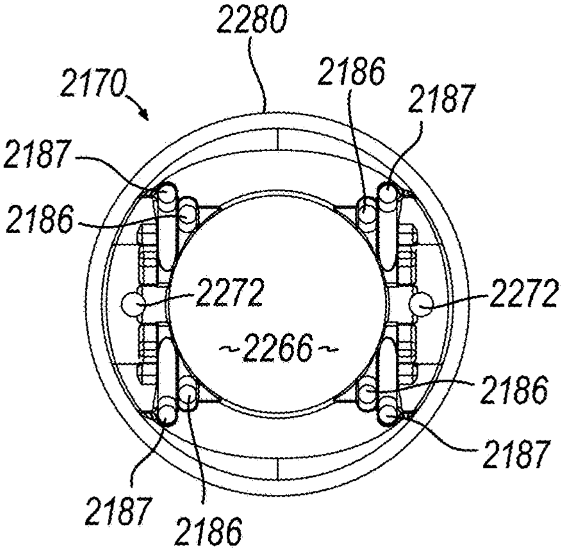
FIG. 52 depicts a proximal end elevational view of the distal link of FIG. 49.
Figure 53:
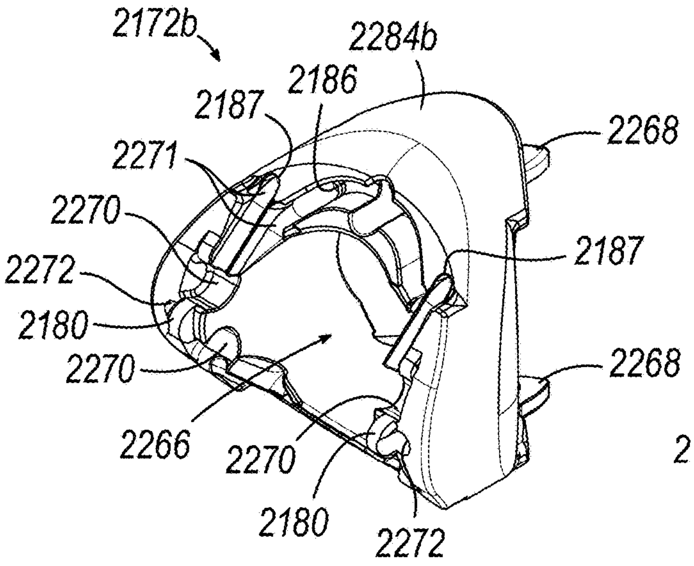
FIG. 53 depicts a rear, distal perspective view of a distal intermediate link of the multiplanar articulation section of FIG. 37A.
Figure 54:
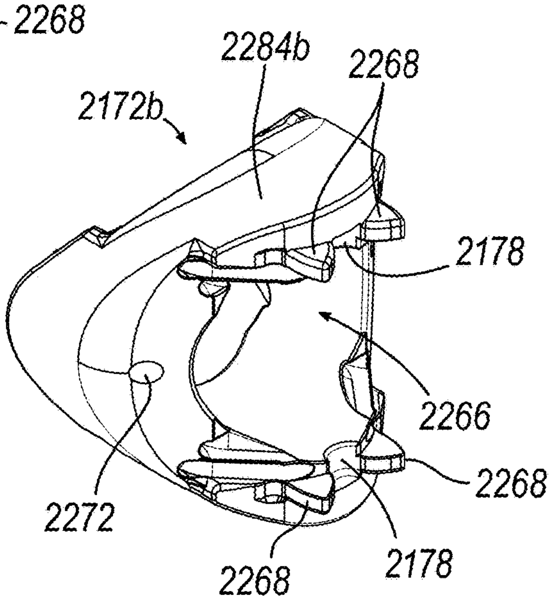
FIG. 54 depicts a rear, proximal perspective view of the distal intermediate link of FIG. 53.
Figure 55:
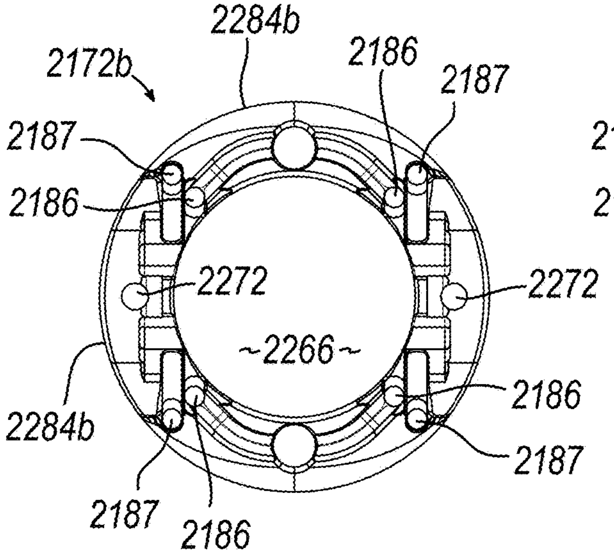
FIG. 55 depicts a distal end elevational view of the distal intermediate link of FIG. 53.
Figure 56:
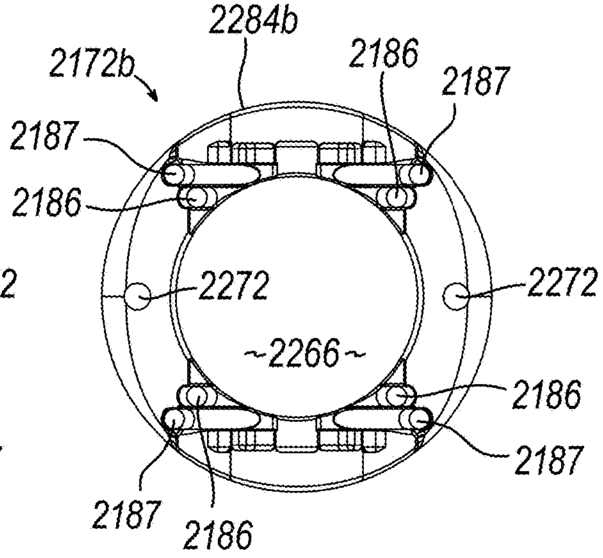
FIG. 56 depicts a proximal end elevational view of the distal intermediate link of FIG. 53.
Figure 57:
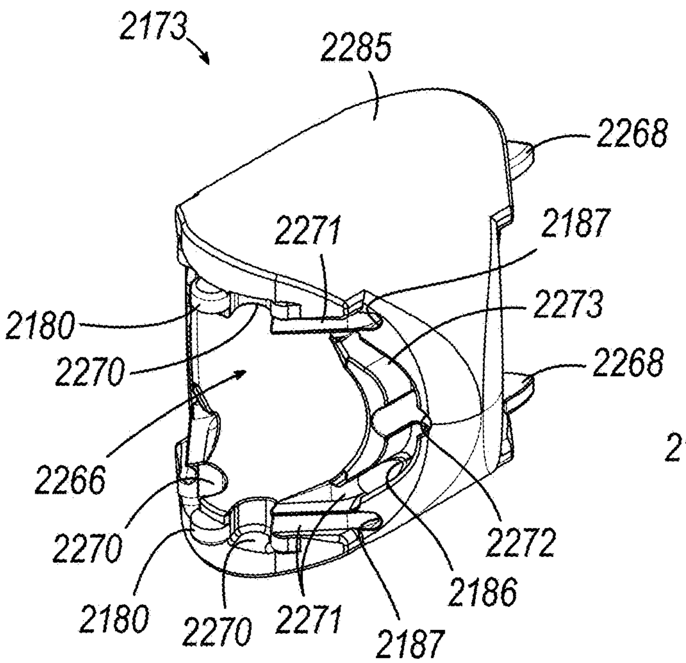
FIG. 57 depicts a rear, distal perspective view of a middle link of the multiplanar articulation section of FIG. 37A.
Figure 58:
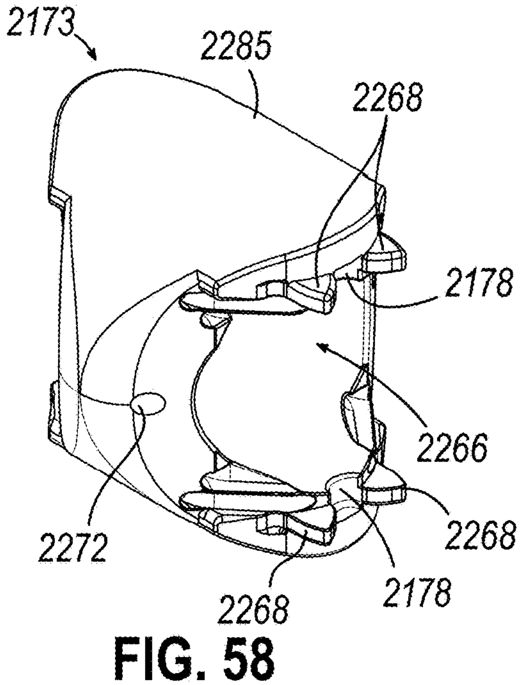
FIG. 58 depicts a rear, proximal perspective view of the middle link of FIG. 57.
Figure 59:
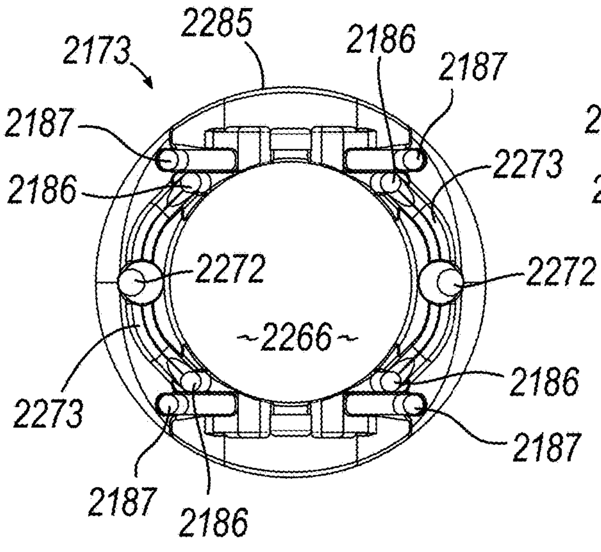
FIG. 59 depicts a distal end elevational view of the middle link of FIG. 57.
Figure 60:
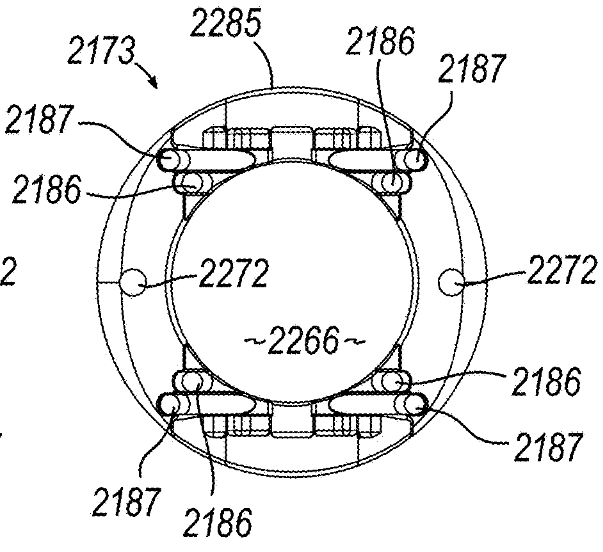
FIG. 60 depicts a proximal end elevational view of the middle link of FIG. 57.
Figure 61:
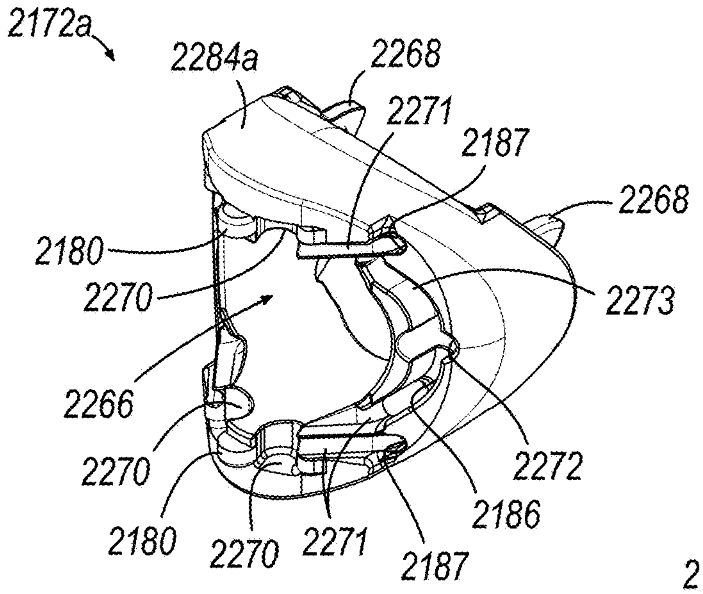
FIG. 61 depicts a rear, distal perspective view of a proximal intermediate link of the multiplanar articulation section of FIG. 37A.
Figure 62:
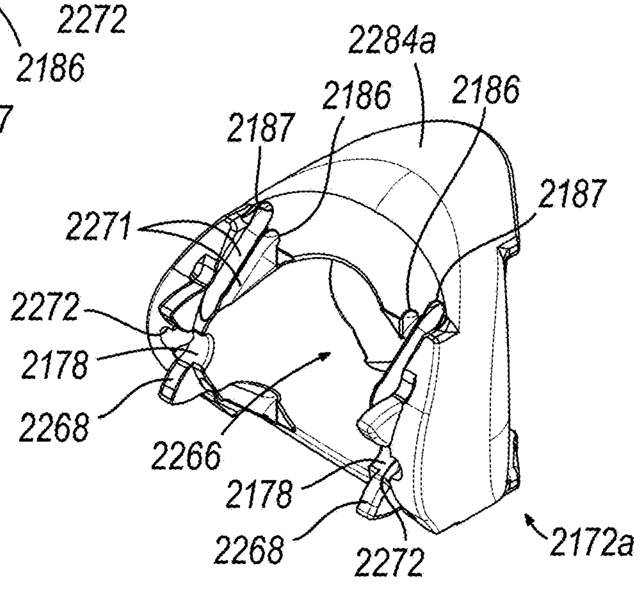
FIG. 62 depicts a rear, proximal perspective view of the proximal intermediate link of FIG. 61.
Figure 63:
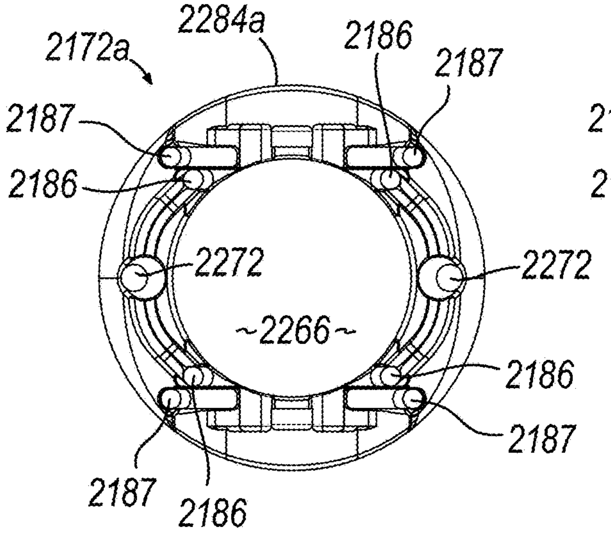
FIG. 63 depicts a distal end elevational view of the proximal intermediate link of FIG. 61.
Figure 64:
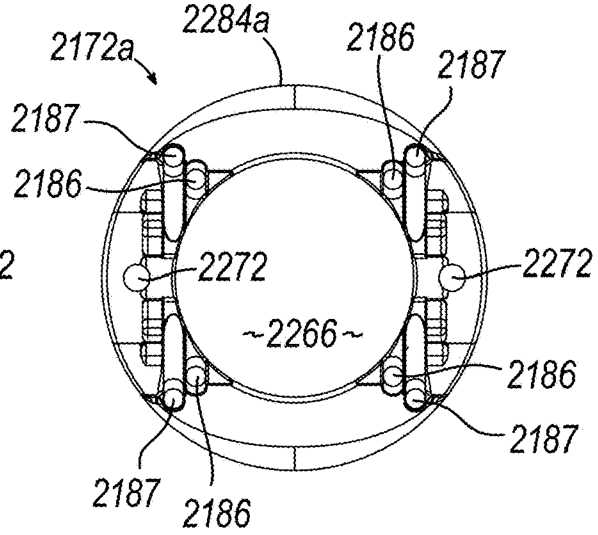
FIG. 64 depicts a proximal end elevational view of the proximal intermediate link of FIG. 61.
Figure 65:
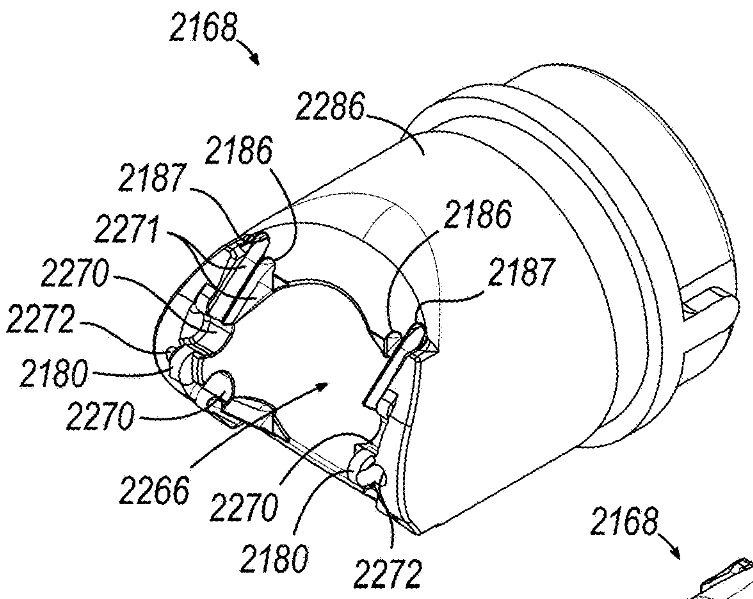
FIG. 65 depicts a rear, distal perspective view of a proximal link of the multiplanar articulation section of FIG. 37A.
Figure 66:
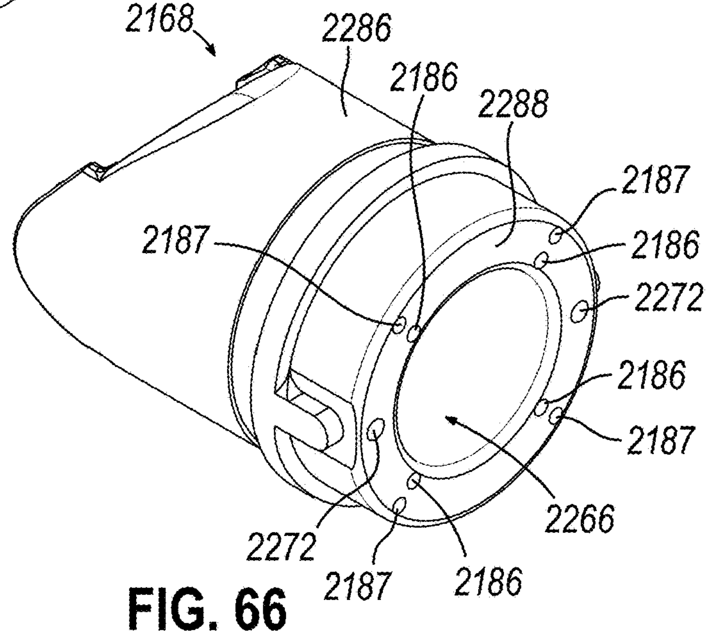
FIG. 66 depicts a rear, proximal perspective view of the proximal link of FIG. 65.
Figure 67:
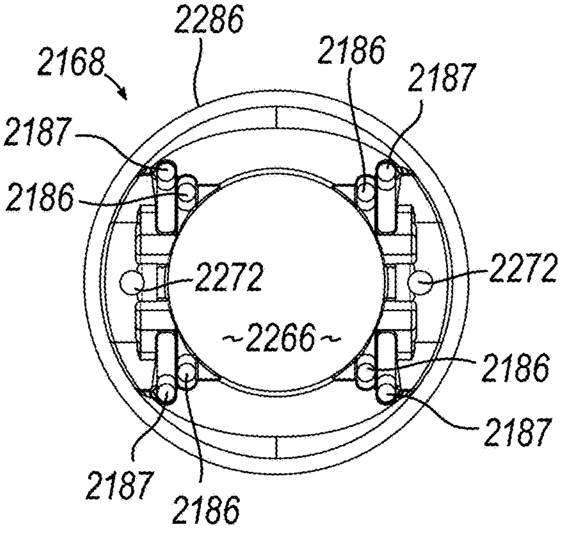
FIG. 67 depicts a distal end elevational view of the proximal link of FIG. 65.
Figure 68:
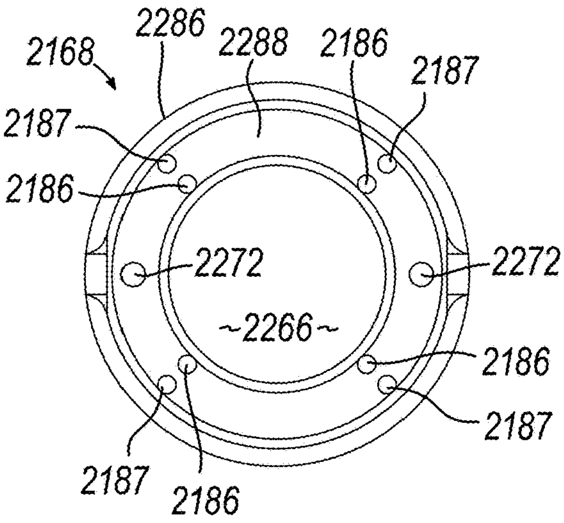
FIG. 68 depicts a proximal end elevational view of the proximal link of FIG. 65.

FIGS. 45-48 show articulation section (2164) with proximal, distal, intermediate, and middle links (2168, 2170, 2172*a-b*, 2173), articulation cable segments (2174*a-d*, 2175*a-d*), and flexible portion (2158) of multi-flex acoustic waveguide (2156) extending therethrough. As best shown in FIGS. 46-48, links (2168, 2170, 2172*a-b*, 2173) collectively define channels (2176*a-d*, 2177*a-d*) configured to receive respective articulation cable segments (2174*a-d*, 2175*a-d*) such that articulation cable segments (2174*a-d*, 2175*a-d*) transversely and/or laterally align links (2168, 2170, 2172*a-b*, 2173) with a remainder of shaft assembly (2114) as well as provide transverse and/or lateral support of links (2168, 2170, 2172*a-b*, 2173) along articulation section (2164). Links (2168, 2170, 2172*a-b*, 2173) have arcuate grooves (2178) receiving arcuate tongues (2180) along respective transverse or lateral centerlines (depending on the angular orientation of the particular link (2168, 2170, 2172*a-b*, 2173)) positioned between pairs of adjacent articulation cable segments (2174*a-d*, 2175*a-d*) such that each pair of adjacent articulation cable segments (2174*a-d*, 2175*a-d*) are transversely or laterally offset and on opposing sides of flexible portion (2158) thereby maintaining axial position of articulation section (2164). Furthermore, each link (2168, 2170, 2172*a-b*, 2173) defines a link hollow (2266) collectively defining an articulation section lumen (2267) configured to receive flexible portion (2158) and provide flexible portion (2158) with sufficient and constant clearance space therealong to remain untouched by any portion of one of links (2168, 2170, 2172*a-b*, 2173) whether in the straight configuration or any articulated configuration, which is limited to maximum articulated configurations via cooperating distal and proximal stops (2268, 2270). To this end, proximal stop (2270) on one link (2168, 2170, 2172*a-b*, 2173) is configured to engage distal stop (2268) on a distally adjacent link (2168, 2170, 2172*a-b*, 2173) to thereby limit collective articulation of articulation section (2164) and, in turn, limit strain due to articulation on flexible portion (2158) of acoustic waveguide (2156).

With respect to FIGS. 46-48, bores (2186, 2187) in each link (2168, 2170, 2172*a-b*, 2173) that collectively define channels (2176*a-d*, 2177*a-d*) are configured to slidably receive respective articulation cable segments (2174*a-d*, 2175*a-d*). In the example shown, radially inner bores (2186) collectively define channels (2176*a-d*) and are configured to slidably receive respective proximal articulation cable segments (2174*a-d*), while radially outer bores (2187) collectively define channels (2177*a-d*) and are configured to slidably receive respective distal articulation cable segments (2175*a-d*). Bores (2186, 2187) also have drafted openings (2271) to inhibit kinking of articulation cable segments (2174*a-d*, 2175*a-d*) during use. In the example shown, pairs of adjacent radially inner bores (2186) are in communication with each other via respective slots (2273) for receiving distal ends of righthand adjacent proximal articulation cable segments (2174*a*, 2174*b*) and lefthand adjacent proximal articulation cable segments (2174*c*, 2174*d*), respectively, such that the distal ends of righthand adjacent proximal articulation cable segments (2174*a*, 2174*b*) may be coupled to each other (e.g., integrally formed together as a single cable) and the distal ends of lefthand adjacent proximal articulation cable segments (2174*c*, 2174*d*) may be coupled to each other (e.g., integrally formed together as a single cable). Likewise, pairs of adjacent radially outer bores (2187) are in communication with each other via respective slots (2275) for receiving distal ends of upper adjacent distal articulation cable segments (2175*a*, 2175*d*) and lower adjacent distal articulation cable segments (2175*b*, 2175*c*), respectively, such that the distal ends of upper adjacent distal articulation cable segments (2175*a*, 2175*d*) may be coupled to each other (e.g., integrally formed together as a single cable) and the distal ends of lower adjacent distal articulation cable segments (2175*b*, 2175*c*) may be coupled to each other (e.g., integrally formed together as a single cable).

Additional control members in the form of closure cables (2152) are also connected between end effector (2116) and the instrument base (not shown) and thus extend through articulation section (2164) in the present example. In this regard, closure cables (2152) are received through at least a portion of arcuate tongues and grooves (2180, 2178) along respective lateral centerlines to inhibit changing lengths associated with articulation of articulation section (2164). More particularly, a pair of passageways (2272) longitudinally extend through each link (2168, 2170, 2172*a-b*, 2173) in alignment with the laterally arranged portion of arcuate tongues and grooves (2180, 2178) to collectively define a pair of additional channels (2274) configured to guide closure cables (2152) through articulation section (2164). Each passageway (2272) may also have a widened groove opening (not shown) and a widened tongue opening (not shown) as respectively applicable to laterally arranged arcuate groove and tongues (2178, 2180) of links (2168, 2170, 2172a-b, 2173). Each of the widened groove and tongue openings may be drafted to inhibit kinking of closure cables (2152) while articulating articulation section (2164) as described herein. In one example, links (2168, 2170, 2172a-b, 2173) may further include a material sleeve (not shown) or material coating (not shown) configured to further inhibit kinking and/or inhibit damage to flexible portion (2158) of acoustic waveguide (2156) in case of incidental contact.

FIGS. 49-52 show distal link (2170) in greater detail in one example having a distal link body (2280) with laterally opposed proximally extending arcuate grooves (2178) with passageways (2272). Distal link body (280) further includes a distally facing coupling surface (2282) configured to be rigidly connected to distal shaft portion (2162). Slots (2275) configured to fixedly receive the distal ends of distal articulation cable segments (2175a-d) are also shown angularly between grooves (2178), whereas distal stops (2268) are respectively positioned about grooves (2178). Of course, distal link (2170) may vary as desired for incorporating articulation section (2164) into shaft assembly (2114) such that the invention is not intended to be unnecessarily limited to the particular distal link (2170) shown in the present example.

FIGS. 53-56 show distal intermediate link (2172b) in greater detail in one example having a distal intermediate link body (2284b) with laterally opposed distally extending arcuate tongues (2180) with passageways (2272) and transversely opposed proximally extending arcuate grooves (2178) shown angularly between tongues (2180). Proximal stops (2270) are respectively positioned about distally facing arcuate tongues (2180), whereas distal stops (2268) are respectively positioned about proximally facing grooves (2178). Of course, distal intermediate link (2172b) may vary as desired for incorporating articulation section (2164) into shaft assembly (2114) such that the invention is not intended to be unnecessarily limited to the particular distal intermediate link (2172b) shown in the present example.

FIGS. 57-60 show middle link (2173) in greater detail in one example having a middle link body (2285) with transversely opposed distally extending arcuate tongues (2180) and transversely opposed proximally extending arcuate grooves (2178). In the example shown, passageways (2272) are shown angularly between tongues (2180) as well as angularly between grooves (2178). Proximal stops (2270) are respectively positioned about distally facing arcuate tongues (2180), whereas distal stops (2268) are respectively positioned about proximally facing grooves (2178). Of course, middle link (2173) may vary as desired for incorporating articulation section (2164) into shaft assembly (2114) such that the invention is not intended to be unnecessarily limited to the particular middle link (2173) shown in the present example.

FIGS. 61-64 show proximal intermediate link (2172a) in greater detail in one example having a proximal intermediate link body (2284a) with transversely opposed distally extending arcuate tongues (2180) and laterally opposed proximally extending arcuate grooves (2178) with passageways (2272) shown angularly between tongues (2180). Proximal stops (2270) are respectively positioned about distally facing arcuate tongues (2180), whereas distal stops (2268) are respectively positioned about proximally facing grooves (2178). Thus, proximal intermediate link (2172a) may be substantially similar to distal intermediate link (2172b) except for the locations of passageways (2272) for accommodating the different angular orientations of proximal and intermediate links (2172a, 2172b) shown in the present example of articulation section (2164). Of course, proximal intermediate link (2172a) may vary as desired for incorporating articulation section (2164) into shaft assembly (2114) such that the invention is not intended to be unnecessarily limited to the particular proximal intermediate link (2172a) shown in the present example.

FIGS. 65-68 show proximal link (2168) in greater detail in one example having a proximal link body (2286) with laterally opposed distally extending arcuate tongues (2180) with passageways (2272). Proximal link body (2286) further includes a proximally facing coupling surface (2288) configured to be rigidly connected to proximal shaft portion (2160). Bores (2186, 2187) are configured to receive respective articulation cable segments (2174a-d, 2175a-d) and shown angularly between arcuate tongues (2180), whereas proximal stops (2270) are respectively positioned about arcuate tongues (2180). Of course, proximal link (2168) may vary as desired for incorporating articulation section (2164 into shaft assembly (2114) such that the invention is not intended to be unnecessarily limited to the particular proximal link (2168) shown in the present example.

In use, referring back to FIGS. 38A-44, the operator selectively directs articulation sections (2164) in order to deflect end effector (2116) relative to longitudinal axes (2161, 2165). In one example, either proximal intermediate link (2172a) or middle link (2173) of articulation section (2164) articulates in order to deflect a distal remainder of shaft assembly (2114) with end effector (2116) through either the pitch plane or the yaw plane, respectively, relative to axis (2161), and then either distal intermediate link (2172b) or distal link (2170) of articulation section (2164) articulates in order to deflect a further distal remainder of shaft assembly (2114) with end effector (2116) through either the yaw plane or the pitch plane, respectively, relative to axis (2165). In another example, either distal intermediate link (2172b) or distal link (2170) of articulation section (2164) articulates in order to deflect a further distal remainder of shaft assembly (2114) with end effector (2116) through either the yaw plane or the pitch plane, respectively, relative to axis (2165), and then either proximal intermediate link (2172a) or middle link (2173) of articulation section (2164) articulates in order to deflect a distal remainder of shaft assembly (2114) with end effector (2116) through either the pitch plane or the yaw plane, respectively, relative to axis (2161). In still another example, either proximal intermediate link (2172a) or middle link (2173) and either distal intermediate link (2172b) or distal link (2170) of articulation section (2164) simultaneously articulate in order to deflect remainders of shaft assembly (2114) with end effector (2116) through the respective pitch and/or yaw planes. Alternatively, any one of proximal intermediate link (2172a), middle link (2173), distal intermediate link (2172b), or distal link (2170) of articulation section (2164) are articulated without articulating the distal remainder of articulation sections (2164). In any case, end effector (2116) is thereby configured to deflect through at least two distinct planes via multiplanar articulation section (2164).

While the present example provides two distinct planes through which to move end effector (2116) via a series of joints of multiplanar articulation section (2164) at discrete longitudinal positions, an alternative articulation section may be configured to provide articulation in at least two distinct planes in a single joint capable of articulating through at least two planes in one discrete longitudinal position. In addition, or alternatively, a plurality of articulation sections may be used to provide articulation in at least two distinct planes. The invention is thus not intended to be unnecessarily limited to a single multiplanar articulation section (2164) as shown in the present example for multi-planar articulation.

In the present example, flexible portion (2158) of multi-flex acoustic waveguide (2156) is configured to flex in a full 360-degree range of radial directions through a respective full 360-degree range of radial planes. As best shown in FIG. 45, waveguide (2156) of the present example includes a proximal waveguide body portion (2560) extending along longitudinal axis (2161), a distal waveguide body portion (2562) distally extending to ultrasonic blade (2146) along longitudinal axis (2163), and flexible portion (2158) longitudinally extending therebetween. Flexible portion (2158) is thus configured to flex in any radial direction about longitudinal axis (2161) to thereby deflect ultrasonic blade (2146) relative to longitudinal axis (2161) through any respective radial plane for multi-planar deflection. In the present example, proximal waveguide body portion (2560), flexible portion (2158), distal waveguide body portion (2562), and ultrasonic blade (2146) have a single, unitary construction, although multi-flex acoustic waveguide (2156) may be alternatively constructed with one or more connected structures. The invention is thus not intended to be unnecessarily limited to single, unitary construction of multi-flex acoustic waveguide (2156) shown in the present example.

More particularly, as best shown in FIG. 45, flexible portion (2158) is provided in the form of an exemplary flexible wire configured to flex in any radial direction about longitudinal axis (2161) to thereby deflect ultrasonic blade (2146) relative to longitudinal axis (2161) through any respective radial plane for multi-planar deflection. In this regard, flexible portion (2158) is elongated, cylindrical, and concentric with waveguide body portions (2560, 2562). A boss (2572) is positioned on distal waveguide body portion (2562) and so as to coincide with and, more particularly, be centered on an acoustic node along multi-flex acoustic waveguide (2156). Similarly, flexible portion (2158) is positioned and centered on an acoustic antinode of multi-flex acoustic waveguide (2156). Each proximal and distal waveguide body portion (2560, 2562) is more rigid than flexible portion (2158) and is conically tapered to narrow toward flexible portion (2158). By way of example only, waveguide (2156) may be constructed in accordance with at least some of the teachings of U.S. patent application Ser. No. 16/556,661, entitled "Ultrasonic Surgical Instrument with a Multi-Planar Articulating Shaft Assembly," filed on Aug. 30, 2019.

In the example shown, proximal and distal waveguide body portions (2560, 2562) are fixedly secured to proximal and distal shaft portions (2160, 2162), respectively, such that distal waveguide body portion (2562) and ultrasonic blade (2146) may deflect together with distal shaft portion (2162) relative to longitudinal axis (2161) and/or axis (2165). In this manner, distal shaft portion (2162) may guide deflection of distal waveguide portion (2562) relative to longitudinal axis (2161) and/or axis (2165). Such deflection of distal waveguide body portion (2562) may result in selective bending of flexible portion (2158) relative to longitudinal axis (2161) about a bend radius. It will be appreciated that the bend radius of flexible portion (2158) may vary as a function of the angle(s) of articulation of the distal portion of shaft assembly (2114) relative to longitudinal axis (2161) and/or axis (2165). In some versions, articulation section lumen (2267) is sized and shaped to provide flexible portion (2158) with sufficient and constant clearance space therealong to remain untouched by any portion of one of links (2168, 2170, 2172*a*-*b*, 2173) when flexible portion (2158) is selectively bent to a maximum bend radius as limited by interaction between cooperating distal and proximal stops (2268, 2270). While the present example shows distal waveguide body portion (2562) fixedly secured to distal shaft portion (2162) via frictional engagement between boss (2572) and distal shaft portion (2162), it will be appreciated that waveguide body portions (2560, 2562) may be fixedly secured to the respective shaft portions (2160, 2162) via any suitable fixation means including, but not limited to, one or more pins extending laterally and/or transversely through waveguide body portions (2560, 2562) and the respective shaft portions (2160, 2162), and the fixation means discussed above.

B. Second Exemplary Multiplanar Articulation Section

Figure 69:
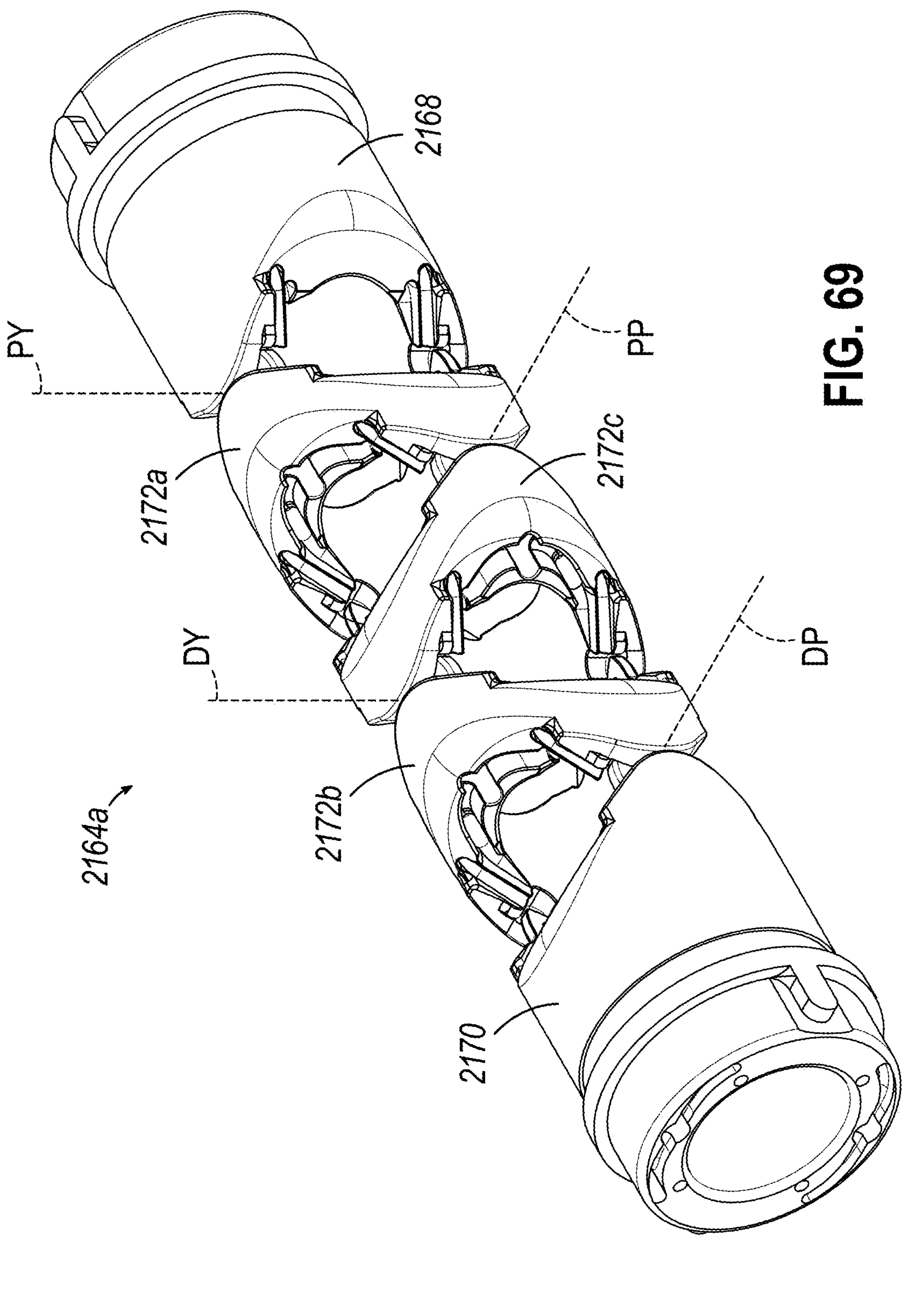
FIG. 69 depicts a perspective view of another exemplary multiplanar articulation section for the shaft assembly of FIG. 37A.

FIG. 69 shows an alternative multiplanar articulation section (2164*a*) including proximal link (2168), distal link (2170), and a plurality of intermediate links (2172*a*-*c*) connected in series between proximal and distal links (2168, 2170). Articulation section (2164) further includes a plurality of proximal articulation cable segments (not shown), which may be grounded to middle intermediate link (2172*c*), and a plurality of distal articulation cable segments (not shown), which may be grounded to distal link (2170). Thus, articulation section (2164*a*) may be substantially similar to articulation section (2164) except for the replacement of middle link (2173) by middle intermediate link (2172*c*) and the different angular orientations of proximal intermediate link (2172*b*) and proximal link (2168), which may allow proximal yaw axis (PY) to be positioned proximally (rather than distally) relative to proximal pitch axis (PP). It will be appreciated that any other suitable configurations and/or relative positions/orientations of links may be used to provide a multiplanar articulation section having one or more pitch and yaw axes in any desired number and/or arrangement.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) an end effector, wherein the end effector comprises: (i) an ultrasonic blade, and (ii) a clamp arm configured to move relative to the ultrasonic blade between an open position and a closed position; (b) a shaft assembly, comprising: (i) a proximal shaft portion extending along a longitudinal axis, (ii) an acoustic waveguide extending proximally from the ultrasonic blade, wherein the acoustic waveguide comprises a flexible portion, (iii) a distal shaft portion extending along a distal axis, and (iv) an articulation section interposed between the proximal shaft portion and the distal shaft portion, wherein the flexible portion of the acoustic waveguide extends along the articulation section, wherein the articulation section is configured to deflect the distal shaft portion and the end effector relative to the longitudinal axis between a straight configuration and an articulated configuration; and (c) a waveguide grounding feature associated with the distal shaft portion, wherein the waveguide grounding feature is configured to inhibit the ultrasonic blade from shifting relative to the clamp arm along the distal axis as the end effector is driven between the straight configuration and the articulated configuration.

Example 2

The ultrasonic surgical instrument of Example 1, wherein the waveguide grounding feature comprises a pin extending through the acoustic waveguide.

Example 3

The ultrasonic surgical instrument of Example 2, wherein the acoustic waveguide comprises a distal flange housed within the distal shaft portion, wherein the pin extends from the distal flange.

Example 4

The ultrasonic surgical instrument of Example 3, wherein the distal flange defines a pin hole, wherein the pin extends within the pin hole.

Example 5

The ultrasonic surgical instrument of any one or more of Examples 3 through 4, wherein the waveguide grounding feature comprises a flange sleeve surrounding the distal flange.

Example 6

The ultrasonic surgical instrument of Example 5, wherein the flange sleeve defines a pin hole, wherein the pin extends through the pin hole.

Example 7

The ultrasonic surgical instrument of Example 6, wherein the flange sleeve is longitudinally constrained within the distal shaft portion.

Example 8

The ultrasonic surgical instrument of Example 7, wherein the flange sleeve is configured to impart a compressional force onto the distal flange.

Example 9

The ultrasonic surgical instrument of any one or more of Examples 6 through 8, wherein the flange sleeve comprises an open proximal end configured to abut against an interior of the distal shaft portion.

Example 10

The ultrasonic surgical instrument of Example 9, wherein the flange sleeve comprises an open distal end configured to abut again the interior of the distal shaft portion.

Example 11

The ultrasonic surgical instrument of any one or more of Examples 1 through 10, wherein the acoustic waveguide comprises a proximal portion extending proximally from the flexible portion, wherein the proximal portion of the acoustic waveguide does not include a pin extending from the proximal portion.

Example 12

The ultrasonic surgical instrument of Example 11, further comprising a drive chassis associated with the proximal shaft portion.

Example 13

The ultrasonic surgical instrument of Example 12, wherein the drive chassis comprises a chassis frame and an articulation drive assembly configured to drive articulation section, wherein the chassis frame rotatably supports the articulation drive assembly.

Example 14

The ultrasonic surgical instrument of Example 13, further comprising a transducer assembly coupled with the acoustic waveguide, wherein the transducer assembly is coupled with the chassis frame such that the chassis frame is configured to rotate the transducer assembly about the longitudinal axis.

Example 15

The ultrasonic surgical instrument of Example 14, wherein the transducer assembly is configured to selectively couple with the acoustic waveguide.

Example 16

An ultrasonic surgical instrument, comprising: (a) an end effector, wherein the end effector comprises: (i) an ultrasonic blade, and (ii) a clamp arm configured to move relative to the ultrasonic blade between an open position and a closed position; (b) a shaft assembly, comprising: (i) a proximal shaft portion extending along a longitudinal axis, (ii) an acoustic waveguide extending proximally from the ultrasonic blade, wherein the acoustic waveguide comprises a flexible portion, (iii) a distal shaft portion extending along a distal axis, and (iv) an articulation section interposed between the proximal shaft portion and the distal shaft portion, wherein the articulation section is configured to bend the flexible portion of the acoustic waveguide along a first arc length and deflect the distal shaft portion along a second arc length in order to drive the end effector into an articulated configuration; and (c) an axial location feature configured to inhibit the ultrasonic blade from shifting relative to the clamp arm along the distal axis as the end effector is driven into the articulated configuration.

Example 17

The ultrasonic surgical instrument of Example 16, wherein the axial location feature comprises a sleeve surrounding a distal flange of the acoustic waveguide.

Example 18

The ultrasonic surgical instrument of Example 17, wherein the axial location feature further comprises pin extending through the sleeve and the distal flange.

Example 19

The ultrasonic surgical instrument of any one or more of Examples 16 through 18, wherein the end effector further comprises a clamp pad coupled with the clamp arm.

Example 20

An ultrasonic surgical instrument, comprising: (a) an end effector, wherein the end effector comprises: (i) an ultrasonic blade, and (ii) a clamp arm configured to move relative to the ultrasonic blade between an open position and a closed position; (b) a shaft assembly, comprising: (i) a distal shaft portion extending along a distal axis, and (ii) an articulation section, wherein the articulation section is configured to bend the ultrasonic blade along a first arc length and deflect the distal shaft portion along a second arc length in order to drive the end effector into an articulated configuration; and (c) an axial location feature configured to inhibit the ultrasonic blade from shifting relative to the clamp arm along the distal axis as the end effector is driven into the articulated configuration.

VII. Miscellaneous

Any one or more of the teaching, expressions, embodiments, examples, etc. described herein may be combined with any one or more of the teachings, expressions, embodiments, examples, etc. described in U.S. patent application Ser. No. 17/077,067, entitled “Surgical Instrument and Carrier KART Supporting Ultrasonic Transducer,” filed on Oct. 22, 2022, published as U.S. Pub. No. 2022/0125465 on Apr. 28, 2022; U.S. patent application Ser. No. 17/077,086, entitled “Carrier KART and Jaw Closure of an Ultrasonic Surgical Instrument,” filed on Oct. 22, 2022, published as U.S. Pub. No. 2022/0125466 on Apr. 28, 2022; U.S. patent application Ser. No. 17/077,130, entitled “Surgical Instrument with Clamping Sensor Feedback and Related Methods,” filed on Oct. 22, 2022, published as U.S. Pub. No. 2022/0125469 on Apr. 28, 2022; U.S. patent application Ser. No. 17/077,136, entitled “Surgical Instrument with Nonclamping Sensor Feedback and Related Methods,” filed on Oct. 22, 2022, published as U.S. Pub. No. 2022/0125470 on Apr. 28, 2022; U.S. patent application Ser. No. 17/077,250, entitled “Ultrasonic Surgical Instrument with a Carrier KART and Reusable Stage,” filed on Oct. 22, 2022, published as U.S. Pub. No. 2022/0125472 on Apr. 28, 2022; U.S. patent application Ser. No. 17/077,373, entitled “Surgical Instrument with a Carrier KART and Various Communication Cable Arrangements,” filed on Oct. 22, 2022, published as U.S. Pub. No. 2022/0125473 on Apr. 28, 2022, issued as U.S. Pat. No. 11,931,059 on Mar. 19, 2024; U.S. patent application Ser. No. 17/077,139, entitled “Ultrasonic Surgical Instrument with a Fixed Transducer Grounding,” filed on Oct. 22, 2022, published as U.S. Pub. No. 2022/0125471 on Apr. 28, 2022; U.S. patent application Ser. No. 17/077,146, entitled “Ultrasonic Surgical Instrument with a Shaft Assembly and Elongated Waveguide Support Arrangement,” filed on Oct. 22, 2022, published as U.S. Pub. No. 2022/0125460 on Apr. 28, 2022; U.S. patent application Ser. No. 17/077,152, entitled “Damping Rings for an Ultrasonic Surgical Instrument,” filed on Oct. 22, 2022, issued as U.S. Pat. No. 11,806,037 on Nov. 7, 2023; U.S. patent application Ser. No. 17/077,110, entitled “Ultrasonic Surgical Instrument with a Mid-Shaft Closure System and Related Methods,” filed on Oct. 22, 2022, published as U.S. Pub. No. 2022/0125468 on Apr. 28, 2022, issued as U.S. Pat. No. 11,944,341 on Apr. 2, 2024; U.S. patent application Ser. No. 17/076,956, entitled “Surgical Instrument with an Articulatable Shaft Assembly and Dual End Effector Roll,” filed on Oct. 22, 2022, published as U.S. Pub. No. 2022/0125463 on Apr. 28, 2022, issued as U.S. Pat. No. 11,890,030 on Feb. 6, 2024; and/or U.S. patent application Ser. No. 17/077,098, entitled “Ultrasonic Surgical Instrument with a Multiplanar Articulation Joint,” filed on Oct. 22, 2022, published as U.S. Pub. No. 2022/0125467 on Apr. 28, 2022. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:

(a) a shaft assembly, wherein the shaft assembly comprises:

(i) a proximal shaft portion extending along a longitudinal axis, and (ii) an articulation section extending distally from the proximal shaft portion, wherein the articulation section includes a proximal link, a distal link, a pair of intermediate links connected in series between the proximal and distal links, and a middle link interposed between the pair of intermediate links;

(b) a waveguide including a proximal portion, a proximal transition portion, a distal transition portion, a distal portion, and a flexible portion, wherein the flexible portion is directly coupled to both the proximal transition portion and the distal transition portion, an entirety of a cross-sectional area of the flexible portion is less than a cross-sectional area of the proximal portion and less than a cross-sectional area of the distal portion, the proximal transition portion having a cross-sectional area greater than the cross-sectional area of the flexible portion and less than the cross-sectional area of the proximal portion, the distal transition portion having a cross-sectional area greater than the cross-sectional area of the flexible portion and less than the cross-sectional area of the distal portion, and the flexible portion extends at least partially through the articulation section; and (c) an end effector arranged at a distal end of the shaft assembly, wherein the end effector includes an ultrasonic blade acoustically coupled with the waveguide and configured to be driven by the waveguide with ultrasonic energy, wherein the links of the articulation section are configured to selectively bend the flexible portion to thereby deflect the end effector relative to the longitudinal axis and through a first plane, wherein the links of the articulation section are further configured to selectively bend the flexible portion to thereby deflect the end effector relative to the longitudinal axis and through a second plane, and wherein the second plane is perpendicular to the first plane for multiplanar deflection of the end effector relative to the longitudinal axis.

2. The ultrasonic surgical instrument of claim 1, wherein the cross-sectional area of the proximal transition portion, in its entirety, is greater than the cross-sectional area of the flexible portion.

3. The ultrasonic surgical instrument of claim 1, wherein the cross-sectional area of the distal transition portion, in its entirety, is greater than the cross-sectional area of the flexible portion.

4. The ultrasonic surgical instrument of claim 1, wherein the cross-sectional area of the proximal transition portion decreases along the longitudinal axis from the proximal portion to the flexible portion.

5. The ultrasonic surgical instrument of claim 4, wherein the cross-sectional area of the proximal transition portion decreases linearly along the longitudinal axis from the proximal portion to the flexible portion.

6. The ultrasonic surgical instrument of claim 1, wherein the cross-sectional area of the distal transition portion increases along the longitudinal axis from the flexible portion to the distal portion.

7. An ultrasonic surgical instrument, comprising:

(a) an end effector including an ultrasonic blade; and (b) a shaft assembly, including:

(i) a proximal shaft portion defining a longitudinal axis, (ii) a distal shaft portion, (iii) an articulation section extending between the proximal and distal shaft portions, wherein the articulation section includes a proximal link, a distal link, a pair of intermediate links connected in series between the proximal and distal links, and a middle link interposed between the pair of intermediate links, and (c) a waveguide including a proximal portion, a proximal transition portion, a distal transition portion, a distal portion, and a flexible portion, wherein the flexible portion is directly coupled to both the proximal transition portion and the distal transition portion, an entirety of a cross-sectional area of the flexible portion is less than a cross-sectional area of the proximal portion and less than a cross-sectional area of the distal portion, the proximal transition portion having a cross-sectional area greater than the cross-sectional area of the flexible portion and less than the cross-sectional area of the proximal portion, the distal transition portion having a cross-sectional area greater than the cross-sectional area of the flexible portion and less than the cross-sectional area of the distal portion, and the flexible portion extends at least partially through the articulation section, wherein the links of the articulation section are configured to articulate in a first direction to thereby deflect the ultrasonic blade relative to the longitudinal axis and through a first plane, wherein the links of the articulation section are further configured to articulate in a second direction to thereby deflect the ultrasonic blade relative to the longitudinal axis and through a second plane, wherein the second direction is perpendicular to the first direction such that the second plane is perpendicular to the first plane for multiplanar deflection of the ultrasonic blade relative to the longitudinal axis.

8. The ultrasonic surgical instrument of claim 7, wherein the articulation section of the shaft assembly defines an articulation section lumen configured to provide clearance between the flexible portion of the waveguide and the articulation section throughout deflection of the end effector relative to the longitudinal axis through the first and second planes.

9. The ultrasonic surgical instrument of claim 7, wherein adjacent links of the articulation section define a plurality of rotational axes, wherein the articulation section is configured to selectively rotate the end effector about the rotational axes during deflection of the end effector relative to the longitudinal axis through at least one of the first or second planes.

10. The ultrasonic surgical instrument of claim 9, wherein the plurality of rotational axes includes at least one pitch axis and at least one yaw axis.

11. The ultrasonic surgical instrument of claim 9, wherein the plurality of rotational axes includes a proximal pitch axis and a distal pitch axis.

12. The ultrasonic surgical instrument of claim 9, wherein the plurality of rotational axes includes a proximal yaw axis and a distal yaw axis.

13. The ultrasonic surgical instrument of claim 9, further comprising a plurality of articulation cable segments grounded to at least a portion of the articulation section of the shaft assembly, wherein selective manipulation of the articulation cable segments causes deflection of the end effector relative to the longitudinal axis through the first and second planes.

14. The ultrasonic surgical instrument of claim 7, wherein the articulation section of the shaft assembly is configured to limit the flexible portion of the waveguide to a predetermined maximum bend radius.

15. The ultrasonic surgical instrument of claim 14, wherein the articulation section of the shaft assembly defines an articulation section lumen configured to provide clearance between the flexible portion of the waveguide and the articulation section when the flexible portion of the waveguide is bent to the predetermined maximum bend radius.

16. The ultrasonic surgical instrument of claim 7, wherein the end effector further includes a clamp arm movably secured relative to the ultrasonic blade and configured to move from an open position configured to receive a tissue toward a closed position configured to clamp the tissue against the ultrasonic blade, the ultrasonic surgical instrument further comprising at least one closure cable extending distally through the articulation section to the clamp arm and configured to actuate the clamp arm from one of the open or closed positions toward the other of the open or closed positions.

* * * * *